US009555099B2

(12) United States Patent
Dubensky, Jr. et al.

(10) Patent No.: US 9,555,099 B2
(45) Date of Patent: Jan. 31, 2017

(54) VACCINES FOR HSV-2

(71) Applicant: IMMUNE DESIGN CORP., Seattle, WA (US)

(72) Inventors: Thomas W. Dubensky, Jr., Seattle, WA (US); Nancy A. Hosken, Seattle, WA (US); Scott H. Robbins, Lake Forest Park, WA (US); Margaret D. Moore, Seattle, WA (US)

(73) Assignee: IMMUNE DESIGN CORP., Seattle, WA (US)

( * ) Notice: Subject to any disclaimer, the term of this patent is extended or adjusted under 35 U.S.C. 154(b) by 0 days.

(21) Appl. No.: 13/895,888

(22) Filed: May 16, 2013

(65) Prior Publication Data

US 2014/0086947 A1 Mar. 27, 2014

Related U.S. Application Data

(60) Provisional application No. 61/647,764, filed on May 16, 2012, provisional application No. 61/679,387, filed on Aug. 3, 2012, provisional application No. 61/714,158, filed on Oct. 15, 2012.

(51) Int. Cl.
*A61K 39/245* (2006.01)
*C07K 14/005* (2006.01)
*A61K 39/12* (2006.01)
*A61K 38/00* (2006.01)
*A61K 39/00* (2006.01)

(52) U.S. Cl.
CPC .............. *A61K 39/245* (2013.01); *A61K 39/12* (2013.01); *C07K 14/005* (2013.01); *A61K 38/00* (2013.01); *A61K 2039/545* (2013.01); *A61K 2039/55572* (2013.01); *C12N 2710/16622* (2013.01); *C12N 2710/16634* (2013.01)

(58) Field of Classification Search
None
See application file for complete search history.

(56) References Cited

U.S. PATENT DOCUMENTS

| 4,709,011 | A | 11/1987 | Cohen et al. |
| 4,762,708 | A | 8/1988 | Cohen et al. |
| 4,818,694 | A | 4/1989 | Watson et al. |
| 4,891,315 | A | 1/1990 | Watson et al. |
| 5,149,259 | A | 9/1992 | Greco |
| 5,149,532 | A | 9/1992 | Brunell |
| 5,171,568 | A | 12/1992 | Burke et al. |
| 5,709,860 | A | 1/1998 | Raychaudhuri et al. |
| 5,709,879 | A | 1/1998 | Barchfeld et al. |
| 5,747,039 | A | 5/1998 | Burke et al. |
| 5,837,260 | A | 11/1998 | Cohen et al. |
| 5,851,533 | A | 12/1998 | Berman et al. |
| 6,027,730 | A | 2/2000 | Francotte et al. |
| 6,413,518 | B1 | 7/2002 | Koelle et al. |
| 6,451,325 | B1 | 9/2002 | Van Nest et al. |
| 6,692,752 | B1 | 2/2004 | Slaoui et al. |
| 6,814,969 | B2 | 11/2004 | Koelle et al. |
| 6,821,519 | B2 | 11/2004 | Day et al. |
| 7,078,041 | B2 | 7/2006 | Koelle et al. |
| 7,094,767 | B2 | 8/2006 | Armstrong et al. |
| 7,264,817 | B1 | 9/2007 | Berman et al. |
| 7,666,434 | B2 | 2/2010 | Koelle et al. |
| 7,744,899 | B2 | 6/2010 | Whitley et al. |
| 7,744,903 | B2 | 6/2010 | Koelle et al. |
| 8,067,010 | B2 | 11/2011 | Koelle et al. |
| 8,575,070 | B2 * | 11/2013 | Watt et al. ...................... 506/25 |
| 8,617,564 | B2 | 12/2013 | Long et al. |
| 2003/0068327 | A1 | 4/2003 | Hosken et al. |
| 2003/0118611 | A1 | 6/2003 | Koelle et al. |
| 2003/0165819 | A1 | 9/2003 | McGowan et al. |
| 2003/0165820 | A1 * | 9/2003 | Day et al. ......................... 435/5 |
| 2005/0130132 | A1 | 6/2005 | Day et al. |
| 2008/0081768 | A1 * | 4/2008 | Watt et al. ........................ 506/9 |
| 2008/0299140 | A1 | 12/2008 | Georges et al. |
| 2009/0181078 | A1 * | 7/2009 | Reed et al. ................... 424/450 |
| 2010/0160419 | A1 | 6/2010 | Vilalta et al. |
| 2010/0330112 | A1 | 12/2010 | Long et al. |
| 2012/0027789 | A1 | 2/2012 | Corey et al. |
| 2012/0263754 | A1 * | 10/2012 | Dubensky et al. ......... 424/204.1 |
| 2012/0288515 | A1 * | 11/2012 | Robbins et al. ............ 424/186.1 |
| 2012/0328655 | A1 * | 12/2012 | Dubensky et al. ......... 424/231.1 |
| 2013/0224236 | A1 * | 8/2013 | Koelle et al. .............. 424/186.1 |
| 2014/0127247 | A1 * | 5/2014 | Dubensky et al. ......... 424/186.1 |

(Continued)

FOREIGN PATENT DOCUMENTS

| WO | WO-95/18148 A1 | 7/1995 |
| WO | WO-98/20016 A1 | 5/1998 |

(Continued)

OTHER PUBLICATIONS

Bowman BR, Baker ML, Rixon FJ, Chiu W, Quiocho FA. Structure of the herpesvirus major capsid protein. EMBO J. Feb. 17, 2003;22(4):757-65.*
NCBI GenBank Reference Sequence: NP_044488.1; major capsid protein [Human herpesvirus 2]. Sub. Aug. 1, 2000; last revision Apr. 23, 2010.*
Coler RN, Baldwin SL, Shaverdian N, Bertholet S, Reed SJ, Raman VS, Lu X, DeVos J, Hancock K, Katz JM, Vedvick TS, Duthie MS, Clegg Ch, Van Hoeven N, Reed SG. A synthetic adjuvant to enhance and expand immune responses to influenza vaccines. PLoS One. Oct. 27, 2010;5(10):e1 3677.*
Ikeda S, Tominaga T, Nishimura C, Homma JY, Kiso M, Hasegawa A. Antiherpes activity of chemically synthesized lipid A-subunit analogue GLA-60 in immunosuppressed mice. Antiviral Res. May-Jun. 1989;11(4):173-80.*

(Continued)

*Primary Examiner* — Stacy B Chen
(74) *Attorney, Agent, or Firm* — Marshall, Gerstein & Borun LLP

(57) ABSTRACT

Compositions of recombinant HSV-2 proteins and an agonist of the innate immune system, such as an adjuvant, are provided as a vaccine. Proteins include an envelope glycoprotein and a structural protein other than an envelope glycoprotein, e.g., a capsid or tegument protein. The vaccine is for use in either HSV-2 seropositive or seronegative subjects.

14 Claims, 20 Drawing Sheets

(56) References Cited

U.S. PATENT DOCUMENTS

| | | | |
|---|---|---|---|
| 2014/0128268 A1* | 5/2014 | Watt et al. | 506/2 |
| 2014/0193460 A1* | 7/2014 | Spector et al. | 424/231.1 |
| 2014/0227307 A1 | 8/2014 | Long et al. | |
| 2014/0328870 A1 | 11/2014 | Long et al. | |

FOREIGN PATENT DOCUMENTS

| | | |
|---|---|---|
| WO | WO-03/086308 A2 | 10/2003 |
| WO | WO-2007/097923 A2 | 8/2007 |
| WO | WO-2010/115172 A2 | 10/2010 |
| WO | WO 2013006569 A2 * | 1/2013 |

OTHER PUBLICATIONS

Hoshino Y, Pesnicak L, Dowdell KC, Burbelo PD, Knipe DM, Straus SE, Cohen JI. Protection from herpes simplex virus (HSV)-2 infection with replication-defective HSV-2 or glycoprotein D2 vaccines in HSV-1-seropositive and HSV-1-seronegative guinea pigs. J Infect Dis. Oct. 1, 2009;200(7):1088-95.*

Chiu YG, Bowers WJ, Lim ST, Ryan DA, Federoff HJ. Effects of herpes simplex virus amplicon transduction on murine dendritic cells. Hum Gene Ther. May 2009;20(5):442-52.*

NCBI GenBank Reference Sequence: NP_044494.1; DNA packaging tegument protein UL25 [Human herpesvirus 2]. Sub. Aug. 1, 2000; last revision Apr. 23, 2010.*

NCBI GenBank Reference Sequence: NP_044536.1; envelope glycoprotein D [Human herpesvirus 2]. Sub. Aug. 1, 2000; last revision Apr. 23, 2010.*

Corey L, Laing KJ, Magaret AS, Mueller DE, Zhao L, Johnston C, De Rosa SC, Koelle DM, Wald A. DNA packaging tegument protein [Human herpesvirus 2]. GenBank Acc. No: ADG01878.1. Updated May 3, 2010.*

Boukhvalova et al., J. Virology, 2015, 89(19):9825-9840.*

Jeffrey Cohen, Laboratory of Infectious Diseases, NIH, Jun. 20, 2012, slide presentation, 16 slides, plus an additional page showing evidence of date; slides available from http://www.globe-network.org/sites/default/files/documents/public/en/resources/conferences/2012/herpes-virus-infection-and-immunity/animal-models-for-hsv.pdf.*

Ali et al., Characterization of an essential HSV-1 protein encoded by the UL25 gene reported to be involved in virus penetration and capsid assembly, Virol., 216(1):278-83 (1996).

Awasthi et al., Better neutralization of herpes simplex virus type 1 (HSV-1) than HSV-2 by antibody from recipients of GlaxoSmithKline HSV-2 glycoprotein D2 subunit vaccine, J. Infect. Dis., 210(4):571-5 (2014).

Awasthi et al., Immunization with a vaccine combining herpes simplex virus 2 (HSV-2) glycoprotein C (gC) and gD subunits improves the protection of dorsal root ganglia in mice and reduces the frequency of recurrent vaginal shedding of HSV-2 DNA in guinea pigs compared to immunization with gD alone, J. Virol., 85(20):10472-86 (2011).

Awasthi et al., Status of prophylactic and therapeutic genital herpes vaccines, Curr. Opin. Virol., 6:6-12 (2014).

Belshe et al., Efficacy results of a trial of a herpes simplex vaccine, N. Engl. J. Med., 366(1):34-43 (2012).

Bernstein et al., Safety and immunogenicity of glycoprotein D-adjuvant genital herpes vaccine, Clin. Infect. Dis., 40(9):1271-81 (2005).

Berstein et al., Potent adjuvant activity of cationic liposome-DNA complexes for genital herpes vaccines, Clin. Vacc. Immunol., 16(5):699-705 (2009).

Blaho et al., An amino acid sequence shared by the herpes simplex virus 1 alpha regulatory proteins 0, 4, 22, and 27 predicts the nucleotidylylation of the UL21, UL31, UL47, and UL49 gene products, J. Biol. Chem., 269(26):17401-10 (1994).

Bowman et al., Structural characterization of the UL25 DNA-packaging protein from herpes simplex virus type 1, J. Virol., 80(5):2309-17 (2006).

Cattamanchi et al., Phase I study of a herpes simplex virus type 2 (HSV-2) DNA vaccine administered to healthy, HSV-2-seronegative adults by a needle-free injection system, Clin. Vaccine Immunol., 15(11):1638-43 (2008).

Chentoufi et al., HLA-A* Restricted CD*+ Cytotoxic T Lymphocyte Epitopes Identified From Herpes Simplex Virus Glycoprotein D, J. Immunol., 180:426-37 (2008).

Cockrell et al., Role of the UL25 protein in herpes simplex virus DNA encapsidation, J. Virol., 83(1):47-57 (2009).

Cohen et al., Structural analysis of the capsid polypeptides of herpes simplex virus types 1 and 2, J. Virol., 34:521-31 (1980).

Coler et al., Development and characterization of synthetic glucopyranosyl lipid adjuvant system as a vaccine adjuvant, Plos One, 6(1):E16333 (2011).

Corey et al., Recombinant glycoprotein vaccine for the prevention of genital HSV-2 infection: two randomized controlled trials. Chiron HSV Vaccine Study Group, JAMA, 282(4):331-40 (1999).

Desai et al., Second site mutations in the N-terminus of the major capsid protein (VP5) overcome a block at the maturation cleavage site of the capsid scaffold proteins of herpes simplex virus type 1, Virol., 261(2):357-66 (1999).

Dolan et al., The genome sequence herpes simplex virus type 2, J. Virol., 72(3):2010-21 (1998).

Gebhardt et al., Memory T cells in nonlymphoid tissue that provide enhanced local immunity during infection with herpes simplex virus, Nat. Immunol., 10(5):524-30 (2009).

Hosken et al., Diversity of the CD8+ T-cell response to herpes simplex virus type 2 proteins among persons with genital herpes, J. Virol., 80(11):5509-15 (2006).

Hosken, Development of a therapeutic vaccine for HSV-2, Vaccine, 2395-8 (2005).

Huang et al., The herpes simplex virus type 1 major capsid protein (VP5-UL19) promoter contains two cis-acting elements influencing late expression, J. Virol., 68(9):5738-47 (1994).

Kask et al., DNA vaccine delivery by densely-packed and short microprojection arrays to skin protects against vaginal HSV-2 challenge, Vaccine, 28:7483-91 (2010).

Khodai et al., Single and combination herpes simplex virus type 2 glycoprotein vaccines adjuvanted with CpG oligodeoxynucleotides or monophosphoryl lipid A exhibit differential immunity that is not correlated to protection in animal models, Clin. Vaccine Immunol., 18(10):1702-9 (2011).

Koelle et al., CD4 T-cell responses to herpes simplex virus type 2 major capsid protein VP5: comparison with responses to tegument and envelope glycoproteins, J. Virol., 74(23):11422-5 (2000).

Koelle et al., CD8 CTL from genital herpes simplex lesions: recognition of viral tegument and immediate early proteins and lysis of infected cutaneous cell, J. Immunol., 166(6):4049-58 (2001).

Koelle et al., Herpes simplex virus infection of human fibroblasts and keratinocytes inhibits recognition by cloned CD8+ cytotoxic T lymphocytes, J. Clin. Invest., 91(3):961-8 (1993).

Koelle et al., Immunodominance among herpes simplex virus-specific CD8 T cells expressing a tissue-specific homing receptor, Proc. Natl. Acad. Sci. USA, 100(22):12899-904 (2003).

Koelle et al., Phase I dose-escalation study of a monovalent heat shock protein 70-herpes simplex virus type 2 (HSV-2) peptide-based vaccine designed to prime or boost CD8 T-cell responses in HSV-naïve and HSV-2-infected subjects, Clin. Vaccine Immunol., 15(5):773-82 (2008).

Koelle et al., Recent progress in Herpes Simplex Virus Immunobiology and Vaccine Research, Clin. Microbiol. Rev., 16(1):96-113 (2003).

Koelle et al., Tegument-specific, virus-reactive CD4 T cells localize to the cornea in herpes simplex virus interstitial keratitis in humans, J. Virol., 74(23):10930-8 (2000).

Laing et al., Diversity in CD8(+) T cell function and epitope breadth among persons with genital herpes, J. Clin. Immunol., 30(5):703-722 (2010).

(56) References Cited

OTHER PUBLICATIONS

Langenberg et al., A recombinant glycoprotein vaccine for herpes simplex virus type 2: safety and immunogenicity, *Ann. Intern. Med.*, 122(12):889-98 (1995).
Long et al., Identification of novel virus-specific antigens by CD4+ and CD8+ T cells from asymptomatic HSV-2 seropositive and seronegative donors, *Virol.*, 464-5:296-311 (2014).
Morello et al., Immunization with herpes simplex virus 2 (HSV-2) genes plus inactivated HSV-2 is highly protective against acute and recurrent HSV-2 disease, *J. Virol.*, 85(7):3461-72 (2011).
Morello et al., Inactivated HSV-2 in MPL/alum adjuvant provides nearly complete protection against genital infection and shedding following long term challenge and rechallenge, *Vaccine*, 30(46):6541-50 (2012).
Muller et al., Herpes simplex virus type 2 tegument proteins contain subdominant T-cell epitopes detectable in BALB/c mice after DNA immunization and infection, *J. Gen. Virol.*, 90(Pt 5):1153-60 (2009).
Nishimura et al., Intraepithelial gammadelta T cells may bridge a gap between innate immunity and acquired immunity to herpes simplex virus type 2, *J. Virol.*, 78(9):4927-30 (2004).
Posavad et al., Detailed characterization of T cell responses to herpes simplex virus-2 in immune seronegative persons, *J. Immunol.*, 184(6):3250-9 (2010).
Posavad et al., Development of an interferon-gamma ELISPOT assay to detect human T cell responses to HSV-2, *Vaccine*, 29(40):7058-66 (2011).
Preston et al., The UL25 gene product of herpes simplex virus type 1 is involved in uncoating of the viral genome, *J. Virol.*, 82(13):6654-66 (2008).
Rajcani et al., Developments in herpes simplex virus vaccines: old problems and new challenges, *Folia Microbiol.*, 51(2):67-85 (2006).
Roth et al., HSV-2 vaccine: current state and insights into development of a vaccine that targets genital mucosal protection, *Microb. Pathog.*, 59:45-54 (2012).
Samandary et al., Associations of HLA-A, HLA-B and HLA-C alleles frequency with prevalence of herpes simplex virus infections and diseases across global populations: implication for the development of an universal CD8+ T-cell epitope-based vaccine, *Hum. Immunol.*, 75(8):715-29 (2014).
Sciortino et al., Of the three tegument proteins that package mRNA in herpes simplex virions, one (VP22) transports the mRNA to uninfected cells for expression prior to viral infection, *Proc. Natl. Acad. Sci. U.S.A.*, 99(12):8318-23 (2002).
Shlapobersky et al., Vaxfectin-adjuvanted plasmid DNA vaccine improves protection and immunogenicity in a murine model of genital herpes infection, *J. Gen. Virol.*, 9(Pt 6):1305-15 (2012).
Stanberry et al., Vaccination with recombinant herpes simplex virus glycoproteins: protection against initial and recurrent genital herpes. *J. Infect. Dis.*, 155:914-20 (1987).
Straus et al., Immunotherapy of recurrent genital herpes with recombinant herpes simplex virus type 2 glycoproteins D and B: results of a placebo-controlled vaccine trial, *J. Infect. Dis.*, 176(5):1129-34 (1997).
Tatman et al., Assembly of herpes simplex type 1 capsids using a panel of recombinant baculoviruses, *J. Gen. Virol.*, 75:1011-13 (1994).
Tigges et al., Human CD8+ herpes simplex virus-specific cytotoxic T-lymphocyte clones recognize diverse virion protein antigens, *J. Virol.*, 66(3):1622-34 (1992).
Tirabassi et al., A muscosal vaccination approach for herpes simplex virus type 2, *Vaccine*, 29:1090-8 (2011).
Verhagen et al., Nucleocytoplasmic shuttling of bovine herpesvirus 1 UL47 protein in infected cells, *J. Virol.*, 80(2):1059-63 (2006).
Wald et al., Safety and immunogenicity of long HSV-2 peptides complexed with rhHsc70 in HSV-2 seropositive persons, *Vaccine*, 29(47):8520-9 (2011).
Wang et al., The 2.2-kilobase latency-associated transcript of herpes simplex virus type 2 does not modulate viral replication, reactivation, or establishment of latency in transgenic mice, *J. Virol.*, 75(17):8166-72 (2001).
Zhang et al., A herpes simplex virus 2 (HSV-2) glycoprotein D-expressing nonreplicating dominant-negative HSV-2 virus vaccine is superior to a gD2 subunit vaccine against HSV-2 genital infection in guinea pigs, *PLoS one*, 9(6):e101373 (2014).
Zhu et al., Virus-specific CD8+ T cells accumulate near sensory nerve endings in genital skin during subclinical HSV-2 reactivation, *J. Exp. Med.*, 204(3):595-603 (2007).

\* cited by examiner

SEQUENCE LISTING

```
<160> NUMBER OF SEQ ID NOS: 17

<210> SEQ ID NO 1
<211> LENGTH: 904
<212> TYPE: PRT
<213> ORGANISM: Herpes Simplex Virus 2

<400> SEQUENCE: 1

Met Arg Gly Gly Gly Leu Ile Cys Ala Leu Val Val Gly Ala Leu Val
1               5                   10                  15

Ala Ala Val Ala Ser Ala Ala Pro Ala Ala Pro Ala Ala Pro Arg Ala
            20                  25                  30

Ser Gly Gly Val Ala Ala Thr Val Ala Ala Asn Gly Gly Pro Ala Ser
        35                  40                  45

Arg Pro Pro Pro Val Pro Ser Pro Ala Thr Thr Lys Ala Arg Lys Arg
    50                  55                  60

Lys Thr Lys Lys Pro Pro Lys Arg Pro Glu Ala Thr Pro Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
        115                 120                 125

Pro Thr Arg Pro Glu Gly Gln Asn Tyr Thr Glu Gly Ile Ala Val Val
    130                 135                 140
```

```
Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
            165                 170                 175

Phe Met Gly Ile Phe Glu Asp Arg Ala Pro Val Pro Phe Glu Glu Val
            180                 185                 190

Ile Asp Lys Ile Asn Thr Lys Gly Val Cys Arg Ser Thr Ala Lys Tyr
            195                 200                 205

Val Arg Asn Asn Met Glu Thr Thr Ala Phe His Arg Asp Asp His Glu
210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                245                 250                 255

Phe His Arg Tyr Gly Thr Thr Val Asn Cys Ile Val Glu Glu Val Asp
                260                 265                 270

Ala Arg Ser Val Tyr Pro Tyr Asp Glu Phe Val Leu Ala Thr Gly Asp
                275                 280                 285

Phe Val Tyr Met Ser Pro Phe Tyr Gly Tyr Arg Glu Gly Ser His Thr
290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
                340                 345                 350

Pro Lys Arg Pro Ala Val Cys Thr Met Thr Lys Trp Gln Glu Val Asp
                355                 360                 365

Glu Met Leu Arg Ala Glu Tyr Gly Gly Ser Phe Arg Phe Ser Ser Asp
370                 375                 380

Ala Ile Ser Thr Thr Phe Thr Thr Asn Leu Thr Glu Tyr Ser Leu Ser
385                 390                 395                 400

Arg Val Asp Leu Gly Asp Cys Ile Gly Arg Asp Ala Arg Glu Ala Ile
                405                 410                 415

Asp Arg Met Phe Ala Arg Lys Tyr Asn Ala Thr His Ile Lys Val Gly
                420                 425                 430

Gln Pro Gln Tyr Tyr Leu Ala Thr Gly Gly Phe Leu Ile Ala Tyr Gln
                435                 440                 445

Pro Leu Leu Ser Asn Thr Leu Ala Glu Leu Tyr Val Arg Glu Tyr Met
                450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
                485                 490                 495

Ser Ile Glu Phe Ala Arg Leu Gln Phe Thr Tyr Asn His Ile Gln Arg
                500                 505                 510

His Val Asn Asp Met Leu Gly Arg Ile Ala Val Ala Trp Cys Glu Leu
                515                 520                 525

Gln Asn His Glu Leu Thr Leu Trp Asn Glu Ala Arg Lys Leu Asn Pro
                530                 535                 540

Asn Ala Ile Ala Ser Ala Thr Val Gly Arg Arg Val Ser Ala Arg Met
545                 550                 555                 560
```

```
Leu Gly Asp Val Met Ala Val Ser Thr Cys Val Pro Val Ala Pro Asp
                565                 570                 575

Asn Val Ile Val Gln Asn Ser Met Arg Val Ser Ser Arg Pro Gly Thr
            580                 585                 590

Cys Tyr Ser Arg Pro Leu Val Ser Phe Arg Tyr Glu Asp Gln Gly Pro
        595                 600                 605

Leu Ile Glu Gly Gln Leu Gly Glu Asn Asn Glu Leu Arg Leu Thr Arg
    610                 615                 620

Asp Ala Leu Glu Pro Cys Thr Val Gly His Arg Arg Tyr Phe Ile Phe
625                 630                 635                 640

Gly Gly Gly Tyr Val Tyr Phe Glu Glu Tyr Ala Tyr Ser His Gln Leu
                645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Glu Val Tyr Thr Arg
        675                 680                 685

His Glu Ile Lys Asp Ser Gly Leu Leu Asp Tyr Thr Glu Val Gln Arg
    690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
        755                 760                 765

Ser Asn Pro Phe Gly Ala Leu Ala Val Gly Leu Leu Val Leu Ala Gly
    770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                805                 810                 815

Ser Asp Pro Gly Gly Val Gly Gly Glu Gly Glu Glu Gly Ala Glu Gly
            820                 825                 830

Gly Gly Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Arg
    850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                885                 890                 895

Glu Ala Gly Asp Glu Asp Glu Leu
            900

<210> SEQ ID NO 2
<211> LENGTH: 393
<212> TYPE: PRT
<213> ORGANISM: Herpes Simplex Virus 2

<400> SEQUENCE: 2

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30
```

```
Ser Leu Lys Met Ala Asp Pro Asn Arg Phe Arg Gly Lys Asn Leu Pro
         35                  40                  45

Val Leu Asp Gln Leu Thr Asp Pro Pro Gly Val Lys Arg Val Tyr His
 50                  55                  60

Ile Gln Pro Ser Leu Glu Asp Pro Phe Gln Pro Ser Ile Pro Ile
 65                  70                  75                  80

Thr Val Tyr Tyr Ala Val Leu Glu Arg Ala Cys Arg Ser Val Leu Leu
                 85                  90                  95

His Ala Pro Ser Glu Ala Pro Gln Ile Val Arg Gly Ala Ser Asp Glu
                100                 105                 110

Ala Arg Lys His Thr Tyr Asn Leu Thr Ile Ala Trp Tyr Arg Met Gly
            115                 120                 125

Asp Asn Cys Ala Ile Pro Ile Thr Val Met Glu Tyr Thr Glu Cys Pro
130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
370                 375                 380

Pro Pro Ser His Gln Pro Leu Phe Tyr
385                 390

<210> SEQ ID NO 3
<211> LENGTH: 306
<212> TYPE: PRT
<213> ORGANISM: Herpes Simplex Virus 2

<400> SEQUENCE: 3

Lys Tyr Ala Leu Ala Asp Pro Ser Leu Lys Met Ala Asp Pro Asn Arg
```

```
              1               5                  10                 15
    Phe Arg Gly Lys Asn Leu Pro Val Leu Asp Gln Leu Thr Asp Pro Pro
                     20                 25                 30

Gly Val Lys Arg Val Tyr His Ile Gln Pro Ser Leu Glu Asp Pro Phe
                     35                 40                 45

Gln Pro Pro Ser Ile Pro Ile Thr Val Tyr Tyr Ala Val Leu Glu Arg
                 50                 55                 60

Ala Cys Arg Ser Val Leu Leu His Ala Pro Ser Glu Ala Pro Gln Ile
    65                  70                 75                  80

Val Arg Gly Ala Ser Asp Glu Ala Arg Lys His Thr Tyr Asn Leu Thr
                     85                 90                  95

Ile Ala Trp Tyr Arg Met Gly Asp Asn Cys Ala Ile Pro Ile Thr Val
                    100                105                110

Met Glu Tyr Thr Glu Cys Pro Tyr Asn Lys Ser Leu Gly Val Cys Pro
                    115                120                125

Ile Arg Thr Gln Pro Arg Trp Ser Tyr Asp Ser Phe Ser Ala Val
                    130                135                140

Ser Glu Asp Asn Leu Gly Phe Leu Met His Ala Pro Ala Phe Glu Thr
    145                 150                155                160

Ala Gly Thr Tyr Leu Arg Leu Val Lys Ile Asn Asp Trp Thr Glu Ile
                    165                170                175

Thr Gln Phe Ile Leu Glu His Arg Ala Arg Ala Ser Cys Lys Tyr Ala
                    180                185                190

Leu Pro Leu Arg Ile Pro Pro Ala Ala Cys Leu Thr Ser Lys Ala Tyr
                    195                200                205

Gln Gln Gly Val Thr Val Asp Ser Ile Gly Met Leu Pro Arg Phe Ile
                    210                215                220

Pro Glu Asn Gln Arg Thr Val Ala Leu Tyr Ser Leu Lys Ile Ala Gly
    225                 230                235                240

Trp His Gly Pro Lys Pro Pro Tyr Thr Ser Thr Leu Leu Pro Pro Glu
                    245                250                255

Leu Ser Asp Thr Thr Asn Ala Thr Gln Pro Glu Leu Val Pro Glu Asp
                    260                265                270

Pro Glu Asp Ser Ala Leu Leu Glu Asp Pro Ala Gly Thr Val Ser Ser
                    275                280                285

Gln Ile Pro Pro Asn Trp His Ile Pro Ser Ile Gln Asp Val Ala Pro
                    290                295                300

His His
    305

<210> SEQ ID NO 4
<211> LENGTH: 1374
<212> TYPE: PRT
<213> ORGANISM: Herpes Simplex Virus 2

<400> SEQUENCE: 4

Met Ala Ala Pro Ala Arg Asp Pro Pro Gly Tyr Arg Tyr Ala Ala Ala
    1                5                  10                 15

Met Val Pro Thr Gly Ser Ile Leu Ser Thr Ile Glu Val Ala Ser His
                     20                 25                 30

Arg Arg Leu Phe Asp Phe Phe Ala Arg Val Arg Ser Asp Glu Asn Ser
                     35                 40                 45

Leu Tyr Asp Val Glu Phe Asp Ala Leu Leu Gly Ser Tyr Cys Asn Thr
                 50                 55                 60
```

-continued

```
Leu Ser Leu Val Arg Phe Leu Glu Leu Gly Leu Ser Val Ala Cys Val
 65                  70                  75                  80

Cys Thr Lys Phe Pro Glu Leu Ala Tyr Met Asn Glu Gly Arg Val Gln
                 85                  90                  95

Phe Glu Val His Gln Pro Leu Ile Ala Arg Asp Gly Pro His Pro Val
            100                 105                 110

Glu Gln Pro Val His Asn Tyr Met Thr Lys Val Ile Asp Arg Arg Ala
        115                 120                 125

Leu Asn Ala Ala Phe Ser Leu Ala Thr Glu Ala Ile Ala Leu Leu Thr
    130                 135                 140

Gly Glu Ala Leu Asp Gly Thr Gly Ile Ser Leu His Arg Gln Leu Arg
145                 150                 155                 160

Ala Ile Gln Gln Leu Ala Arg Asn Val Gln Ala Val Leu Gly Ala Phe
                165                 170                 175

Glu Arg Gly Thr Ala Asp Gln Met Leu His Val Leu Leu Glu Lys Ala
            180                 185                 190

Pro Pro Leu Ala Leu Leu Pro Met Gln Arg Tyr Leu Asp Asn Gly
        195                 200                 205

Arg Leu Ala Thr Arg Val Ala Arg Ala Thr Leu Val Ala Glu Leu Lys
210                 215                 220

Arg Ser Phe Cys Asp Thr Ser Phe Leu Gly Lys Ala Gly His Arg
225                 230                 235                 240

Arg Glu Ala Ile Glu Ala Trp Leu Val Asp Leu Thr Thr Ala Thr Gln
                245                 250                 255

Pro Ser Val Ala Val Pro Arg Leu Thr His Ala Asp Thr Arg Gly Arg
            260                 265                 270

Pro Val Asp Gly Val Leu Val Thr Thr Ala Ala Ile Lys Gln Arg Leu
        275                 280                 285

Leu Gln Ser Phe Leu Lys Val Glu Asp Thr Glu Ala Asp Val Pro Val
    290                 295                 300

Thr Tyr Gly Glu Met Val Leu Asn Gly Ala Asn Leu Val Thr Ala Leu
305                 310                 315                 320

Val Met Gly Lys Ala Val Arg Ser Leu Asp Asp Val Gly Arg His Leu
                325                 330                 335

Leu Glu Met Gln Glu Gln Leu Glu Ala Asn Arg Glu Thr Leu Asp
            340                 345                 350

Glu Leu Glu Ser Ala Pro Gln Thr Thr Arg Val Arg Ala Asp Leu Val
        355                 360                 365

Ala Ile Gly Asp Arg Leu Val Phe Leu Glu Ala Leu Glu Lys Arg Ile
    370                 375                 380

Tyr Ala Ala Thr Asn Val Pro Tyr Pro Leu Val Gly Ala Met Asp Leu
385                 390                 395                 400

Thr Phe Val Leu Pro Leu Gly Leu Phe Asn Pro Ala Met Glu Arg Phe
                405                 410                 415

Ala Ala His Ala Gly Asp Leu Val Pro Ala Pro Gly His Pro Glu Pro
            420                 425                 430

Arg Ala Phe Pro Pro Arg Gln Leu Phe Phe Trp Gly Lys Asp His Gln
        435                 440                 445

Val Leu Arg Leu Ser Met Glu Asn Ala Val Gly Thr Val Cys His Pro
    450                 455                 460

Ser Leu Met Asn Ile Asp Ala Ala Val Gly Gly Val Asn His Asp Pro
465                 470                 475                 480

Val Glu Ala Ala Asn Pro Tyr Gly Ala Tyr Val Ala Ala Pro Ala Gly
```

```
                485                 490                 495
Pro Gly Ala Asp Met Gln Gln Arg Phe Leu Asn Ala Trp Arg Gln Arg
            500                 505                 510
Leu Ala His Gly Arg Val Arg Trp Val Ala Glu Cys Gln Met Thr Ala
        515                 520                 525
Glu Gln Phe Met Gln Pro Asp Asn Ala Asn Leu Ala Leu Glu Leu His
    530                 535                 540
Pro Ala Phe Asp Phe Phe Ala Gly Val Ala Asp Val Glu Leu Pro Gly
545                 550                 555                 560
Gly Glu Val Pro Pro Ala Gly Pro Gly Ala Ile Gln Ala Thr Trp Arg
                565                 570                 575
Val Val Asn Gly Asn Leu Pro Leu Ala Leu Cys Pro Val Ala Phe Arg
            580                 585                 590
Asp Ala Arg Gly Leu Glu Leu Gly Val Gly Arg His Ala Met Ala Pro
        595                 600                 605
Ala Thr Ile Ala Ala Val Arg Gly Ala Phe Glu Asp Arg Ser Tyr Pro
    610                 615                 620
Ala Val Phe Tyr Leu Leu Gln Ala Ala Ile His Gly Ser Glu His Val
625                 630                 635                 640
Phe Cys Ala Leu Ala Arg Leu Val Thr Gln Cys Ile Thr Ser Tyr Trp
                645                 650                 655
Asn Asn Thr Arg Cys Ala Ala Phe Val Asn Asp Tyr Ser Leu Val Ser
            660                 665                 670
Tyr Ile Val Thr Tyr Leu Gly Gly Asp Leu Pro Glu Glu Cys Met Ala
        675                 680                 685
Val Tyr Arg Asp Leu Val Ala His Val Glu Ala Leu Ala Gln Leu Val
    690                 695                 700
Asp Asp Phe Thr Leu Pro Gly Pro Glu Leu Gly Gly Gln Ala Gln Ala
705                 710                 715                 720
Glu Leu Asn His Leu Met Arg Asp Pro Ala Leu Leu Pro Pro Leu Val
                725                 730                 735
Trp Asp Cys Asp Gly Leu Met Arg His Ala Ala Leu Asp Arg His Arg
            740                 745                 750
Asp Cys Arg Ile Asp Ala Gly Gly His Glu Pro Val Tyr Ala Ala Ala
        755                 760                 765
Cys Asn Val Ala Thr Ala Asp Phe Asn Arg Asn Asp Gly Arg Leu Leu
    770                 775                 780
His Asn Thr Gln Ala Arg Ala Ala Asp Ala Ala Asp Arg Pro His
785                 790                 795                 800
Arg Pro Ala Asp Trp Thr Val His His Lys Ile Tyr Tyr Val Leu
                805                 810                 815
Val Pro Ala Phe Ser Arg Gly Arg Cys Cys Thr Ala Gly Val Arg Phe
            820                 825                 830
Asp Arg Val Tyr Ala Thr Leu Gln Asn Met Val Val Pro Glu Ile Ala
        835                 840                 845
Pro Gly Glu Glu Cys Pro Ser Asp Pro Val Thr Asp Pro Ala His Pro
    850                 855                 860
Leu His Pro Ala Asn Leu Val Ala Asn Thr Val Asn Ala Met Phe His
865                 870                 875                 880
Asn Gly Arg Val Val Val Asp Gly Pro Ala Met Leu Thr Leu Gln Val
                885                 890                 895
Leu Ala His Asn Met Ala Glu Arg Thr Thr Ala Leu Leu Cys Ser Ala
            900                 905                 910
```

```
Ala Pro Asp Ala Gly Ala Asn Thr Ala Ser Thr Ala Asn Met Arg Ile
        915                 920                 925

Phe Asp Gly Ala Leu His Ala Gly Val Leu Leu Met Ala Pro Gln His
    930                 935                 940

Leu Asp His Thr Ile Gln Asn Gly Glu Tyr Phe Tyr Val Leu Pro Val
945                 950                 955                 960

His Ala Leu Phe Ala Gly Ala Asp His Val Ala Asn Ala Pro Asn Phe
                965                 970                 975

Pro Pro Ala Leu Arg Asp Leu Ala Arg His Val Pro Leu Val Pro Pro
            980                 985                 990

Ala Leu Gly Ala Asn Tyr Phe Ser Ser Ile Arg Gln Pro Val Val Gln
        995                 1000                1005

His Ala Arg Glu Ser Ala Ala Gly Glu Asn Ala Leu Thr Tyr Ala
    1010                1015                1020

Leu Met Ala Gly Tyr Phe Lys Met Ser Pro Val Ala Leu Tyr His
    1025                1030                1035

Gln Leu Lys Thr Gly Leu His Pro Gly Phe Gly Phe Thr Val Val
    1040                1045                1050

Arg Gln Asp Arg Phe Val Thr Glu Asn Val Leu Phe Ser Glu Arg
    1055                1060                1065

Ala Ser Glu Ala Tyr Phe Leu Gly Gln Leu Gln Val Ala Arg His
    1070                1075                1080

Glu Thr Gly Gly Gly Val Ser Phe Thr Leu Thr Gln Pro Arg Gly
    1085                1090                1095

Asn Val Asp Leu Gly Val Gly Tyr Thr Ala Val Ala Ala Thr Ala
    1100                1105                1110

Thr Val Arg Asn Pro Val Thr Asp Met Gly Asn Leu Pro Gln Asn
    1115                1120                1125

Phe Tyr Leu Gly Arg Gly Ala Pro Pro Leu Leu Asp Asn Ala Ala
    1130                1135                1140

Ala Val Tyr Leu Arg Asn Ala Val Val Ala Gly Asn Arg Leu Gly
    1145                1150                1155

Pro Ala Gln Pro Leu Pro Val Phe Gly Cys Ala Gln Val Pro Arg
    1160                1165                1170

Arg Ala Gly Met Asp His Gly Gln Asp Ala Val Cys Glu Phe Ile
    1175                1180                1185

Ala Thr Pro Val Ala Thr Asp Ile Asn Tyr Phe Arg Arg Pro Cys
    1190                1195                1200

Asn Pro Arg Gly Arg Ala Ala Gly Gly Val Tyr Ala Gly Asp Lys
    1205                1210                1215

Glu Gly Asp Val Ile Ala Leu Met Tyr Asp His Gly Gln Ser Asp
    1220                1225                1230

Pro Ala Arg Pro Phe Ala Ala Thr Ala Asn Pro Trp Ala Ser Gln
    1235                1240                1245

Arg Phe Ser Tyr Gly Asp Leu Leu Tyr Asn Gly Ala Tyr His Leu
    1250                1255                1260

Asn Gly Ala Ser Pro Val Leu Ser Pro Cys Phe Lys Phe Phe Thr
    1265                1270                1275

Ala Ala Asp Ile Thr Ala Lys His Arg Cys Leu Glu Arg Leu Ile
    1280                1285                1290

Val Glu Thr Gly Ser Ala Val Ser Thr Ala Thr Ala Ala Ser Asp
    1295                1300                1305
```

```
Val Gln Phe Lys Arg Pro Gly Cys Arg Glu Leu Val Glu Asp
    1310            1315                1320

Pro Cys Gly Leu Phe Gln Glu Ala Tyr Pro Ile Thr Cys Ala Ser
    1325                1330                1335

Asp Pro Ala Leu Leu Arg Ser Ala Arg Asp Gly Glu Ala His Ala
    1340                1345                1350

Arg Glu Thr His Phe Thr Gln Tyr Leu Ile Tyr Asp Ala Ser Pro
    1355                1360                1365

Leu Lys Gly Leu Ser Leu
    1370

<210> SEQ ID NO 5
<211> LENGTH: 585
<212> TYPE: PRT
<213> ORGANISM: Herpes Simplex Virus 2

<400> SEQUENCE: 5

Met Asp Pro Tyr Tyr Pro Phe Asp Ala Leu Asp Val Trp Glu His Arg
1               5                   10                  15

Arg Phe Ile Val Ala Asp Ser Arg Ser Phe Ile Thr Pro Glu Phe Pro
                20                  25                  30

Arg Asp Phe Trp Met Leu Pro Val Phe Asn Ile Pro Arg Glu Thr Ala
            35                  40                  45

Ala Glu Arg Ala Ala Val Leu Gln Ala Gln Arg Thr Ala Ala Ala
        50                  55                  60

Ala Leu Glu Asn Ala Ala Leu Gln Ala Ala Glu Leu Pro Val Asp Ile
65                  70                  75                  80

Glu Arg Arg Ile Arg Pro Ile Glu Gln Gln Val His His Ile Ala Asp
                85                  90                  95

Ala Leu Glu Ala Leu Glu Thr Ala Ala Ala Ala Glu Glu Ala Asp
            100                 105                 110

Ala Ala Arg Asp Ala Glu Ala Arg Gly Glu Gly Ala Ala Asp Gly Ala
        115                 120                 125

Ala Pro Ser Pro Thr Ala Gly Pro Ala Ala Glu Met Glu Val Gln
    130                 135                 140

Ile Val Arg Asn Asp Pro Pro Leu Arg Tyr Asp Thr Asn Leu Pro Val
145                 150                 155                 160

Asp Leu Leu His Met Val Tyr Ala Gly Arg Gly Ala Ala Gly Ser Ser
                165                 170                 175

Gly Val Val Phe Gly Thr Trp Tyr Arg Thr Ile Gln Glu Arg Thr Ile
            180                 185                 190

Ala Asp Phe Pro Leu Thr Thr Arg Ser Ala Asp Phe Arg Asp Gly Arg
        195                 200                 205

Met Ser Lys Thr Phe Met Thr Ala Leu Val Leu Leu Gln Ser Cys
    210                 215                 220

Gly Arg Leu Tyr Val Gly Gln Arg His Tyr Ser Ala Phe Glu Cys Ala
225                 230                 235                 240

Val Leu Cys Leu Tyr Leu Leu Tyr Arg Thr Thr His Glu Ser Ser Pro
                245                 250                 255

Asp Arg Asp Arg Ala Pro Val Ala Phe Gly Asp Leu Leu Ala Arg Leu
            260                 265                 270

Pro Arg Tyr Leu Ala Arg Leu Ala Ala Val Ile Gly Asp Glu Ser Gly
        275                 280                 285

Arg Pro Gln Tyr Arg Tyr Arg Asp Asp Lys Leu Pro Lys Ala Gln Phe
    290                 295                 300
```

```
Ala Ala Ala Gly Gly Arg Tyr Glu His Gly Ala Leu Ala Thr His Val
305                 310                 315                 320

Val Ile Ala Thr Leu Val Arg His Gly Val Leu Pro Ala Ala Pro Gly
            325                 330                 335

Asp Val Pro Arg Asp Thr Ser Thr Arg Val Asn Pro Asp Val Ala
        340                 345                 350

His Arg Asp Asp Val Asn Arg Ala Ala Ala Phe Leu Ala Arg Gly
        355                 360                 365

His Asn Leu Phe Leu Trp Glu Asp Gln Thr Leu Leu Arg Ala Thr Ala
370                 375                 380

Asn Thr Ile Thr Ala Leu Ala Val Leu Arg Arg Leu Leu Ala Asn Gly
385                 390                 395                 400

Asn Val Tyr Ala Asp Arg Leu Asp Asn Arg Leu Gln Leu Gly Met Leu
            405                 410                 415

Ile Pro Gly Ala Val Pro Ala Glu Ala Ile Ala Arg Gly Ala Ser Gly
        420                 425                 430

Leu Asp Ser Gly Ala Ile Lys Ser Gly Asp Asn Leu Glu Ala Leu
        435                 440                 445

Cys Val Asn Tyr Val Leu Pro Leu Tyr Gln Ala Asp Pro Thr Val Glu
450                 455                 460

Leu Thr Gln Leu Phe Pro Gly Leu Ala Ala Leu Cys Leu Asp Ala Gln
465                 470                 475                 480

Ala Gly Arg Pro Leu Ala Ser Thr Arg Arg Val Val Asp Met Ser Ser
            485                 490                 495

Gly Ala Arg Gln Ala Ala Leu Val Arg Leu Thr Ala Leu Glu Leu Ile
        500                 505                 510

Asn Arg Thr Arg Thr Asn Thr Thr Pro Val Gly Glu Ile Ile Asn Ala
        515                 520                 525

His Asp Ala Leu Gly Ile Gln Tyr Glu Gln Gly Leu Gly Leu Leu Ala
        530                 535                 540

Gln Gln Ala Arg Ile Gly Leu Ala Ser Asn Ala Lys Arg Phe Ala Thr
545                 550                 555                 560

Phe Asn Val Gly Ser Asp Tyr Asp Leu Leu Tyr Phe Leu Cys Leu Gly
            565                 570                 575

Phe Ile Pro Gln Tyr Leu Ser Val Ala
            580                 585

<210> SEQ ID NO 6
<211> LENGTH: 696
<212> TYPE: PRT
<213> ORGANISM: Herpes Simplex Virus 2

<400> SEQUENCE: 6

Met Ser Val Arg Gly His Ala Val Arg Arg Arg Ala Ser Thr Arg
1               5                   10                  15

Ser His Ala Pro Ser Ala His Arg Ala Asp Ser Pro Val Glu Asp Glu
            20                  25                  30

Pro Glu Gly Gly Gly Gly Gly Leu Met Gly Tyr Leu Arg Ala Val Phe
        35                  40                  45

Asn Val Asp Asp Asp Ser Glu Val Glu Ala Ala Gly Glu Met Ala Ser
    50                  55                  60

Glu Glu Pro Pro Pro Arg Arg Arg Glu Ala Arg Gly His Pro Gly
65                  70                  75                  80

Ser Arg Arg Ala Ser Glu Ala Arg Ala Ala Ala Pro Pro Arg Arg Ala
```

```
                            85                  90                  95
        Ser Phe Pro Arg Pro Arg Ser Val Thr Ala Arg Ser Gln Ser Val Arg
                        100                 105                 110

Gly Arg Arg Asp Ser Ala Ile Thr Arg Ala Pro Arg Gly Gly Tyr Leu
                        115                 120                 125

Gly Pro Met Asp Pro Arg Asp Val Leu Gly Arg Val Gly Gly Ser Arg
                    130                 135                 140

Val Val Pro Ser Pro Leu Phe Leu Asp Glu Leu Ser Tyr Glu Glu Asp
        145                 150                 155                 160

Asp Tyr Pro Ala Ala Val Ala His Asp Gly Ala Gly Ala Arg Pro
                        165                 170                 175

Pro Ala Thr Val Glu Ile Leu Ala Gly Arg Val Ser Gly Pro Glu Leu
                        180                 185                 190

Gln Ala Ala Phe Pro Leu Asp Arg Leu Thr Pro Arg Val Ala Ala Trp
                        195                 200                 205

Asp Glu Ser Val Arg Ser Ala Leu Ala Leu Gly His Pro Ala Gly Phe
                    210                 215                 220

Tyr Pro Cys Pro Asp Ser Ala Phe Gly Leu Ser Arg Val Gly Val Met
        225                 230                 235                 240

His Phe Ala Ser Pro Ala Asp Pro Lys Val Phe Phe Arg Gln Thr Leu
                        245                 250                 255

Gln Gln Gly Glu Ala Leu Ala Trp Tyr Val Thr Gly Asp Ala Ile Leu
                    260                 265                 270

Asp Leu Thr Asp Arg Arg Ala Lys Thr Ser Pro Ser Arg Ala Met Gly
                    275                 280                 285

Phe Leu Val Asp Ala Ile Val Arg Val Ala Ile Asn Gly Trp Val Cys
        290                 295                 300

Gly Thr Arg Leu His Thr Glu Gly Arg Gly Ser Glu Leu Asp Asp Arg
        305                 310                 315                 320

Ala Ala Glu Leu Arg Arg Gln Phe Ala Ser Leu Thr Ala Leu Arg Pro
                        325                 330                 335

Val Gly Ala Ala Ala Val Pro Leu Leu Ser Ala Gly Gly Ala Ala Pro
                    340                 345                 350

Pro His Pro Gly Pro Asp Ala Ala Val Phe Arg Ser Ser Leu Gly Ser
                    355                 360                 365

Leu Leu Tyr Trp Pro Gly Val Arg Ala Leu Leu Gly Arg Asp Cys Arg
                    370                 375                 380

Val Ala Ala Arg Tyr Ala Gly Arg Met Thr Tyr Ile Ala Thr Gly Ala
        385                 390                 395                 400

Leu Leu Ala Arg Phe Asn Pro Gly Ala Val Lys Cys Val Leu Pro Arg
                        405                 410                 415

Glu Ala Ala Phe Ala Gly Arg Val Leu Asp Val Leu Ala Val Leu Ala
                        420                 425                 430

Glu Gln Thr Val Gln Trp Leu Ser Val Val Gly Ala Arg Leu His
                    435                 440                 445

Pro His Ser Ala His Pro Ala Phe Asp Val Glu Gln Glu Ala Leu
                    450                 455                 460

Phe Arg Ala Leu Pro Leu Gly Ser Pro Gly Val Val Ala Ala Glu His
        465                 470                 475                 480

Glu Ala Leu Gly Asp Thr Ala Ala Arg Arg Leu Leu Ala Thr Ser Gly
                        485                 490                 495

Leu Asn Ala Val Leu Gly Ala Ala Val Tyr Ala Leu His Thr Ala Leu
                    500                 505                 510
```

```
Ala Thr Val Thr Leu Lys Tyr Ala Leu Ala Cys Gly Asp Ala Arg Arg
            515                 520                 525

Arg Arg Asp Asp Ala Ala Ala Arg Ala Val Leu Ala Thr Gly Leu
530                 535                 540

Ile Leu Gln Arg Leu Leu Gly Leu Ala Asp Thr Val Ala Cys Val
545                 550                 555                 560

Ala Leu Ala Ala Phe Asp Gly Gly Ser Thr Ala Pro Glu Val Gly Thr
                565                 570                 575

Tyr Thr Pro Leu Arg Tyr Ala Cys Val Leu Arg Ala Thr Gln Pro Leu
                580                 585                 590

Tyr Ala Arg Thr Thr Pro Ala Lys Phe Trp Ala Asp Val Arg Ala Ala
                595                 600                 605

Ala Glu His Val Asp Leu Arg Pro Ala Ser Ser Ala Pro Arg Ala Pro
            610                 615                 620

Val Ser Gly Thr Ala Asp Pro Ala Phe Leu Leu Glu Asp Leu Ala Ala
625                 630                 635                 640

Phe Pro Pro Ala Pro Leu Asn Ser Glu Ser Val Leu Gly Pro Arg Val
                645                 650                 655

Arg Val Val Asp Ile Met Ala Gln Phe Arg Lys Leu Leu Met Gly Asp
            660                 665                 670

Glu Glu Thr Ala Ala Leu Arg Ala His Val Ser Gly Arg Arg Ala Thr
                675                 680                 685

Gly Leu Gly Gly Pro Pro Arg Pro
            690                 695

<210> SEQ ID NO 7
<211> LENGTH: 15
<212> TYPE: PRT
<213> ORGANISM: Herpes simplex virus 2

<400> SEQUENCE: 7

Gln Pro Arg Trp Ser Tyr Tyr Asp Ser Phe Ser Ala Val Ser Glu
1               5                   10                  15

<210> SEQ ID NO 8
<211> LENGTH: 15
<212> TYPE: PRT
<213> ORGANISM: Herpes Simplex Virus 2

<400> SEQUENCE: 8

Ser Gln Ile Pro Pro Asn Trp His Ile Pro Ser Ile Gln Asp Val
1               5                   10                  15

<210> SEQ ID NO 9
<211> LENGTH: 15
<212> TYPE: PRT
<213> ORGANISM: Herpes Simplex Virus 2

<400> SEQUENCE: 9

Asn Tyr Phe Ser Ser Ile Arg Gln Pro Val Val Gln His Ala Arg
1               5                   10                  15

<210> SEQ ID NO 10
<211> LENGTH: 15
<212> TYPE: PRT
<213> ORGANISM: Herpes Simplex Virus 2

<400> SEQUENCE: 10

Cys Glu Phe Ile Ala Thr Pro Val Ala Thr Asp Ile Asn Tyr Phe
```

-continued

```
<210> SEQ ID NO 11
<211> LENGTH: 15
<212> TYPE: PRT
<213> ORGANISM: Herpes Simplex Virus 2

<400> SEQUENCE: 11

Met Asp Pro Tyr Tyr Pro Phe Asp Ala Leu Asp Val Trp Glu His
1               5                   10                  15

<210> SEQ ID NO 12
<211> LENGTH: 604
<212> TYPE: PRT
<213> ORGANISM: Herpes Simplex Virus 2

<400> SEQUENCE: 12

Arg Leu Ser Met Glu Asn Ala Val Gly Thr Val Cys His Pro Ser Leu
1               5                   10                  15

Met Asn Ile Asp Ala Ala Val Gly Gly Val Asn His Asp Pro Val Glu
            20                  25                  30

Ala Ala Asn Pro Tyr Gly Ala Tyr Val Ala Pro Ala Gly Pro Gly
        35                  40                  45

Ala Asp Met Gln Gln Arg Phe Leu Asn Ala Trp Arg Gln Arg Leu Ala
    50                  55                  60

His Gly Arg Val Arg Trp Val Ala Glu Cys Gln Met Thr Ala Glu Gln
65                  70                  75                  80

Phe Met Gln Pro Asp Asn Ala Asn Leu Ala Leu Glu Leu His Pro Ala
                85                  90                  95

Phe Asp Phe Phe Ala Gly Val Ala Asp Val Glu Leu Pro Gly Gly Glu
            100                 105                 110

Val Pro Pro Ala Gly Pro Gly Ala Ile Gln Ala Thr Trp Arg Val Val
        115                 120                 125

Asn Gly Asn Leu Pro Leu Ala Leu Cys Pro Val Ala Phe Arg Asp Ala
    130                 135                 140

Arg Gly Leu Glu Leu Gly Val Gly Arg His Ala Met Ala Pro Ala Thr
145                 150                 155                 160

Ile Ala Ala Val Arg Gly Ala Phe Glu Asp Arg Ser Tyr Pro Ala Val
                165                 170                 175

Phe Tyr Leu Leu Gln Ala Ala Ile His Gly Asn Glu His Val Phe Cys
            180                 185                 190

Ala Leu Ala Arg Leu Val Thr Gln Cys Ile Thr Ser Tyr Trp Asn Asn
        195                 200                 205

Thr Arg Cys Ala Ala Phe Val Asn Asp Tyr Ser Leu Val Ser Tyr Ile
    210                 215                 220

Val Thr Tyr Leu Gly Gly Asp Leu Pro Glu Glu Cys Met Ala Val Tyr
225                 230                 235                 240

Arg Asp Leu Val Ala His Val Glu Ala Leu Ala Gln Leu Val Asp Asp
                245                 250                 255

Phe Thr Leu Pro Gly Pro Glu Leu Gly Gly Gln Ala Gln Ala Glu Leu
            260                 265                 270

Asn His Leu Met Arg Asp Pro Ala Leu Leu Pro Pro Leu Val Trp Asp
        275                 280                 285

Cys Asp Gly Leu Met Arg His Ala Ala Leu Asp Arg His Arg Asp Cys
    290                 295                 300

Arg Ile Asp Ala Gly Gly His Glu Pro Val Tyr Ala Ala Ala Cys Asn
```

```
                305                 310                 315                 320
Val Ala Thr Ala Asp Phe Asn Arg Asn Asp Gly Arg Leu Leu His Asn
                    325                 330                 335

Thr Gln Ala Arg Ala Ala Asp Ala Ala Asp Arg Pro His Arg Pro
                340                 345                 350

Ala Asp Trp Thr Val His His Lys Ile Tyr Tyr Val Leu Val Pro
                    355                 360                 365

Ala Phe Ser Arg Gly Arg Cys Cys Thr Ala Gly Val Arg Phe Asp Arg
                370                 375                 380

Val Tyr Ala Thr Leu Gln Asn Met Val Val Pro Glu Ile Ala Pro Gly
385                 390                 395                 400

Glu Glu Cys Pro Ser Asp Pro Val Thr Asp Pro Ala His Pro Leu His
                405                 410                 415

Pro Ala Asn Leu Val Ala Asn Thr Val Lys Arg Met Phe His Asn Gly
                420                 425                 430

Arg Val Val Val Asp Gly Pro Ala Met Leu Thr Leu Gln Val Leu Ala
                435                 440                 445

His Asn Met Ala Glu Arg Thr Thr Ala Leu Leu Cys Ser Ala Ala Pro
        450                 455                 460

Asp Ala Gly Ala Asn Thr Ala Ser Thr Ala Asn Met Arg Ile Phe Asp
465                 470                 475                 480

Gly Ala Leu His Ala Gly Val Leu Leu Met Ala Pro Gln His Leu Asp
                    485                 490                 495

His Thr Ile Gln Asn Gly Glu Tyr Phe Tyr Val Leu Pro Val His Ala
                500                 505                 510

Leu Phe Ala Gly Ala Asp His Val Ala Asn Ala Pro Asn Phe Pro Pro
        515                 520                 525

Ala Leu Arg Asp Leu Ala Arg Asp Val Pro Leu Val Pro Pro Ala Leu
                530                 535                 540

Gly Ala Asn Tyr Phe Ser Ser Ile Arg Gln Pro Val Val Gln His Ala
545                 550                 555                 560

Arg Glu Ser Ala Ala Gly Glu Asn Ala Leu Thr Tyr Ala Leu Met Ala
                    565                 570                 575

Gly Tyr Phe Lys Met Ser Pro Val Ala Leu Tyr His Gln Leu Lys Thr
                580                 585                 590

Gly Leu His Pro Gly Phe Gly Phe Thr Val Val Arg
            595                 600

<210> SEQ ID NO 13
<211> LENGTH: 683
<212> TYPE: DNA
<213> ORGANISM: Human immunodeficiency virus type 1

<400> SEQUENCE: 13
cctagaaaaa catggagcaa tcacaagtag caatacagca gctaccaatg ctgattgtgc        60
ctggctagaa gcacaagagg aggaggaggt gggttttcca gtcacacctc aggtaccttt       120
aagaccaatg acttacaagg cagctgtaga tcttagccac tttttaaaag aaaaggggg        180 actggaaggg ctaattcact cccaacgaag acaagatatc cttgatctgt ggatctacca       240
cacacaaggc tacttccctg attggcagaa ctacacacca gggccaggga tcagatatcc       300
actgaccttt ggatggtgct acaagctagt accagttgag caagagaagg tagaagaagc       360
caatgaagga gagaacaccc gcttgttaca ccctgtgagc ctgcatggga tggatgaccc       420
ggagagagaa gtattagagt ggaggtttga cagccgccta gcatttcatc acatggcccg       480
```

```
agagctgcat ccggactgta ctgggtctct ctggttagac cagatctgag cctgggagct    540
ctctggctaa ctagggaacc cactgcttaa gcctcaataa agcttgcctt gagtgcttca    600
agtagtgtgt gcccgtctgt tgtgtgactc tggtaactag agatccctca gaccctttta    660
gtcagtgtgg aaaatctcta gca                                            683

<210> SEQ ID NO 14
<211> LENGTH: 416
<212> TYPE: DNA
<213> ORGANISM: Human immunodeficiency virus type 1

<400> SEQUENCE: 14
cctagaaaaa catggagcaa tcacaagtag caatacagca gctaccaatg ctgattgtgc     60
ctggctagaa gcacaagagg aggaggaggt gggttttcca gtcacacctc aggtaccttt    120
aagaccaatg acttacaagg cagctgtaga tcttagccac ttttaaaag aaaaggggggg    180 actggaaggg ctaattcact cccaacgaag acaagatctg cttttttgcct gtactgggtc    240 tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagacccct tagtcagtg tggaaaatct ctagca         416

<210> SEQ ID NO 15
<211> LENGTH: 401
<212> TYPE: DNA
<213> ORGANISM: Human immunodeficiency virus type 1

<400> SEQUENCE: 15
cctagaaaaa catggagcaa tcacaagtag caatacagca gctaccaatg ctgattgtgc     60
ctggctagaa gcacaagagg aggaggaggt gggttttcca gtcacacctc aggtaccttt    120
aagaccaatg acttacaagg cagctgtaga tcttagccac ttttactgg aagggctaat    180 tcactcccaa cgaagacaag atctgctttt tgcctgtact gggtctctct ggttagacca    240
gatctgagcc tgggagctct ctggctaact agggaaccca ctgcttaagc ctcaataaag    300
cttgccttga gtgcttcaag tagtgtgtgc ccgtctgttg tgtgactctg gtaactagag    360
atccctcaga cccttttagt cagtgtggaa aatctctagc a                        401

<210> SEQ ID NO 16
<211> LENGTH: 4
<212> TYPE: PRT
<213> ORGANISM: HSV-2 fragment

<400> SEQUENCE: 16

Cys Ala Lys Tyr
1

<210> SEQ ID NO 17
<211> LENGTH: 4
<212> TYPE: PRT
<213> ORGANISM: HSV-2 modified fragment

<400> SEQUENCE: 17

Gly Leu Ala Val
1
```

VACCINES FOR HSV-2

CROSS REFERENCE TO RELATED APPLICATIONS

This application claims the benefit under 35 U.S.C. §119(e) of U.S. Provisional Patent Application Nos. 61/647,764, filed May 16, 2012, 61/679,387, filed Aug. 3, 2012, and 61/714,158, filed Oct. 15, 2012, all of which are incorporated herein by reference in their entirety.

REFERENCE TO SEQUENCE LISTING

The sequence listing of this patent application is provided separately in a file named "47733_SeqListing.txt". The content of this file, which was created on 16 May 2013, and consists of 45,969 bytes, is incorporated in its entirety.

TECHNICAL FIELD

Vaccines for herpes simplex virus-2 infection and related methods and compositions.

BACKGROUND

HSV-2 (herpes simplex virus-2) is a member of the family Herpetoviridae, a group of DNA viruses that often result in skin lesions (e.g., chickenpox and fever blisters) and are characterized by latent and recurrent infections. HSV-2 is the leading cause of genital ulcers, which can manifest as a cluster of small fluid-filled blisters that rupture and form painful sores, taking several weeks to heal. Additional symptoms may include fever, general sick feeling, muscle aches, painful urination, vaginal discharge, and enlarged, tender lymph nodes in the groin area. Recurring outbreaks are likely. The virus can exist in nerve cells for the life time of the infected subject and reactivate, forming skin ulcers, at irregular intervals. Even in the absence of actual ulcers, the virus can be produced and spread from individual to individual. It is presently incurable.

Genital herpes is the most prevalent sexually transmitted disease. In the United States, over 16% of the population, or about one out of six people, is infected with HSV-2, with a disproportionate burden on women—approximately 20% of women and 12% of men—and on African-Americans—about 40% of the population and nearly 50% of African-American women. (Morbidity and Mortality Weekly Report, 59: 456-459, Apr. 23, 2010). Altogether, about 50 million people in the U.S. are infected, of which about 80% are unaware of their infection, but may still be infectious. Elsewhere in the world, HSV-2 also attains epidemic proportions. A WHO team estimated that in 2003, 536 million people world-wide were infected, and new infections were occurring at about 23 million yearly (Looker et al., Bull World Health Organ. 86: 805-812, 2008). Although prevalence varied by region, generally prevalence increased with age and was higher among women than among men. In addition, HSV-2 prevalence is higher in developing countries than in developed countries—with the exceptions of North America, which has a high HSV-2 prevalence, and south Asia, which has a relatively low HSV-2 prevalence. The highest prevalence is found in Sub-Saharan Africa where nearly 80% of women and 45% of men are infected with HSV-2. Other regions, notably eastern Asia and southeast Asia, approach this level. In addition to sexual transmission, HSV-2 can be transmitted from a woman to a baby, typically at the time of delivery. Concomitant with the HSV-2 epidemic in the adult U.S. population, the incidence of neonatal infection has also dramatically increased. About 1,800 cases of neonatal HSV infection occur yearly in the U.S., which is a higher number of cases than neonatal HIV infection.

The health implications of HSV-2 infection are staggering. Although the vast majority of infected individuals are asymptomatic, virus can still be transmitted. Those with symptoms suffer painful sores on their genitals and anal region and often flu-like symptoms such as fever and swollen glands. Unfortunately, those with a first outbreak of HSV-2 are likely to have several additional outbreaks (typically four or five) within the first year alone. Regardless of the severity of symptoms, knowledge of infection often causes stress and can negatively impact quality of life (Rosenthal, et al., Sex Transm Infect. 82: 154, 2006; Crosby et al Sex Health, 5:279-283, 2008). In neonates infected with HSV-2, neonatal encephalitis from HSV infection has a mortality of >15% even with treatment, and the neurological morbidity among HSV-2 infected infants is an additional 30-50% of surviving cases Coupled with the high prevalence of HSV-2, there is a stark realization that HSV-2 infection substantially increases the risk for HIV-1 acquisition and transmission. Data from Africa show that HSV-2 infection can increase the risk for HIV transmission by as much as seven-fold and that up to one-half of newly acquired HIV cases are directly attributed to HSV-2 infection. Overall, the relative risk of HIV acquisition increases more than two-fold in HSV-2-infected individuals. The synergistic effect on HIV acquisition is greater for HSV-2 than for any other sexually transmitted infection, underscoring the need for an effective public health strategy capable of minimizing the effects of the current HSV-2 epidemic.

The increasing prevalence of HSV-2 in the adult and pediatric populations persists despite the widespread use of pharmacological intervention. Antiviral medication, such as acyclovir, given at high doses early in infection can reduce HSV transmission, but this does not prevent latent infection of the neuronal ganglion. Antiviral therapy has many drawbacks, including as side effects nausea, vomiting, rashes, and decreased kidney function, and should be used with caution because they can be teratogenic as well as be toxic to developing embryos. Furthermore, continuous suppressive administration with valcyclovir reduced HSV transmission by less than 50% despite early intervention. Even if this level of effect were acceptable, the approach is impractical considering the high cost and that 80% of those infected are unaware of their status. Alternatives to antiviral drugs, such as topical microbicides are unproven clinically, and physical barriers (e.g., condoms) have marginal "real-world" efficacy. For these reasons, vaccination is essential for combating and diminishing the health impact of HSV-2 infection.

The first vaccine for HSV was developed in the 1920s, and since then, a variety of vaccine approaches have been tried—all to no avail. The conventional, time-honored types of vaccines including whole, inactivated virus, attenuated live virus, modified live virus, and cell culture-derived subunits were largely unsuccessful or had low efficacy (Stanberry, Herpes 11 (Suppl 3) 161A-169A, 2004). With the advent of recombinant DNA technology, recombinant subunit vaccines have been developed. These vaccines comprised one or two of the envelope glycoproteins in combination with adjuvants. The glycoproteins were attractive candidates mainly because they are the targets of neutralizing antibodies and they are highly conserved among HSV-2 strains. In the last decade, extensive clinical trials on two candidate vaccines, one developed by Chiron and the other by GlaxoSmithKline, were both halted due to insufficient efficacy. Chiron's vaccine comprised truncated forms of two HSV-2 glycoproteins, gD2 and gB2, in combination with the adjuvant MF59. The vaccine at best provided transient protection against HSV-2 although high titers of antibodies to HSV-2 were generated (Stanberry, ibid). GlaxoSmithKline (GSK) developed and tested a similar vaccine; however it contained only a single glycoprotein, gD2, and alum and MPL as adjuvants. Following eight years of studies and clinical trials, GSK pronounced it as a failure in October 2010. The vaccine was unsuccessful in preventing infection in seronegative women, the only group in early clinical trials that had seemed to benefit.

SUMMARY

In one embodiment of the disclosure, an immunogenic fragment of an HSV-2 polypeptide is provided selected from the group consisting of: (a) an immunogenic fragment of UL19 polypeptide lacking at least 75% of amino acids 1-450 of SEQ ID NO: 4 and lacking at least 75% of amino acids of 1055-1374 of SEQ ID NO: 4; (b) the sequence set out in SEQ ID NO: 12; (c) an immunogenic variant of (a) or (b) that retains at least 85% amino acid identity over at least 15 contiguous amino acids; (d) an immunogenic fragment of (a) or (b); and (e) a chimeric fusion of (a), (b), (c) or (d). In another embodiment an isolated polynucleotide encoding the aforementioned polypeptide is provided.

Pharmaceutical compositions are also provided by the instant disclosure. In one embodiment, an immunogenic, pharmaceutical composition is provided comprising: (i) an immunogenic fragment of an HSV-2 polypeptide selected from the group consisting of: (a) an immunogenic fragment of UL19 polypeptide lacking at least 75% of amino acids 1-450 of SEQ ID NO: 4 and lacking at least 75% of amino acids of 1055-1374 of SEQ ID NO: 4; (b) the sequence set out in SEQ ID NO: 12; (c) an immunogenic variant of (a) or (b) that retains at least 85% amino acid identity over at least 15 contiguous amino acids; (d) an immunogenic fragment of (a) or (b); and (e) a chimeric fusion of (a), (b), (c) or (d); (ii) optionally, an agent that activates innate immunity; and (iii) a pharmaceutically acceptable carrier.

In another embodiment, the aforementioned composition is provided which further comprises UL25 or an immunogenic fragment thereof. In still another embodiment, the composition further comprises gD2 or an immunogenic fragment thereof.

In still another embodiment of the instant disclosure, the aforementioned composition is provided wherein the agent is an adjuvant. In one embodiment, the adjuvant is GLA. In another embodiment, the GLA is in the form of an oil-in-water emulsion or an aqueous form. In certain embodiments, the oil-in-water emulsion comprises squalene.

In yet another embodiment of the disclosure, a method for treating an HSV-2 infection in a subject is provided comprising administering an aforementioned composition to the subject. In a another embodiment, a method of generating an immune response in a subject comprising administering an aforementioned composition to the subject is provided. In still another embodiment, a method for immunizing a subject against HSV-2 comprising administering an aforementioned composition to the subject is provided. According to various embodiments of the disclosure, an aforementioned method is provided wherein the administration route is intradermal, mucosal, intramuscular, subcutaneous, sublingual, rectal, or vaginal. In still another embodiment, an aforementioned method is provided further comprising administering a second, third or fourth composition according to any one of claims 3-8 to the subject.

The claimed invention is directed to compositions and methods useful in preventing or treating HSV-2 (herpes simplex virus 2) infections in subjects, preferably humans, in one embodiment the human is female, while in another embodiment the human is male. The compositions comprise (i) an envelope glycoprotein of HSV-2 or an immunogenic fragment of the HSV-2 envelope glycoprotein, (ii) an HSV-2 structural protein or immunogenic fragment of the HSV-2 structural protein, wherein the structural protein is not one of the envelope glycoproteins, (iii) an agent that activates innate immunity in a subject and (iv) a pharmaceutically acceptable carrier. In certain embodiments, the envelope glycoprotein is gD2 and the composition has either gD2 or in an alternative embodiment, an immunogenic fragment derived from gD2. In some embodiments, the structural protein is one or more of UL47, ICP0, ICP4, ICP47, UL5, UL8, UL15, UL19, UL25, UL30, UL32, UL46, UL39 (ICP10), UL7, UL40, UL54 and UL26 and if immunogenic fragments are present, they are derived from UL47, ICP0, ICP4, ICP47, UL5, UL8, UL15, UL19, UL25, UL30, UL32, UL46, UL39 (ICP10), UL7, UL40, UL54 and/or UL26. It is understood that the exact sequence of a protein may vary from one herpesvirus to another, and thus all references to an HSV-2 protein encompasses any such protein obtainable from any naturally occurring HSV-2. In other embodiments, both UL19 and UL25, or fragments from UL19 (e.g. SEQ ID NO. 12, a type of Upper Domain Fragment) and UL25, or a mixture of whole protein and fragments are present, e.g. a mixture of full length UL25 and a fragment of UL19, e.g., SEQ ID NO. 12, optionally with UL47 or a fragment thereof. At times, the agent that activates innate immunity is an adjuvant. In particular the adjuvant can be GLA or another MALA adjuvant. In one embodiment the immunogenic, pharmaceutical composition comprises gD2, GLA or another MALA adjuvant, and two or three antigens selected from full length or fragments of UL25, UL19, and UL47, and a pharmaceutically acceptable carrier. In related embodiments, the immunogenic, pharmaceutical composition comprises a MALA adjuvant, preferably GLA having the structural formula of FIG. 1, gD2, UL25, UL19 Upper Domain Fragment, and a pharmaceutically acceptable carrier; optionally such a composition further comprises one or more additional HSV-2 structural proteins, or fragments thereof.

In some embodiments, the compositions comprise an antigenic portion of an envelope glycoprotein of HSV-2 and a pharmaceutically acceptable carrier. The terms 'immunogenic fragment" and "immunological fragment" and "antigenic portion" are used interchangeably herein to designate fragments or portions of proteins that elicit an antibody response or a cellular cytotoxic response that retains specificity for (cross-reactivity with) the full length protein. In certain embodiments, the antigenic portion binds to neutralizing antibodies. In certain embodiments, the antigenic portion is from gD2 or gB2, and in other embodiments, the antigenic portion, whether from gD2, gB2 or another envelope glycoprotein, comprises at least part and optionally all of the leader sequence. In any of the embodiments, the antigenic portion comprises two or more linear epitopes or comprises two or more discontinuous epitopes from the envelope glycoprotein. In any of the embodiments, the composition further comprises an agent that activates innate immunity. The agent may be an adjuvant, such as GLA as disclosed in, for example, US Publication No. 2009/0181078.

The methods can be used to treat an HSV-2 infection or to generate an immune response, which may prevent or ameliorate an HSV-2 infection. Suitable subjects for the methods include those who are seropositive for HSV-2 as well as those who are seronegative for HSV-2. In the methods, one of the compositions described herein is administered to a subject.

Some exemplary statements of the present invention are set forth as follows, using the designation (xy) where each of x and y denote a letter, the designation denoting an embodiment, or group of embodiments when more than one (xy) is identified within an embodiment. (AA) An immunogenic, pharmaceutical composition comprising (i) an envelope glycoprotein of HSV-2, or an immunological fragment thereof; (ii) a structural protein of HSV-2 other than an envelope glycoprotein of HSV-2, or an immunological fragment thereof; (iii) an agent that activates innate immunity; and (iv) a pharmaceutically acceptable carrier. (AB) Composition (AA) wherein the envelope glycoprotein of HSV-2 is gD2, and the composition comprises gD2. (AC) Composition (AA) wherein the composition comprises an immunological fragment of gD2. (AD) A composition of any one or more of (AA), (AB) and (AC), wherein the structural protein of HSV-2 is one or more proteins selected from the group consisting of UL47, ICP0, UL25, UL46, UL39, UL7, and UL26. (AE) Composition (AA) wherein the structural protein of HSV-2 is UL19. (AF) The composition of (AB) wherein the structural protein of HSV-2 is UL19. (AG) Composition (AA) wherein the structural protein of HSV-2 is an immunological fragment of UL19, e.g., SEQ ID NO. 12. (AH) Composition (AB) wherein the structural protein of HSV-2 is an immunological fragment thereof UL47. (AI) Composition (AA) wherein the structural protein of HSV-2 is UL25. (AJ) Composition (AB) wherein the structural protein of HSV-2 is UL25. (AK) Composition (AA) wherein the structural protein of HSV-2 is an immunological fragment of UL25. (AL) Composition (AB) wherein the structural protein of HSV-2 is ICP0. (AM) Composition (AA) wherein the structural protein of HSV-2 is UL47. (AN) Composition (AB) wherein the structural protein of HSV-2 is a fragment of UL47. (AO) Composition (AA) wherein the structural protein of HSV-2 other than an envelope glycoprotein of HSV-2 is UL47, and is an immunological fragment thereof. (AP) Composition (AB) wherein the structural protein of HSV-2 other than an envelope glycoprotein of HSV-2 is UL47, and is an immunological fragment thereof. (AQ) A composition of any one or more of (AA), (AB), (AC), (AD), (AE), (AF), (AG), (AH), (AI), (AJ), (AK), (AL), (AM), (AN), (AO), (AP) further comprising a second structural protein of HSV-2 other than an envelope glycoprotein of HSV-2, or an immunological fragment thereof. (AR) Composition (AQ) wherein the second structural protein of HSV-2 other than an envelope glycoprotein of HSV-2 is selected from the group consisting of UL19, UL25 and UL47, where the second structural protein is non-identical to the structural protein. (AS) Composition (AR) comprising the second structural protein. (AT) Composition (AR) comprising an immunological fragment of the second structural protein. (AU) A composition of any one or more of (AE), (AF), (AG) and/or (AH) further comprising UL25. (AV) A composition of any one or more of (AE), (AF), (AG) and/or (AH) further comprising an immunological fragment of UL25. (AW) A composition of any one or more of (AE), (AF), (AG) and/or (AH) further comprising UL47. (AX) A composition of any one or more of (AE), (AF), (AG) and/or (AH) further comprising an immunological fragment of UL47. (AY) A composition of any one or more of (AI), (AJ), (AK) and/or (AL) further comprising UL19. (AZ) A composition of any one or more of (AI), (AJ), (AK) and/or (AL) further comprising an immunological fragment of UL19, e.g., SEQ ID NO 12. (BA) A composition of any one or more of (AI), (AJ), (AK) and/or (AL) further comprising UL47. (BB) A composition of any one or more of (AI), (AJ), (AK) and/or (AL) further comprising an immunological fragment of UL47. (BC) A composition of any one or more of (AM), (AN), (AO) and/or (AP) further comprising UL19. (BD) A composition of any one or more of (AM), (AN), (AO) and/or (AP) further comprising an immunological fragment of UL19. (BE) A composition of any one or more of (AM), (AN), (AO) and/or (AP) further comprising UL25. (BF) A composition of any one or more of (AM), (AN), (AO) and/or (AP) further comprising an immunological fragment of UL25. (BG) A composition of any one or more of (AA), (AB), (AC), (AD), (AE), (AF), (AG), (AH), (AI), (AJ), (AK), (AL), (AM), (AN), (AO), (AP), (AQ), (AR), (AS), (AT), (AU), (AV), (AW), (AX), (AY), (AZ), (BA), (BB), (BC), (BD), (BE), and (BF) wherein the agent is an adjuvant. (BH) A composition selected from (BG) wherein the adjuvant is GLA or another MALA adjuvant, and each and every one of the options in (BG) is independently selected as a distinct embodiment of the present invention. (BI) Composition (AA) comprising gD2; UL25; UL19; GLA or another MALA adjuvant; and a pharmaceutically acceptable carrier. (BJ) Composition (AA) comprising gD2, UL25 and an immunological fragment of UL19. (BK) Composition (AA) comprising gD2, UL19, and an immunological fragment of UL25. (BL) A composition of any one or more of (BI), (BJ) and (BK) further comprising UL47. (BM) A composition of any one or more of (BI), (BJ) and (BK) further comprising an immunological fragment of UL47. (BN) A method for treating an HSV-2 infection in a subject, comprising administering the composition of any one or more of (AA), (AB), (AC), (AD), (AE), (AF), (AG), (AH), (AI), (AJ), (AK), (AL), (AM), (AN), (AO), (AP), (AQ), (AR), (AS), (AT), (AU), (AV), (AW), (AX), (AY), (AZ), (BA), (BB), (BC), (BD), (BE), (BF), (BG), (BH), (BI), (BJ), (BK), (BL), and (BM) to the subject. (BO) A method for generating an immune response to HSV-2 in a subject, comprising administering the composition of any one or more of (AA), (AB), (AC), (AD), (AE), (AF), (AG), (AH), (AI), (AJ), (AK), (AL), (AM), (AN), (AO), (AP), (AQ), (AR), (AS), (AT), (AU), (AV), (AW), (AX), (AY), (AZ), (BA), (BB), (BC), (BD), (BE), (BF), (BG), (BH), (BI), (BJ), (BK), (BL), (BM), and (BN) to the subject. (BQ) Method (BO) wherein the subject is seropositive for HSV-2 and seropositive for HSV-1. (BR) Method (BO) wherein the subject is seropositive for HSV-2 and seronegative for HSV-1.

In one embodiment there is provided a composition comprising an envelope glycoprotein of HSV-2 or an immunological fragment thereof; two structural proteins of HSV-2 other than an envelope glycoprotein of HSV-2, or an immunological fragment thereof; an agent that activates innate immunity; and a pharmaceutically acceptable carrier. Exemplary is a composition that comprises gD2, UL25, and SEQ ID NO. 12 (a fragment of UL19) and a monophosphoryl lipid A (MALA) adjuvant, e.g., GLA. In addition to gD2-specific antibody responses, vaccination with this composition may elicit robust HSV-2 antigen-specific CD4 and CD8 effector and memory T cells that respond to subsequent infection with live virus. Notably, prophylactic immunization with this composition may largely or completely protect against lethal intravaginal HSV-2 infection in C57BL/6 mice, with sterilizing immunity in both the genital mucosa and dorsal root ganglia. This composition may expand both CD4 and CD8 T cells induced by previous infection with an attenuated strain of HSV-2. Consistent with this, when applied as a therapy for recurrent HSV-2 lesions in guinea pigs, this composition may reduce the frequency of recurrent lesions.

Kits are also provided. In some kits, there is a vial comprising the pharmaceutical composition comprising an antigenic portion of an HSV-2 envelope glycoprotein and a pharmaceutically acceptable carrier.

These and other aspects and embodiments of the present invention will become evident upon reference to the following detailed description and attached drawings.

DETAILED DESCRIPTION

Figure 1A:
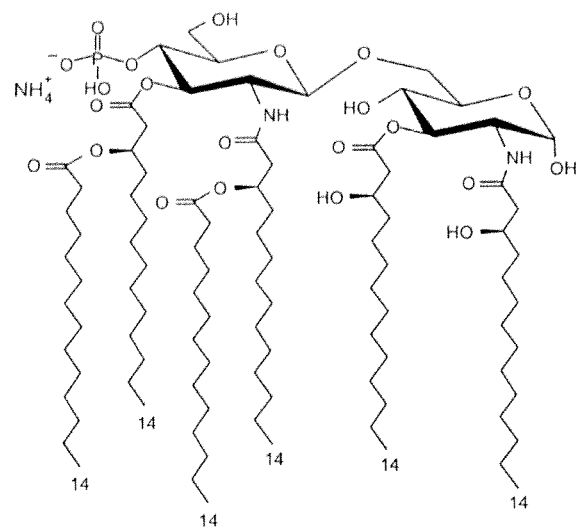
FIGS. 1A-B present a drawing of GLA (the adjuvant used in the Examples) and a schematic of an exemplary oil droplet with surfactants phosphatidycholine and Pluronic F68.

The present disclosure provides immunogenic, pharmaceutical compositions and methods for treatment of or for prevention of herpes simplex virus infections, including HSV-1 and HSV-2 infections. The compositions comprise immunogenic HSV-2 viral proteins or immunogenic portions of the viral proteins, such as fragments or peptides, and at least one agent that activates the innate immune system, preferably a TLR4 agonist, for example, a MALA adjuvant as described herein. The viral proteins (and fragments and peptides) comprise at least one envelope glycoprotein and at least one, two, three or four structural proteins other than an envelope glycoprotein. Alternatively, the viral proteins (and fragments and peptides) comprise at least one antigenic epitope and may comprise part of or all of a leader peptide of an envelope protein. Immunogenic fragments may be used. Some specific agents useful in the compositions include adjuvants, substances that enhance the immune response to an antigen. The proteins and fragments are typically produced by a recombinant technology in which the protein(s) or fragment(s) are expressed in cultured cells. Peptides can also be chemically synthesized.

A. HSV-2 Protein as a Component of a Vaccine

HSV-2 (herpes simplex virus type 2) is an enveloped virus. Its genome expresses over 75 different proteins. Many of the proteins are structural and are used to form the capsid and tegument, while some others are part of the envelope. Major capsid proteins include those expressed from open reading frames (protein names are in parentheses if the common name differs from the ORF name) UL6, UL18 (VP23), UL19 (VP5), UL35 (VP26) and UL38; major tegument proteins include UL7, UL11, UL13, UL14, UL16, UL17, UL21, UL25, UL36, UL37, UL41, UL46 (VP11/12), UL47 (VP13/14), UL48 (VP16), UL49, UL51, and US11; major envelope proteins include UL1 (glycoprotein L (gL)), UL10 (gM), UL20, UL22 (gH), UL27 (gB), UL43, UL44 (gC), UL49A (gN), UL53 (gK), US4 (gG), US5, (gJ), US6 (gD), US7 (gI), and US8 (gE). (Other protein names may have been used in the literature.) An exemplary HSV-2 genome sequence is found in GenBank Accession No. NC 001798.1 (update date 23 Apr. 2010, 2:16 pm, accessed 10 Jan. 2011; incorporated in its entirety). It is understood that the commonly used protein names may be different from the gene names, e.g. UL19 encodes VP5, but reference to the gene name herein is the same as a reference to the encoded protein. It is also understood that the exact sequence of a protein may vary from one herpesvirus to another, and thus all references to an HSV-2 protein (structural or envelope or non-envelope) encompass any such protein obtainable from any naturally occurring HSV-2. A number of sequences are already known and deposited in databases. Nucleic acid encoding an HSV-2 protein with an alternative sequence can be readily isolated or amplified from one or more HSV-2 (e.g. a deposited HSV-2 or a clinical isolate) with appropriate oligonucleotide probes or primers (e.g. that specifically hybridize to a reference sequence under stringent conditions). Within such a group of nucleic acids that encode an HSV-2 protein, e.g. an UL protein, one nucleic acid of the group will hybridize to the complement of another nucleic acid within the group, under stringent conditions.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence-dependent, and are different under different environmental parameters. An extensive guide to the hybridization of nucleic acids is found in Tijssen, Laboratory Techniques in Biochemistry and Molecular Biology—Hybridization with Nucleic Acid Probes, Part I, Chapter 2 in "Overview of principles of hybridization and the strategy of nucleic acid probe assays", Elsevier (New York, 1993). In certain embodiments, highly stringent hybridization and wash conditions are about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. In certain embodiments, very stringent conditions are equal to the $T_m$ for a particular probe.

An example of stringent hybridization conditions for hybridization of complementary nucleic acids that have more than 100 complementary residues on a filter in a Southern or Northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see Sambrook et al. for a description of SSC buffer). A high stringency wash can be preceded by a low stringency wash to remove background probe signal. An example of medium stringency wash for a duplex of, e.g., more than 100 nucleotides, is 1×SSC at 45° C. for 15 minutes. An example of low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

Because one or more envelope proteins is involved in viral entry into host cells, antibodies to envelope proteins can neutralize the virus, that is prevent infection or re-infection by the virus. Without wishing to be held to a mechanistic theory, eliciting antibodies to one or more of those envelope proteins necessary for cellular entry is one way to obtain neutralizing antibodies. Vaccines comprising whole virus, typically inactivated virus, naturally present envelope proteins to immune cells. For a vaccine comprising individual viral proteins, one strategy to obtaining a neutralizing antibody response is to include one or more envelope proteins or immunogenic protein fragments or immunogenic peptides or some combination of these in a vaccine.

HSV-2 encodes 14 or more envelope-associated proteins, at least some of which are involved with cellular entry, including but not limited to gB, gD, gH, and gL. gD appears to bind specifically to an HSV-2 receptor on cells, and gB, along with the heterodimer gH/gL, appears to mediate membrane fusion. Thus, these four envelope glycoproteins are excellent choices as immunogens for inclusion in a vaccine because antibodies elicited to these envelope glycoproteins may include neutralizing antibodies. Alternatively, or in addition, envelope glycoproteins involved in virus shedding are also candidates as immunogens for inclusion in a vaccine.

Most of the structural proteins of HSV-2 other than envelope proteins are found in the capsid and the tegument. The tegument occupies the space between the capsid and the envelope. There are approximately 20 viral proteins found in the tegument. Tegument proteins are important for a variety of viral functions, including immune modulation, viral assembly and final egress. Capsid proteins form a structure that surrounds the nucleic acid genome of the virion. VP5, the product of UL19 is the major capsid protein. A cellular response is often elicited to structural proteins and to a variety of HSV proteins (Hosken et al., J Virol 80:5509-55515, 2006). Generally, the cellular response involves both CD4 and CD8 T cells, cell types that play a role in combating HSV infections.

The immunogenic, pharmaceutical composition (e.g., a vaccine) disclosed herein comprises as immunogens two or more structural proteins, one of which is an envelope glycoprotein and another of which is other than an envelope glycoprotein. Although any of the structural proteins can be used, the choice may be guided by ease of production, ability to formulate into a pharmaceutical composition, information on protein structure, and high expression levels. Because T cell responses are typically MHC-restricted, a vaccine generally contains proteins or peptides that are responded to by the highest number of MHC types, and it may also contain multiple proteins or peptides in order to increase number of individuals that will respond.

Immunogenic pharmaceutical compositions are preferably sterile, free or substantially free of other viral contaminants, and free or substantially free of pyrogenic substances such as LPS. Such compositions are for use as vaccines.

The envelope and non-envelope structural proteins for use in a vaccine as immunogens are typically full-length, but can also be a precursor protein, fragment, or part of a fusion protein. A full-length protein refers to a mature protein; for example, in the case of an envelope protein, a mature protein is the form found in the envelope (e.g., lacking a leader peptide). A precursor protein (pre-protein) is the nascent, translated protein before any processing occurs or a partially-processed protein. As part of a fusion protein, the HSV-2 protein may be present as a precursor or full-length protein or a protein fragment. A fragment of a protein should be immunogenic, containing one or more epitopes that elicit an immune response.

In some embodiments, the immunogenic, pharmaceutical composition (e.g., a vaccine) disclosed herein comprises as immunogens (i) an α group gene product of HSV-2, or an immunological fragment thereof; and/or (ii) a β1 group gene product of HSV-2, or an immunological fragment thereof; and/or (iii) a β2 group gene product of HSV-2, or an immunological fragment thereof; and/or (iv) a γ1 group gene product of HSV-2, or an immunological fragment thereof; and/or (v) a γ2 group gene product of HSV-2, or an immunological fragment thereof. The α, β1, β2, γ1, and γ2 genes are well-known in the art. See, for example, *Herpesviruses and Their Replication* in FUNDAMENTAL VIROLOGY, Chapter 29, 1986.

Thus, any use of the term "immunogen" herein refers to the entire group of polypeptides that are: (a) full length antigen, (2) immunogenic fragments of the antigen, (3) immunogenic variants of the full length antigen or variants of an immunogenic fragment, (4) chimeric fusions thereof comprising portions of a different polypeptide, and (5) conjugates thereof. In various embodiments, the envelope and non-envelope structural proteins for use in a vaccine include a polypeptide comprising any of an immunogenic fragment thereof or a variant thereof capable of inducing an immune response specific for the protein.

For example, immunogenic variants retain at least 90% amino acid identity over at least 10 contiguous amino acids of the antigen, or at least 85% amino acid identity over at least 15 contiguous amino acids of the antigen (e.g. an envelope protein or non-envelope structural protein). Other examples include at least 70%, 75%, 80%, 85%, 90%, 91%, 92%, 93%, 94%, 95%, 96%, 97%. 98%, or 99% identity over at least 50 contiguous amino acids of the antigen, or over at least 100 contiguous amino acids of the antigen. In one embodiment, an immunogenic variant has at least 70%, 75%, 80%, 85%, 90%, 91%, 92%, 93%, 94%, 95%, 96%, 97%. 98%, or 99% identity over the full length of a particular antigen. In some embodiments, the variant is a naturally occurring variant.

As another example, immunogenic fragments, and variants thereof, comprise at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 50 contiguous amino acids of the antigen. The immunogenic fragment may comprise any number of contiguous amino acids between the aforementioned such that, for example, an immunogenic fragment is between about 6-10, 10-15, 15-20, 20-30, 30-40, 40-50, 50-60, 60-70, 70-80, 80-90, 90-100, or more contiguous amino acids of an immunogenic polypeptide.

Short fragments, often called peptides, are chosen to complex with MHC molecules for binding to T cell receptors and are generally up to about 30 amino acids long, or up to about 25 amino acids long, or up to about 20 amino acids long, or up to about 15 amino acids long, up to about 12 amino acids long, up to about 9 amino acids long, up to about 8 amino acids long. In general, shorter peptides bind to or associate with MHC Class I molecules and longer peptides bind to or associate with MHC Class II molecules. Suitable peptides can be predicted using any of a number of bioinformatic programs and tested using well-known methods. Short fragments, also called herein "peptides" are typically from 15-100 amino acids long; longer fragments typically are from 100 amino acids up to full-length, although the length ranges for peptides (short fragments) and longer fragments are not rigid.

As disclosed herein, suitable proteins include precursor proteins, mature proteins, fragments, fusion proteins and peptides. In the compositions, the proteins may be present in the same form or as a mixture of these forms. For example, an envelope glycoprotein may be present as a mature protein and a structural protein as a fragment or an envelope glycoprotein may be present as a fragment and a structural protein as a fragment. For cellular production of the glycoprotein, a signal peptide may be part of the precursor protein. Signal peptides include the glycoprotein D native sequence or others known in the art. It may also be desirable to use a protein without a transmembrane or intracellular region or both.

As discussed herein, one or more portions, also called fragments, of an envelope glycoprotein are chosen for containing one or more epitopes that bind to neutralizing antibodies. Portions containing epitopes may be identified by an assay, such as inhibition of neutralizing antibodies on viral infection of cells. Briefly, overlapping portions of an HSV-2 envelope glycoprotein are mixed with neutralizing antibodies (e.g., serum from an infected animal or human), and the mixture added to HSV-2 and a permissive cell line. If a portion has an epitope that binds to the antibodies, the cell line will be infected with HSV-2. If the portion doesn't have an epitope, the cell line will not be infected.

Compositions that comprise at least one immunogenic fragment of an immunogenic HSV-2 polypeptide may be used as immunogens. In some embodiments, the immunogenic fragment is encoded by the recombinant expression vectors described herein. The immunogenic fragment may consist of at least 6, 10, 15, 20, 30, 40, 50, 60, 70, 80, 90, 100, or more contiguous amino acids of an immunogenic polypeptide. The immunogenic fragment may comprise any number of contiguous amino acids between the aforementioned such that, for example, an immunogenic fragment is between about 6-10, 10-15, 15-20, 20-30, 30-40, 40-50, 50-60, 60-70, 70-80, 80-90, 90-100, or more contiguous amino acids of an immunogenic polypeptide. The immunogenic fragments may comprise a sufficient number of contiguous amino acids that form a linear epitope and/or may comprise a sufficient number of contiguous amino acids that permit the fragment to fold in the same (or sufficiently similar) three-dimensional conformation as the full-length polypeptide from which the fragment is derived to present a non-linear epitope or epitopes (also referred to in the art as conformational epitopes). Assays for assessing whether the immunogenic fragment folds into a conformation comparable to the full-length polypeptide include, for example, the ability of the protein to react with mono- or polyclonal antibodies that are specific for native or unfolded epitopes, the retention of other ligand-binding functions, and the sensitivity or resistance of the polypeptide fragment to digestion with proteases (see, e.g., Sambrook et al., Molecular Cloning: A Laboratory Manual, 3d ed., Cold Spring Harbor Laboratory Press, NY (2001)). Accordingly, by way of example, the three-dimensional conformation of a polypeptide fragment is sufficiently similar to the full-length polypeptide when the capability to bind and the level of binding of an antibody that specifically binds to the full-length polypeptide is substantially the same for the fragment as for the full-length polypeptide (i.e., the level of binding has been retained to a statistically, clinically, and/or biologically sufficient degree compared with the immunogenicity of the exemplary or wild-type full-length antigen).

Fragments that are screened in an assay, such as that described above, are generally short. Generally, the length of a candidate fragment is up to about 40 amino acids long, or up to about 25 amino acids long, or up to about 20 amino acids long, or up to about 15 amino acids long, or up to about 12 amino acids long, or up to about 9 amino acids long, or up to about 8 amino acids long. Fragments used for screening are typically overlapping. For example, a set of fragments might comprise 20 amino acid long fragments that overlap by 16 amino acids (i.e., staggered every 4 amino acids). Typically, the overlapping sets start at the N-terminus of an unprocessed glycoprotein, i.e., contains a leader sequence, and ends at the C-terminal amino acid of the extracellular domain.

Fragments that bind to neutralizing antibody are chosen and may be used in a pharmaceutical composition as disclosed herein. The fragments may be used "as-is" or engineered further or in combination with other fragments. For fragments that are big enough and complex enough to be immunogenic, they may be used in pharmaceutical compositions. Fragments less than about 1000 MW are unlikely to be immunogenic, although complexity can also play a role in whether a fragment is immunogenic. For example, homopolymers consisting of repeating units of a single amino acid are poor immunogens regardless of their size, whereas co-polymers of 2 or 3 amino acids may be good immunogens. A co-polymer of glutamic acid and lysine needs to be at least about 30-40,000 MW to be immunogenic. Amino acids with aromatic side chains increase immunogenicity, such that a fragment of only about 4000 MW that comprises tyrosine and phenylalanine may be immunogenic. Fragments that are too short or not complex enough to be immunogenic may be conjugated to a carrier protein, such as KLH (keyhole limpit hemocyanin), ovalbumim, bovine serum albumin, or other protein that is foreign to the subject receiving the pharmaceutical composition, or the fragments may be coupled together to create an immunogenic protein. Whether or not a fragment is immunogenic may be determined in an animal. For example, the fragment may be administered to an animal in a prime-boost regimen, and antibodies to the fragment assayed in an e.g., ELISA using serum drawn 7-10 days following the boost. A detectable signal indicates that the fragment is immunogenic. Higher signals are desirable. Other assays for immunogenicity are well known to one of average skill.

In some embodiments, the fragments used in the compositions are synthetic long peptides. "Synthetic long peptide" (SLP) refers to a protein sequence manufactured ex vivo and having a length as short as about 25 amino acids and as long as about 100 amino acids. An SLP should be long enough to be taken up and processed by dendritic cells for presentation on their cell surface with MHC class I or class II molecules. SLPs are peptides derived from proteins against which an immune response is desired. In one embodiment, the immune response is a T cell response. The proteins may be known antigens or, in the case of some proteins, they may be candidate antigens.

An SLP comprises at least one CD4 epitope or at least one CD8 epitope or at least one CD4 and at least one CD8 epitope. A CD4 epitope refers to an amino acid sequence that binds to class II MHC and a CD8 epitope refers to an amino acid sequence that binds to class I MHC. Epitope sequences are derived from the amino acid sequence of an immunogen; in vivo, briefly, the immunogen is taken up or synthesized by antigen-processing cells (e.g., dendritic cells) and degraded into peptides, which associate with MHC molecules and are presented on the cell surface as an MHC-peptide complex. Peptides complexed with MHC class I molecules interact with the T cell antigen receptor and CD8 on CD8+ T cells, these peptides are called CD8 epitopes; peptides complexed with MHC class II molecules interact with T cell antigen receptor and CD4 on CD4+ T cells, these peptides are called CD4 epitopes. Activated CD8+ T cells become cytotoxic T cells, which recognize and kill target cells displaying the MHC class I-CD8 epitopes. Often, target cells are infected or tumor cells. Activated CD4+ T cells become helper T cells, and depending on their subtype, help B cells to produce antibody or activate natural killer cells, phagocytes and CD8+ T cells. Activation of both CD4+ T cells and CD8+ T cells contribute to a comprehensive cellular immune response.

As disclosed above, an SLP should be long enough to be taken up and processed by dendritic cells and presented on their cell surface with MHC molecules. Peptides complexed with MHC class 1 molecules are generally 8-11 amino acids in length, and peptides complexed with MHC class II molecules are generally 13-17 amino acids in length, although longer or shorter lengths are not uncommon. As such, an SLP will typically be at least 25 amino acids long and as long as 100 amino acids long (e.g., at least 30 aa, at least 35 aa, at least 40 aa, at least 45 aa, at least 50 aa, at least 55 aa, at least 60 aa, at least 65 aa, at least 70 aa, at least 75 aa, at least 80 aa, at least 85 aa, at least 90 aa, at least 95 aa). The length of an SLP will generally be about 45 aa or about 50 aa in length.

Epitopes may have known sequence or unknown sequence. A plethora of proteins have been mapped for CD4 and CD8 epitopes. For SLPs comprising one or more of these epitopes, the length will typically be about 45 aa. Moreover, the epitope may be flanked by about 15 aa at the N-terminal and at the C-terminal sides. The flanking sequences are typically the sequences that flank the epitope sequence in the native protein. As discussed above, an SLP may comprise more than one epitope, the multiple epitopes may be all CD4 or CD8 epitopes or a mixture of CD4 and CD8 epitopes. Furthermore, the epitopes may overlap in sequence (see Example 1 for some exemplary SLPs that comprise overlapping epitopes). The total number of SLPs used may be such that all known CD4 and CD8 epitopes are represented.

SLPs may be synthesized by any of a variety of methods (see Corradin et al., Sci Translational Med 2:1, 2010 for a general discussion of synthesis methods). Automated peptide synthesizers are commercially available, and many companies provide synthesis services (e.g., Abbiotec, American Peptide Company, AnaSpec, Bachem, Covance Research Products, Invitrogen). Following synthesis, peptides are purified, typically by HPLC, although alternative purification methods such as ion exchange chromatography and gel filtration chromatography may be used. Acceptable purity is at least 90% or at least 95% or at least 98% as assessed by analytical HPLC.

When a protein has not been mapped for CD4 epitopes or CD8 epitopes or both, a set of SLPs that comprise the entire protein sequence may be synthesized. Each SLP will typically be about 50 aa, and consecutive SLPs may overlap in sequence by about 25 aa. Alternatively, or in addition, algorithms and computer programs can be used to predict sequences that will bind to MHC class I and class II molecules. Such programs are readily available, e.g., RANKPEP (Reche et al., Human Immunol 63: 701, 2002), Epipredict (Jung et al., Biologicals 29: 179, 2001) and MHCPred (Guan et al. Nucl Acids Res 31: 3621, 2003 and Guan et al., Appl Bioinformatics 5: 55, 2006), EpiMatrix (EpiVax, Inc.).

The sequence of an SLP may be adjusted as necessary for optimum production. For example, one or more amino acids at the ends of a peptide derived from a native sequence may be omitted in order to improve solubility or stability, or to increase or decrease the overall charge. As a specific example, a peptide sequence with a high content of hydrophobic amino acids may be difficult to solubilize. As a guide, hydrophobic content is ideally less than 50%. Peptides containing cysteine, methionine, or tryptophan residues, especially multiple Cys, Met, or Trp residues, may be difficult to synthesize. Substitution of another amino acid, either a standard or a non standard amino acid, such as hydroxyproline, gamma-aminobutyric acid, norleucine, may improve synthesis efficiency or purity. Other considerations in designing an SLP include the extent of β-sheet formation, N-terminal amino acid (e.g., an N-terminal Gln can cyclize), minimizing adjacent Ser and Pro residues.

Some structural proteins that are especially useful for inclusion in a pharmaceutical composition include UL19 (SEQ ID No. 4), UL19 Upper Domain Fragment (SEQ ID No. 12), UL 25 (SEQ ID No. 5) and UL47 (SEQ ID No. 6). Structure of viral proteins may be found in MMDB (Molecular Modeling Database) of NCBI. Molecular structure information is available for UL25 (MMDB ID: 37706, Bowman et al. J. Virol. 80:2309, 2006, incorporated in its entirety), VP5 (product of UL19) (MMDB ID: 26005, Bowman et al., EMBO J. 22: 757-765, 2003, incorporated in its entirety), VP13/14 (product of UL47) (MMDB ID: 6022), and envelope protein gD2 (MMDB ID: 36244, Krummenacher et al. EMBO J. 24:4144-4153, 2005, incorporated in its entirety), ICP34.5, as well as many other HSV-2 proteins. In addition, some T-cell epitopes of viral proteins are known (Koelle et al., J Virol 74:10930-10938, 2000; Muller et al., J Gen Virol 90:1153-1163, 2009; Koelle et all, J Immunol 166:4049-4058, 2001; BenMohamed et al., J Virol 77:9463-9473, 2003; U.S. Pat. No. 6,855,317; P.C.T. Pub. No. WO 2004/009021, all of which references are incorporated in their entirety).

Immunogenic fragments, variants and fusion proteins of any of these are proteins, especially UL19, UL19 Upper Domain Fragment, UL25 and UL47, are specifically contemplated for use in the immunogenic compositions herein. Thus, the disclosure includes fragments or variants of any one of SEQ ID NO: 4, 5, 6, or 12 that retain at least 90% amino acid identity over at least 10 contiguous amino acids thereof, or at least 85% amino acid identity over at least 15 contiguous amino acids thereof. As another example, the disclosure includes immunogenic fragments comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48 or 50 contiguous amino acids of the sequence, or between about 6-10, 10-15, 15-20, 20-30, 30-40, 40-50, 50-60, 60-70, 70-80, 80-90, 90-100, or more contiguous amino acids of the sequence. The disclosure also includes variants having at least 70%, 75%, 80%, 85%, 90%, 91%, 92%, 93%, 94%, 95%, 96%, 97%. 98%, or 99% identity over at least 50 contiguous amino acids of the sequence, or over at least 100 contiguous amino acids of the sequence. In some embodiments, the variant is a naturally occurring variant, preferably one that hybridizes under stringent conditions to a polynucleotide encoding any one of SEQ ID NO: 4, 5, 6 or 12.

As disclosed herein, immunogenic fragments, including peptides, of a non-envelope structural protein (e.g., UL19 peptides as set forth in SEQ ID Nos. 9 and 10 and UL25 peptides as set forth in SEQ ID No. 11) and of an envelope protein (e.g., gD2 (SEQ ID Nos. 7 and 8) may be used or may be part of a longer sequence (i.e., fragment) derived from the protein. Peptides, as used herein, refer to short sequences of amino acids, generally from at least 15 residues and generally up to about 100 residues, or from about 20 residues to about 80 residues, or from about 30 residues to about 70 residues. Fragments, as used herein, refer to any length of polypeptide less than full-length protein and are generally at least 100 amino acids long, although the size range of fragments can overlap the size range of peptides (e.g., fragments from about 50 residues long). In particular, a UL19 Upper Domain Fragment is missing at least 75%, 80%, 85%, 90%, 95% or all of residues 1-450 and residues 1055-1374 of UL19. As such, the Upper Domain Fragment may begin, for example, at any one of residues 337-451, and end at any one of residues 1055-1294 (and is lacking at least amino acids 1-336 and 1295-1374 of SEQ ID NO: 4). For example, a UL19 fragment may be from about residue 451 to about 1054 (SEQ ID NO:12). A UL19 Upper Domain Fragment may comprise about 50, 100, 150, 200, 250, 300, 350, 400, 450, or 500 amino acids or more of SEQ ID NO: 12.

In addition, the peptides and fragments herein may be fused to heterologous peptides. Examples of heterologous peptides include sequences from other proteins (e.g., in the case of UL19, a UL19 Upper Domain Fragment may be fused to a sequence from another protein that is not UL19), or tag sequences, such as hexa-histidine, which generally will be located at either the N-terminus or the C-terminus. Thus, the immunogenic fragments or variants described herein may be fused to another peptide that enhances immunogenicity, another peptide that serves as a tag or marker, or another peptide from another HSV-2 structural protein. As such, an immunogenic polypeptide may comprise a fragment consisting of a designated fragment of an HSV-2 structural protein. In one example, an immunogenic polypeptide comprises a fragment of UL19 consisting of SEQ ID NO: 12 or a fragment of SEQ ID NO: 12, optionally fused to a non-UL19 peptide. In another example, an immunogenic polypeptide comprises a peptide consisting of an amino acid sequence that is at least 80% or 90% identical over 50 contiguous amino acids of SEQ ID NO: 12, optionally fused to a non-UL19 peptide.

Surprisingly, the examples herein show that a UL19 Upper Domain Fragment has the ability to elicit protective antibodies to HSV-2 infection, such that the remainder of the UL19 protein is not needed as an immunogen. This surprising discovery is fortuitous as attempts to express full length UL19 have proven challenging. For example, full length UL19 expression in *E. coli* and other expression systems, and subsequent purification of soluble full length UL 19, has proven difficult.

Typically the proteins in a pharmaceutical composition will be other than a precursor protein because expression in a eukaryotic cell will typically result in a mature protein, lacking the leader sequence (also known as a signal peptide). The leader sequence of gD encompasses approximately residues 1-25. The leader sequence of gB encompasses approximately residues 1-22. Glycoprotein D (SEQ ID No. 2) is 393 amino acid protein and has an extracellular region spanning approximately residues 26-340, a transmembrane region spanning approximately residues 341-361 and a cytoplasmic region spanning approximately residues 362-393, and a number of N-linked glycosylation sites at residues 119, 146, 287 (UniProtKB/Swiss-Prot accession number Q69467, version 49 of entry and version 1 of sequence). An exemplary gD fragment (herein alternatively referred to as gD2) comprises the sequence shown in SEQ ID No. 3.

In some embodiments, antigenic and immunogenic fragments from envelope glycoproteins may comprise part or all of a leader sequence, which is sometimes called a signal peptide. The leader sequence is usually approximately 15-20 amino acids, and in normal cellular processes, it may be cleaved off by cellular apparatus, however, some of the glycoprotein in intact virions may have the leader sequence. Leader sequences usually have some polar amino acids at the N-terminus and the internal amino acids are generally hydrophobic. As discussed above, the leader sequences for some of the HSV-2 envelope glycoproteins have been determined. For other HSV-2 envelope glycoproteins, computer programs may be used to predict the signal peptide. Some of these programs include SIG-Pred (bmbpcu36.leeds.ac.uk/prot_analysis/Signal.html), PrediSi, OCTOPUS (octopus.cbr.su.se), and sigcleave (emboss.sourceforge.net/apps/cvs/emboss/apps/sigcleave.html).

A variety of techniques may be used to inhibit cleavage of the signal peptide during cellular production of an antigenic or immunogenic fragment containing the leader sequence for use in the compositions described herein. For example, one or more of the amino acids flanking the cleavage site may be altered to a different amino acid, resulting in a sequence that is not recognized or cleaved by cellular apparatus. For this method, alterations are designed based on cleavage sites known in the art: glycine is not preferentially used in any of the positions, tyrosine, is rarely found in the first few positions after cleavage sites, whereas proline is often found in many cleavage sites except at the +1 position and glutamine is commonly found at the +1 residue (Zhang and Henzel, Protein Sci. 13: 219, 2004). The proposed sequence may be evaluated with a prediction program to determine if cleavage is likely to be inhibited. If cleavage is likely, then additional alterations are made and the newly proposed sequence re-evaluated. Other techniques to inhibit cleavage of a signal peptide include addition of one or more amino acids at the recognition and cleavage sequence, N-terminal addition of a signal peptide and recognition sequence such that the added signal peptide is preferentially cleaved, and production in a host cell that lacks the machinery to cleave the signal peptide.

In certain embodiments, a fragment comprises an HSV-2 glycoprotein, including the leader sequence. In other embodiments, a fragment comprises a portion of a HSV-2 glycoprotein including from the leader sequence to the start of the transmembrane domain. In yet other embodiments, a fragment comprises a portion of an HSV-2 glycoprotein including from the leader sequence and ending within the extracellular domain. In other embodiments, a fragment comprises non-contiguous portions of an HSV-2 glycoprotein, in which one of the portions comprises an antigenic epitope in the leader sequence. In yet other embodiments, a fragment comprises non-contiguous portions of an HSV-2 glycoprotein, in which the portions comprise an epitope or it comprises portions from different HSV-2 glycoproteins, in which the portions comprise an epitope.

Glycoprotein B (SEQ ID No. 1) has an extracellular region spanning approximately residues 23-771, a transmembrane region spanning approximately residues 772-792 and a cytoplasmic region spanning approximately residues 793-904, and a number of N-linked glycosylation sites at residues 82, 136, 393, 425, 486, 671 (UniProtKB/Swiss-Prot accession number P08666, version 60 of entry and version 2 of sequence). Glycoprotein K is a 338 amino acid protein with a 30 amino acid leader sequence at its N-terminal end (Ramaswarmy and Holland, Virology 186:579-587, 1992). Glycoprotein C has a predicted 27 amino acid leader sequence, glycoprotein E has a predicted 23 amino acid leader sequence, and glycoprotein L has a predicted 16 amino acid leader sequence (Signal Peptide Resource, proline.bic.nus.edu.sg, accessed 6 Oct. 2011).

Proteins or protein fragments are preferably immunogenic. An "immunogen" is capable of inducing an immune response. Immunogenic peptide sequences are generally recognized by T cells (e.g., CD4 or CD8 T cells) in at least some seropositive subjects. Peptide sequences can be identified by screening peptides derived from the complete sequence, generally using a series of overlapping peptides. A variety of assays can be used to determine if T cells recognize and respond to a peptide. For example, a chromium-release cytotoxicity assay (Kim et al., J Immunol 181:6604-6615, 2008, incorporated for its assay protocol), ELISPOT assay, an intracellular cytokine staining assay and MHC multimer staining (Novak et al. J Clin Invest 104: R63-R67, 1999; Altman et al., Science 274:94-96, 1996) are among suitable assays. In some cases, the fragment(s) comprise immunodominant peptide sequences. Some immunodominant epitopes have been identified for HSV-2 glycoproteins and structural proteins (e.g., Kim et al. J Immunol 181:6604-6615, 2008; Chentoufi et al., J. Virol. 82:11792-11802, 2008; Koelle et al., Proc Natl Acad Sci USA 100: 12899-12904, 2003; all references are hereby incorporated in their entirety). Immunogenic peptides can also be predicted by bioinformatic software (Flower, Methods in Molecular Biology vol. 409, 2007). Some exemplary programs and databases include FRED (Feldhahn et al. Bioinformatics 15:2758-9, 2009), SVMHC (Dönnes and Kohlbacher, Nucleic Acids Res 34:W1940197, 2006), AntigenDB (Ansari et al., Nucleic Acids Res 38:D847-853, 2010), TEPITOPE (Bian and Hammer Methods 34:468-475, 2004), Any of the HSV-2 proteins, including precursor proteins, mature proteins and fragments, including peptides, can be incorporated as part of a fusion protein. The fusion partner or partners can be any of the HSV-2 proteins or a non-HSV-2 protein sequence. Some common reasons to use fusion proteins are to improve expression or aid in purification of the resulting protein. For example, a signal peptide sequence tailored for the host cell of an expression system can be linked to an HSV-2 protein or a tag sequence for use in protein purification can be linked, and subsequently cleaved if a cleavage sequence is also incorporated. Multiple peptide epitopes from one or more of the proteins can be fused or fragments from one or more of the proteins can be fused. For example, structural proteins or fragments of structural proteins can be linked, such as a fusion protein of VP13/14 (UL47) and major capsid protein (UL19) or UL25 and UL47 or UL25 and UL19. The segments of a fusion protein can be in any order, that is for a fusion of UL19 and UL47, either protein can be at the N-terminus. Similarly, multiple peptide epitopes can be in any order.

Manufacture of HSV-2 proteins, including precursor proteins, fragments, and fusion proteins is generally achieved by expression in cultured cells or by chemical synthesis. ("HSV-2 proteins" is used herein to include all these forms.) Short fragments are commonly synthesized chemically, either using a machine (many are commercially available) or manually. If produced by cells, a variety of suitable expression systems, both prokaryotic and eukaryotic systems, are well known and may be used. Host cells often used and suitable for production of proteins include *E. coli*, yeast, insect, and mammalian. Expression vectors and host cells are commercially available (e.g., Invitrogen Corp., Carlsbad, Calif., USA) or may be constructed. An exemplary vector comprises a promoter and cloning site for the sequence encoding a protein of interest such that the promoter and sequence are operatively linked. Other elements may be present, such as a secretion signal sequence (sometimes called a leader sequence), a tag sequence (e.g., hexa-His), transcription termination signal, an origin of replication, especially if the vector is replicated extra-chromosomally, and a sequence encoding a selectable product. Methods and procedures to transfect host cells are also well known.

Expressed proteins are collected and may be used "as-is" or more typically, analyzed and further purified. Typical procedures for determining purity or quantity include gel electrophoresis, Western blotting, mass spectrometry, and ELISA. Activity of proteins is generally assessed in a biological assay, such as those described in the Examples. If necessary or desired, proteins may be further purified. Many purification methods are well known and include size chromatography, anion or cation exchange chromatography, affinity chromatography, precipitation, and immune precipitation. Intended use of the protein will typically determine the extent of purification, with use in humans requiring likely the highest level of purity.

B. Agents that Activate Innate Immunity

The innate immune system comprises cells that provide defense in a non-specific manner to infection by other organisms. Innate immunity is an immediate defense but it is not long-lasting or protective against future challenges. Immune system cells that generally have a role in innate immunity are phagocytic, such as macrophages and dendritic cells. The innate immune system interacts with the adaptive (also called acquired) immune system in a variety of ways. Cells of the innate immune system can participate in antigen presentation to cells of the adaptive immune system, including expressing lymphokines that activate other cells, emitting chemotactic molecules that attract cells that may be specific to the invader, and secreting cytokines that recruit and activate cells of the adaptive immune system. The immunogenic pharmaceutical compositions disclosed herein include an agent that activates innate immunity in order to enhance the effectiveness of the composition.

Many types of agents can activate innate immunity. Organisms, like bacteria and viruses, can activate innate immunity, as can components of organisms, chemicals such as 2'-5' oligo A, bacterial endotoxins, RNA duplexes, single stranded RNA and other molecules. Many of the agents act through a family of molecules—the Toll-like receptors (TLRs). Engaging a TLR can also lead to production of cytokines and chemokines and activation and maturation of dendritic cells, components involved in development of acquired immunity. The TLR family can respond to a variety of agents, including lipoprotein, peptidoglycan, flagellin, imidazoquinolines, CpG DNA, lipopolysaccharide and double stranded RNA (Akira et al. Biochemical Soc Transactions 31: 637-642, 2003). These types of agents are sometimes called pathogen (or microbe)-associated molecular patterns.

In one aspect, one or more adjuvants are included in the composition, in order to provide an agent(s) that activates innate immunity. An adjuvant is a substance incorporated into or administered simultaneously with antigen that increases the immune response. A variety of mechanisms have been proposed to explain how different adjuvants work (e.g., antigen depots, activators of dendritic cells, macrophages). Without wishing to be bound by theory, one mechanism involves activating the innate immune system, resulting in the production of chemokines and cytokines, which in turn activate the adaptive (acquired) immune response. In particular, some adjuvants activate dendritic cells through TLRs. Thus, an adjuvant is one type of agent that activates the innate immune system that may be used in a vaccine to HSV-2. An adjuvant may act to enhance an acquired immune response in other ways too. Preferably the adjuvant is a TLR4 agonist.

One adjuvant that may be used in the compositions described herein is a monoacid lipid A (MALA) type molecule. An exemplary MALA is MPL® adjuvant as described in, e.g., Ulrich J. T. and Myers, K. R., "Monophosphoryl Lipid A as an Adjuvant" Chapter 21 in Vaccine Design, the Subunit and Adjuvant Approach, Powell, M. F. and Newman, M. J., eds. Plenum Press, NY 1995. Another exemplary MALA is described by the chemical formula (I):

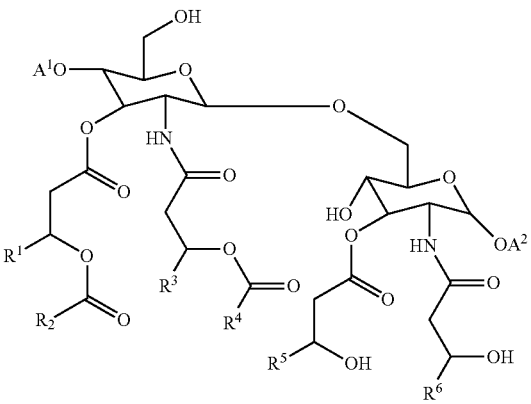

wherein the moieties $A^1$ and $A^2$ are independently selected from the group of hydrogen, phosphate, phosphate salts, carboxylate, carboxylate salts, sulfate, sulfate salts, sulfite, sulfite salts, aspartate, aspartate salts, succinate, succinate salts, carboxymethylphosphate and carboxymethylphosphate salts. Sodium and potassium are exemplary counterions for the phosphate and carboxylate salts. At least one of $A^1$ and $A^2$ is hydrogen. The moieties $R^1$, $R^2$, $R^3$, $R^4$, $R^5$, and $R^6$ are independently selected from the group of hydrocarbyl having 3 to 23 carbons, preferably a straight chain alkyl, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

"Hydrocarbyl" or "alkyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, i.e., to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl", respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like. For example, "$C_{6-11}$ alkyl" mean an alkyl as defined above, containing from 6-11 carbon atoms, respectively.

The adjuvant of formula (I) may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. Certain of the adjuvants may also be obtained commercially. A preferred adjuvant is Product No. 699800 as identified in the catalog of Avanti Polar Lipids, Alabaster Ala., wherein R1, R3, R5 and R6 are undecyl and R2 and R4 are tridecyl.

In various embodiments of the invention, the adjuvant has the chemical structure of formula (I) but the moieties A1, A2, R1, R2, R3, R4, R5, and R6 are selected from A1 being phosphate or phosphate salt and A2 is hydrogen; and R1, R3, R5 and R6 are selected from C7-C15 alkyl; and R2 and R4 are selected from C9-C17 hydrocarbyl. In a preferred embodiment of the invention, the GLA used in the examples herein has the structural formula set forth in FIG. 1, wherein R1, R3, R5 and R6 are undecyl and R2 and R4 are tridecyl.

The MALA adjuvants described above are a preferred adjuvant class for use in the immunogenic pharmaceutical compositions described herein. However, any of the following adjuvants may also be used alone, or in combination with an MALA adjuvant, in formulating an immunogenic pharmaceutical composition.

The adjuvant may be alum, where this term refers to aluminum salts, such as aluminum phosphate (AlPO4) and aluminum hydroxide (Al(OH)$_3$). When alum is used as the adjuvant or as a co-adjuvant, the alum may be present, in a dose of immunogenic pharmaceutical composition in an amount of about 100 to 1,000 μg, or 200 to 800 μg, or 300 to 700 μg or 400 to 600 μg. If the adjuvant of formula (I) is co-formulated with alum, the adjuvant of formula (I) is typically present in an amount less than the amount of alum, in various aspects the adjuvant of formula (I), on a weight basis, is present at 0.1-1%, or 1-5%, or 1-10%, or 1-100% relative to the weight of alum. In one aspect of the invention, the composition excludes the presence of alum.

The adjuvant may be an emulsion having vaccine adjuvant properties. Such emulsions include oil-in-water emulsions. Freund's incomplete adjuvant (IFA) is one such adjuvant Another suitable oil-in-water emulsion is MF-59™ adjuvant which contains squalene, polyoxyethylene sorbitan monooleate (also known as Tween™ 80 surfactant) and sorbitan trioleate. Squalene is a natural organic compound originally obtained from shark liver oil, although also available from plant sources (primarily vegetable oils), including amaranth seed, rice bran, wheat germ, and olives. Other suitable emulsion adjuvants are Montanide™ adjuvants (Seppic Inc., Fairfield N.J.) including Montanide™ ISA 50V which is a mineral oil-based adjuvant, Montanide™ ISA 206, and Montanide™ IMS 1312. While mineral oil may be present in the adjuvant, in one embodiment, the oil component(s) of the compositions of the present invention are all metabolizable oils.

The adjuvant may be AS02™ adjuvant or AS04™ adjuvant. AS02™ adjuvant is an oil-in-water emulsion that contains both MPL™ adjuvant and QS-21™ adjuvant (a saponin adjuvant discussed elsewhere herein). AS04™ adjuvant contains MPL™ adjuvant and alum. The adjuvant may be Matrix-M™ adjuvant.

The adjuvant may be a saponin such as those derived from the bark of the *Quillaja saponaria* tree species, or a modified saponin, see, e.g., U.S. Pat. Nos. 5,057,540; 5,273,965; 5,352,449; 5,443,829; and 5,560,398. The product QS-21™ adjuvant sold by Antigenics, Inc. Lexington, Mass. is an exemplary saponin-containing co-adjuvant that may be used with the adjuvant of formula (1). Related to the saponins is the ISCOM™ family of adjuvants, originally developed by Iscotec (Sweden) and typically formed from saponins derived from Quillaja *saponaria* or synthetic analogs, cholesterol, and phospholipid, all formed into a honeycomb-like structure.

The adjuvant may be a cytokine that functions as an adjuvant, see, e.g., Lin R. et al. Clin. Infec. Dis. 21(6):1439-1449 (1995); Taylor, C. E., Infect. Immun. 63(9):3241-3244 (1995); and Egilmez, N. K., Chap. 14 in Vaccine Adjuvants and Delivery Systems, John Wiley & Sons, Inc. (2007). In various embodiments, the cytokine may be, e.g., granulocyte-macrophage colony-stimulating factor (GM-CSF); see, e.g., Change D. Z. et al. Hematology 9(3):207-215 (2004), Dranoff, G. Immunol. Rev. 188:147-154 (2002), and U.S. Pat. No. 5,679,356; or an interferon, such as a type I interferon, e.g., interferon-α (IFN-α) or interferon-β (IFN-β), or a type II interferon, e.g., interferon-γ (IFN-γ), see, e.g., Boehm, U. et al. Ann. Rev. Immunol. 15:749-795 (1997); and Theofilopoulos, A. N. et al. Ann. Rev. Immunol. 23:307-336 (2005); an interleukin, specifically including interleukin-1α (IL-1α), interleukin-10 (IL-1β), interleukin-2 (IL-2); see, e.g., Nelson, B. H., J. Immunol. 172(7):3983-3988 (2004); interleukin-4 (IL-4), interleukin-7 (IL-7), interleukin-12 (IL-12); see, e.g., Portielje, J. E., et al., Cancer Immunol. Immunother. 52(3): 133-144 (2003) and Trinchieri. G. Nat. Rev. Immunol. 3(2):133-146 (2003); interleukin-15 (1'-15), interleukin-18 (IL-18); fetal liver tyrosine kinase 3 ligand (Flt3L), or tumor necrosis factor α (TNFα).

The adjuvant may be unmethylated CpG dinucleotides, optionally conjugated to the antigens described herein.

Examples of immunopotentiators that may be used in the practice of the methods described herein as co-adjuvants include: MPL™; MDP and derivatives; oligonucleotides; double-stranded RNA; alternative pathogen-associated molecular patterns (PAMPS); saponins; small-molecule immune potentiators (SMIPs); cytokines; and chemokines.

In various embodiments, the co-adjuvant is MPL™ adjuvant, which is commercially available from GlaxoSmithKline (originally developed by Ribi ImmunoChem Research, Inc. Hamilton, Mont.). See, e.g., Ulrich and Myers, Chapter 21 from Vaccine Design: The Subunit and Adjuvant Approach, Powell and Newman, eds. Plenum Press, New York (1995). Related to MPL™ adjuvant, and also suitable as co-adjuvants for use in the compositions and methods described herein, are AS02™ adjuvant and AS04™ adjuvant. AS02™ adjuvant is an oil-in-water emulsion that contains both MPL™ adjuvant and QS-21™ adjuvant (a saponin adjuvant discussed elsewhere herein). AS04™ adjuvant contains MPL™ adjuvant and alum. MPL™ adjuvant is prepared from lipopolysaccharide (LPS) of *Salmonella minnesota* R595 by treating LPS with mild acid and base hydrolysis followed by purification of the modified LPS.

When two adjuvants are utilized in combination, the relative amounts of the two adjuvants may be selected to achieve the desired performance properties for the composition which contains the adjuvants, relative to the antigen alone. For example, the adjuvant combination may be selected to enhance the antibody response of the antigen, and/or to enhance the subject's innate immune system response. Activating the innate immune system results in the production of chemokines and cytokines, which in turn may activate an adaptive (acquired) immune response. An important consequence of activating the adaptive immune response is the formation of memory immune cells so that when the host re-encounters the antigen, the immune response occurs quicker and generally with better quality.

The adjuvant(s) may be pre-formulated prior to their combination with the HSV-2 proteins. In one embodiment, an adjuvant may be provided as a stable aqueous suspension of less than 0.2 um and may further comprise at least one component selected from the group consisting of phospholipids, fatty acids, surfactants, detergents, saponins, fluorodated lipids, and the like. The adjuvant(s) may be formulated in an oil-in-water emulsion in which the adjuvant is incorporated in the oil phase. For use in humans, the oil is preferably metabolizable. The oil may be any vegetable oil, fish oil, animal oil or synthetic oil; the oil should not be toxic to the recipient and is capable of being transformed by metabolism. Nuts (such as peanut oil), seeds, and grains are common sources of vegetable oils. Particularly suitable metabolizable oils include squalene (2,6,10,15,19,23-hexamethyl-2,6,10,14,18,22-tetracosahexane), an unsaturated oil found in many different oils, and in high quantities in shark-liver oil. Squalene is an intermediate in the biosynthesis of cholesterol. In addition, the oil-in-water emulsions typically comprise an antioxidant, such as alpha-tocopherol (vitamin E, U.S. Pat. No. 5,650,155, U.S. Pat. No. 6,623,739). Stabilizers, such as a triglyceride, ingredients that confer isotonicity, and other ingredients may be added. An exemplary oil-in-water emulsion using squalene is known as "SE" and comprises squalene, glycerol, phosphatidylcholine or lecithin or other block co-polymer as a surfactant in an ammonium phosphate buffer, pH 5.1, with alpha-toceraphol.

The method of producing oil-in-water emulsions is well known to a person skilled in the art. Commonly, the method comprises mixing the oil phase with a surfactant, such as phosphatidylcholine, poloxamer, block co-polymer, or a TWEEN80® solution, followed by homogenization using a homogenizer. For instance, a method that comprises passing the mixture one, two, or more times through a syringe needle is suitable for homogenizing small volumes of liquid. Equally, the emulsification process in a microfluidiser (M110S microfluidics machine, maximum of 50 passes, for a period of 2 min at maximum pressure input of 6 bar (output pressure of about 850 bar)) can be adapted to produce smaller or larger volumes of emulsion. This adaptation can be achieved by routine experimentation comprising the measurement of the resultant emulsion until a preparation was achieved with oil droplets of the desired diameter. Other equipment or parameters to generate an emulsion may also be used. Disclosures of emulsion compositions, and method of their preparation, may be found in, e.g., U.S. Pat. Nos. 5,650,155; 5,667,784; 5,718,904; 5,961,970; 5,976,538; 6,572,861; and 6,630,161.

C. Pharmaceutical Compositions and Uses

1. Formulation

A claimed pharmaceutical composition comprises an HSV-2 glycoprotein or an immunogenic fragment thereof, an HSV-2 structural protein other than an envelope glycoprotein or an immunogenic fragment thereof, an agent that is an agonist for the innate immune system, and a pharmaceutically acceptable carrier. The composition may comprise more than one glycoprotein (or fragment), more than one structural protein (or fragment) or more than one agent.

In some aspects, the pharmaceutical composition comprises an antigenic portion of an HSV glycoprotein, a pharmaceutically acceptable carrier, and optionally an agent that is an agonist for the innate immune system. The composition may comprise more than one glycoprotein portion and one or more than one agent. The carrier may optionally have adjuvant properties, e.g., some emulsion carriers have adjuvant properties. Although herein primarily the HSV glycoproteins that are discussed are from HSV-2, glycoproteins from HSV-1 may also be used.

In certain embodiments, the glycoprotein or the structural protein or both may be a precursor protein, a mature protein, a fragment, a fusion protein, or a peptide. The glycoprotein and structural protein elements may be part of the same or different fusion proteins. Similarly, if there is more than one glycoprotein or more than one structural protein, they may be part of a single fusion protein or parts of separate fusion proteins. If there is more than one glycoprotein or more than one structural protein, each of the more than one proteins can be a precursor protein, mature protein, fragment, etc. that is, for example, two glycoproteins may comprise a fragment and a peptide or for example, two different fragments of the same glycoprotein or for example, two fragments of different glycoproteins.

The amount of each of the proteins or immunologic fragments in each vaccine dose typically ranges from about 0.5 µg to about 50 µg, or about 0.5 µg, about 1.0 µg, about 2 µg, about 5 µg, about 10 µg, about 15 µg, about 20 µg, about 30 µg, about 40 µg, about 50 µg, about 75 µg, about 100 µg, or about 150 µg or about 200 µg or about 250 µg or any other suitable amount that would be determined to provide efficacy against HSV-2. The proteins or immunologic fragments may be present in a variety of ratios, including equimolar ratios, which provides equal epitope representation, and equimass ratios, which provides equal mass of each individual protein. Equimolar and equimass ratios that are within about 20% (e.g., 0.8:1.2), or within about 10% (e.g., 0.9:1.1) or within about 5% (e.g., 0.95:1.05) of equivalence are still considered to be equimolar or equimass. The dose will typically be determined by pharmacological activity of the composition, purpose (therapeutic or prophylactic), and the size and condition of the subject.

The proteins may be supplied as a solution, but can also be desiccated (dry) in which case, a user adds the necessary liquid. Typically, additives such as buffers, stabilizers, tonicity agents, surfactants, preservatives, carriers, and other non-active ingredients will also be present. The additives are typically pharmaceutically acceptable and bio-compatible. Preferably, the additives, immunogens, agents, etc. are substantially free of other endotoxins, toxic compounds, and contaminants that can cause unwanted side-effects. Formulations may vary according to the route of administration. For example, a formulation for administration by i.m. injection will generally be isotonic and aqueous, while a formulation for oral administration may be encapsulated as a slow-release form or contain flavors. Formations for aerosol administration will generally be packaged under pressure and contain a propellant.

The agent, which may be an adjuvant, may be provided as a solution, desiccated, or emulsified, generally as a stable oil-in-water emulsion. In one embodiment, an agent may be provided as a stable aqueous suspension of less than 0.2 um and may further comprise at least one component selected from the group consisting of phospholipids, fatty acids, surfactants, detergents, saponins, fluorodated lipids, and the like. Such a stable aqueous formulation may be a micellar formulation. In another embodiment, the agent may be formulated in a manner which can be aerosolized, either as a powder or liquid formulation.

Any of these may also comprise buffers, stabilizers, preservatives, carriers, or other non-active ingredients. The additives are typically pharmaceutically acceptable and biocompatible. More than one agent may be present, and one, some or all of the agents may also be an adjuvant or co-adjuvant. In addition, an adjuvant, or co-adjuvant, that is not also an agent may also be provided. Antigen depots, such as oils or at least some oil emulsions may also be present.

The amount of an adjuvant agent such as GLA or another MALA adjuvant is typically about 0.5 µg, about 1 µg, about 2 µg, about 2.5 µg, about 5 µg, about 7.5 µg, about 10 µg, about 15 µg, about 20 µg or about 25 µg. An emulsion, such as SE, may be present at about 0.1%, about 0.5%, about 1.0%, about 1.5%, about 2%, about 2.5%, about 3%, about 4%, about 5%, about 7.5% or about 10%

The agent and proteins may be provided in separate containers and mixed on-site or pre-mixed. In addition, the proteins may be presented in separate containers or combined in a single container. The agent and proteins may be provided in a concentrated form and provided with a diluent. Suitable diluents include saline and PBS. A container can a vial, ampoule, tube, well of a multi-well device, reservoir, syringe or any other kind of container. The container or containers may be provided as a kit. If one or more of the containers comprises desiccated ingredients the liquids for reconstitution may be provided in the kit as well or provided by the user. The amount of solution in each container or that is added to each container is commensurate with the route of administration and how many doses are in each container. A vaccine given by injection is typically from about 0.1 ml to about 2.0 ml, while a vaccine that is given orally may be a larger volume, from about 1 ml to about 10 ml for example. Suitable volumes may also vary according to the size and age of the subject.

2. Administration

The composition may be used for treatment of an HSV-2 infection in subjects. As used herein, "treatment" is a clinical intervention that may be therapeutic or prophylactic. In therapeutic applications, pharmaceutical compositions or mendicants are administered to a subject suspected of having or known to have an HSV-2 infection. The composition is given in an amount sufficient to generate (induce) an immune response that can cure, or at least partially arrest, the symptoms of the disease and its complications. In prophylactic applications, pharmaceutical compositions or mendicants are administered to a subject susceptible to, or otherwise at risk of, an HSV-2 infection in an amount sufficient to induce an immune response that will inhibit infection or reduce the risk or delay the outset of the disease or ameliorate one or more of the effects of infection. An amount adequate to accomplish this is defined as a therapeutically- or pharmaceutically-effective dose. Such an amount can be administered as a single dosage or can be administered according to a regimen, whereby it is effective. The amount can cure a disease but, typically, is administered in order to ameliorate the symptoms of a disease, or to effect prophylaxis of a disease or disorder from developing.

In both therapeutic and prophylactic regimes, agents are usually administered in several dosages until a sufficient immune response has been achieved. Typically, the immune response is monitored and repeated dosages are given if the immune response starts to fade. Treatment need not completely eliminate a disease, nor need it completely prevent a subject from becoming ill with the disease or disorder. In some embodiments, only a single dosage is administered. More often, multiple dosages will be administered. Generally, the first dosage is called a "priming" dosage and the second and subsequence dosages are called "boosting" dosages. Multiple dosages may consist of two administrations, of three administrations, of four administrations, and at times, of five or more administrations. Ideally, the number is one or two administrations. When multiple administrations are provided, the timing of the second, and subsequent, administrations will generally be at least two weeks following the last administration, and may be at least one month, two months, three months, six months, or 1 year following the last administration. Ideally, an immune response is monitored in order to determine if multiple dosages would be advantageous. The multiple dosages may contain equivalent amount of immunogens and agonist or may contain different amounts of these ingredients. For example, a boosting dosage may comprise lower amounts of immunogens. Furthermore, additives may differ between dosages.

In some embodiments, the priming composition that is administered to the subject is a live attenuated HSV-2 virus and the boosting composition that is administered to the subject is any composition claimed or described herein. In some embodiments, the priming composition that is administered to the subject is any composition claimed or described herein and the boosting composition that is administered to the subject is a live attenuated HSV-2 virus.

Whether used as a prophylactic or as a therapeutic, administration preferably raises an immune response to HSV-2. The immune response can be humoral (antibody mediated) or cellular (typically, although not exclusively T cell mediated) or both. The immunized subject may also have activated monocytes, macrophages, NK cells, dendritic cells, and other innate immune cell types. Assays for an immune response are described herein and are well known by one of average skill.

Vaccine is administered at a dose sufficient to effect a beneficial therapeutic response (therapeutically effective dose) e.g., effective immune response to ameliorate, alleviate, cure or partially ameliorate symptoms of disease or infection, or prophylactic response, e.g., prevent infection or disease symptoms. Indicators of a beneficial therapeutic response is fewer herpes lesions in any given outbreak or a lower number of lesions on average, or less frequent outbreaks. Other indicators include smaller lesions, lesions that heal more quickly, inure less pain. Still other indicators are development of antibodies to HSV-2 vaccine components, in particular presence of antibodies to HSV-2 envelope glycoproteins, e.g., antibodies to gD2, and also particularly development of neutralizing antibodies. There are many well known procedures to detect and quantify antibodies, including ELISA and inhibition of virus infection (neutralization) assays. In one implementation, the ELISA assay is performed by coating wells of a multi-well plate with gD2 protein, capturing gD2-specific antibody from serum onto the plates, detecting the gD2-specific antibody with labeled anti-human antibody, followed by a readout of the label. Label can be radioactive, but is more usually an enzyme, such as horse radish peroxidase, that converts a substrate to one that can be detected colorimetrically. An exemplary HSV neutralization assay is based on a plaque assay in which neutralizing antibody is detected by inhibition of plaque formation. Other indicators include an increased amount or function or frequency of CD8 or CD4 T cells responsive to HSV-2, a reduction in virus shedding, reduction in viral transmission to sexual partners, and reduction of size or frequency or both of symptomatic lesions.

Assays for T cell function include IFN-γ ELISPOT and ICS (intracellular cytokine staining). The ELISPOT assay detecting interferon-gamma is widely used to quantize CD4 and CD8 T cell responses to candidate vaccines. The ELISPOT assay is based on the principle of the ELISA detecting antigen-induced secretion of cytokines trapped by an immobilized antibody and visualized by an enzyme-coupled second antibody. ICS is a routinely used method to quantify cytotoxic T cells by virtue of cytokine expression following stimulation with agonists, such as antibodies to T cell surface molecules or peptides that bind MHC Class molecules. Exemplary procedures of ICS and ELISPOT are described below.

Subjects to receive the vaccine include both HSV-2 seropositive and HSV-2 seronegative individuals. For seropositive individuals, the vaccine is intended to be therapeutic. For seronegative individuals, the vaccine is intended to be protective. In some cases, subjects are seropositive for HSV-1 and in other cases, are seronegative for HSV-1, independent of HSV-2 status. That is, subjects may include those who are HSV-1 seropositive/HSV-2 seropositive, HSV-1 seronegative/HSV-2 seropositive, HSV-1 seropositive/HSV-2 seronegative, HSV-1 seronegative/HSV-2 seronegative. Moreover, subjects include human and other mammalian subjects that can be infected by HSV-2.

The vaccine can be administered by any suitable delivery route, such as intradermal, mucosal (e.g., intranasal, oral), intramuscular, subcutaneous, sublingual, rectal, and vaginal. Other delivery routes are well known in the art.

The intramuscular route is one suitable route for the composition. Suitable i.m. delivery devices include a needle and syringe, a needle-free injection device (for example Biojector, Bioject, Oreg. USA), or a pen-injector device, such as those used in self-injections at home to deliver insulin or epinephrine. Intradermal and subcutaneous delivery are other suitable routes. Suitable devices include a syringe and needle, syringe with a short needle, and jet injection devices.

The composition may be administered by a mucosal route, e.g., intranasally. Many intranasal delivery devices are available and well known in the art. Spray devices are one such device. Oral administration can as simple as providing a solution for the subject to swallow.

Vaccine may be administered at a single site or at multiple sites. If at multiple sites, the route of administration may be the same at each site, e.g., injection in different muscles, or may be different, e.g., injection in a muscle and intranasal spray. Furthermore, the vaccine may be administered at a single time point or multiple time points. Generally if administered at multiple time points, the time between doses has been determined to improve the immune response.

Recombinant Expression Vectors, Viral Vectors, and Virus-Like Particles

In one embodiment, recombinant expression vectors are provided that comprise a polynucleotide sequence encoding at least one HSV2 immunogen that induces an immune response to the immunogen and to its respective designated antigen. To obtain efficient transcription and translation of the immunogen, the encoding polynucleotide sequences in each vector include at least one appropriate expression control sequence (also called a regulatory expression sequence or feature) (e.g., promoter, enhancer, leader), which are described in greater detail herein, that is operatively linked to the encoding polynucleotide sequence(s). These recombinant expression vectors are thus provided for directing expression of the immunogen or for directing co-expression of at least two immunogens in any appropriate host cell that has been transformed, transduced, or transfected with the recombinant expression vector or vector particle containing the recombinant expression vector.

The recombinant expression vectors described herein may encode one or more HSV-2 immunogens (i.e., at least one, at least two, at least three immunogens, etc.), which immunogens are described in greater detail herein. In particular embodiments, at least one, two, or three, or more immunogens from HSV-2 may be encoded by a recombinant expression vector. By way of example, an immunogen may be an HSV-2 protein, such as UL19 (e.g., UL19 Upper Domain Fragment or an immunogenic fragment or variant thereof) and/or gD, (or an immunogenic fragment or variant thereof) and/or UL47 (or an immunogenic fragment or variant thereof), or may be another immunogenic fragment or region of the HSV-2 protein.

A. Recombinant Production of Protein

A recombinant expression vector that comprises a polynucleotide sequence that encodes an immunogen may be used for production of the immunogen. Recombinant expression vectors include at least one regulatory expression sequence, such as a promoter or enhancer, that is operatively linked to the polynucleotide encoding the immunogen. Each of the expression vectors may be used to transform, transducer, or transfect an appropriate host cell for recombinant production of a respective immunogen. Suitable host cells for production of the immunogen include prokaryotes, yeast and higher eukaryotic cells (e.g., CHO and COS). The immunogen may each be isolated from the respective host cell or host cell culture using any one of a variety of isolation methods (e.g., filtration, diafiltration, chromatography (including affinity chromatography, high pressure liquid chromatography), and preparative electrophoresis) known and routinely practiced in the protein art. In certain embodiments, as described herein, the isolated immunogen may then be formulated with a pharmaceutically suitable excipient to provide an immunogenic composition.

Particular methods for producing polypeptides recombinantly are generally well known and routinely used. For example, molecular biology procedures are described by Sambrook et al. (Molecular Cloning, A Laboratory Manual, 2nd ed., Cold Spring Harbor Laboratory, New York, 1989; see also Sambrook et al., 3rd ed., Cold Spring Harbor Laboratory, New York, (2001)). DNA sequencing can be performed as described in Sanger et al. (Proc. Natl. Acad. Sci. USA 74:5463 (1977)) and the Amersham International plc sequencing handbook and including improvements thereto.

B. Recombinant Expression Vectors for Delivery of Protein to Subjects

Recombinant expression vectors may be used for expression of any one or more of the immunogens described herein. In particular embodiments, the recombinant expression vector is delivered to an appropriate cell (for example, an antigen-presenting cell i.e., a cell that displays a peptide/MHC complex on its cell surface, such as a dendritic cell) or tissue (e.g., lymphoid tissue) that will induce the desired immune response (i.e., a specific humoral response (i.e., B cell response) and/or induction of a specific cell-medicated immune response, which may include an immunogen-specific CD4 and/or CD8 T cell response, which CD8 T cell response may include a cytotoxic T cell (CTL) response). The recombinant expression vectors may therefore also include, for example, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., Mol. Cell. Biol. 12, 1043-53 (1992); Todd et al., J. Exp. Med. 177, 1663-74 (1993); Penix et al., J. Exp. Med. 178:1483-96 (1993)).

In a particular embodiment, the recombinant expression vector is plasmid DNA or cosmid DNA. Plasmid DNA or cosmid DNA containing one or more polynucleotides encoding an immunogen as described herein is readily constructed using standard techniques well known in the art. The vector genome may be typically constructed in a plasmid form that can then be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline. For analysis to confirm that the correct nucleotide sequences are incorporated in plasmids, the plasmid may be replicated in *E. coli*, purified, and analyzed by restriction endonuclease digestion and/or its nucleotide sequence determined by conventional methods.

C. Viral Vectors

In other particular embodiments, the recombinant expression vector is a viral vector. Exemplary recombinant expression viral vectors include a lentiviral vector genome, poxvirus vector genome, vaccinia virus vector genome, adenovirus vector genome, adenovirus-associated virus vector genome, herpes virus vector genome, and alpha virus vector genome. Viral vectors may be live, attenuated, replication conditional or replication deficient, and typically is a non-pathogenic (defective), replication competent viral vector.

By way of example, in a specific embodiment, when the viral vector is a vaccinia virus vector genome, the polynucleotide encoding an immunogen of interest may be inserted into a non-essential site of a vaccinia viral vector. Such non-essential sites are described, for example, in Perkus et al., Virology 152:285 (1986); Hruby et al., Proc. Natl. Acad. Sci. USA 80:3411 (1983); Weir et al., J. Virol. 46:530 (1983). Suitable promoters for use with vaccinia viruses include but are not limited to P7.5 (see, e.g., Cochran et al., J. Virol. 54:30 (1985); P11 (see, e.g., Bertholet, et al., Proc. Natl. Acad. Sci. USA 82:2096 (1985)); and CAE-1 (see, e.g., Patel et al., Proc. Natl. Acad. Sci. USA 85:9431 (1988)). Highly attenuated strains of vaccinia are more acceptable for use in humans and include Lister, NYVAC, which contains specific genome deletions (see, e.g., Guerra et al., J. Virol. 80:985-98 (2006); Tartaglia et al., AIDS Research and Human Retroviruses 8:1445-47 (1992)), or MVA (see, e.g., Gheradi et al., J. Gen. Virol. 86:2925-36 (2005); Mayr et al., Infection 3:6-14 (1975)). See also Hu et al. (J. Virol. 75:10300-308 (2001), describing use of a Yaba-Like disease virus as a vector for cancer therapy); U.S. Pat. Nos. 5,698,530 and 6,998,252. See also, e.g., U.S. Pat. No. 5,443,964. See also U.S. Pat. Nos. 7,247,615 and 7,368,116.

In certain embodiments, an adenovirus vector or adenovirus-associated virus vector may be used for expressing an immunogen of interest. Several adenovirus vector systems and methods for administering the vectors have been described (see, e.g., Molin et al., J. Virol. 72:8358-61 (1998); Narumi et al., Am J. Respir. Cell Mol. Biol. 19:936-41 (1998); Mercier et al., Proc. Natl. Acad. Sci. USA 101:6188-93 (2004); U.S. Pat. Nos. 6,143,290; 6,596,535; 6,855,317; 6,936,257; 7,125,717; 7,378,087; 7,550,296).

Retroviral vector genomes may include those based upon murine leukemia virus (MuLV), gibbon ape leukemia virus (GaLV), ecotropic retroviruses, simian immunodeficiency virus (SIV), human immunodeficiency virus (HIV), and combinations (see, e.g., Buchscher et al., J. Virol. 66:2731-39 (1992); Johann et al., J. Virol. 66:1635-40 (1992); Sommerfelt et al., Virology 176:58-59 (1990); Wilson et al., J. Virol. 63:2374-78 (1989); Miller et al., J. Virol. 65:2220-24 (1991); Miller et al., Mol. Cell. Biol. 10:4239 (1990); Kolberg, NIH Res. 4:43 1992; Cornetta et al., Hum. Gene Ther. 2:215 (1991)).

D. Lentiviral Vectors

In a more specific embodiment, the recombinant expression viral vector is a lentiviral vector genome. The genome can be derived from any of a large number of suitable, available lentiviral genome based vectors, including those identified for human gene therapy applications (see, e.g., Pfeifer et al., Annu. Rev. Genomics Hum. Genet. 2:177-211 (2001)). Suitable lentiviral vector genomes include those based on Human Immunodeficiency Virus (HIV-1), HIV-2, feline immunodeficiency virus (FIV), equine infectious anemia virus, Simian Immunodeficiency Virus (SIV), and maedi/visna virus. A desirable characteristic of lentiviruses is that they are able to infect both dividing and non-dividing cells, although target cells need not be dividing cells or be stimulated to divide. Generally, the genome and envelope glycoproteins will be based on different viruses, such that the resulting viral vector particle is pseudotyped. Safety features of the vector genome are desirably incorporated. Safety features include self-inactivating LTR and a non-integrating genome. Exemplary vectors contain a packaging signal (psi), a Rev-responsive element (RRE), splice donor, splice acceptor, central polypurine tract (cPPT), and WPRE element. In certain exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (see, e.g., Zufferey et al., J. Virol. 72: 9873, 1998; Miyoshi et al., J. Virol. 72:8150, 1998; both of which are incorporated in their entirety). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (see, e.g., U.S. Pat. Nos. 5,385,839 and 5,168,062).

In certain embodiments, the risk of insertional mutagenesis is minimized by constructing the lentiviral vector genome to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC); the central domain core, which contains the catalytic core and a conserved DD35E motif (D64, D116, E152 in HIV-1); and a C-terminal domain, which has DNA binding properties. Point mutations introduced into integrase are sufficient to disrupt normal function. Many integrase mutations have been constructed and characterized (see, e.g., Philpott and Thrasher, Human Gene Therapy 18:483, 2007; Apolonia, Thesis submitted to University College London, April 2009, pp, 82-97; Engelman et al., J. Virol. 69: 2729, 1995; Nightingale et al., Mol. Therapy, 13: 1121, 2006). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SW integrase completely abolishes viral DNA integration. Deletions of integrase will generally be confined to the C-terminal domain. Deletion of coding sequence for residues 235-288 result in a useful non-functional integrase (see, e.g., Engelman et al., J. Virol. 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g., W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (see, e.g., Brown et al., J. Virol. 73:9011 (1999)). In one exemplification, the CA at each end is changed to TG. In other exemplifications, the CA at each end is changed to TG at one end and GT at the other end. In other exemplifications, the CA at each end is deleted; in other exemplifications, the A of the CA is deleted at each end.

Integration can also be inhibited by mutation or deletion of polypurine tract (PPT) (see, e.g., WO 2009/076524), located proximally to the 3' LTR. The PPT is a polypurine sequence of about 15 nucleotides that can serve as a primer binding site for plus-strand DNA synthesis. In this instance, mutations or deletions of PPT targets the reverse transcription process. Without wishing to be held to a particular mechanism, by mutating or deleting PPT, production of linear DNA is radically reduced, and essentially only 1-LTR DNA circles are produced. Integration requires a linear double-stranded DNA vector genome, and integration is essentially eliminated without it. As stated herein, a PPT can be made non-functional by mutation or by deletion. Typically, the entire about 15 nt PPT is deleted, although in some embodiments, shorter deletions of 14 nt, 13, nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (see, e.g., McWilliams et al., J. Virol. 77:11150, 2003), although single and double mutations in the first four bases still reduce transcription. Mutations made at the 3' end of PPT generally have a more dramatic effect (see, e.g., Powell et al., J. Virol. 70:5288, 1996).

The U3 region may comprise a PPT (polypurine tract) sequence immediately upstream. In certain specific embodiments, any one of at least three different U3 regions (at the 3' end) may be included in the lentiviral vector (see SEQ ID NOS:13-15). The constructs contain deletions in the U3 regions. The SIN construct has a deletion of about 130 nucleotides in the U3 (see, e.g., Miyoshi, et al. J. Virol. 72: 8150, 1998; Yu et al., Proc. Natl. Acad. Sci. USA 83: 3194, 1986), which removes the TATA box, thereby abolishing LTR promoter activity. The deletions in constructs 703 and 704 increase expression from lentivirus vectors (see, e.g., Bayer et al., Mol. Therapy. 16: 1968, 2008). In addition, construct 704 contains a deletion of the 3' PPT, which decreases integration of the vector (see, e.g., WO 2009/076524). See also U.S. patent application Ser. No. 12/842,609 and International Patent Application Publication No. WO 2011/011584 (International Patent Application No. PCT/US10/042,870), which are each incorporated by reference in their entirety.

These different approaches to make a vector genome non-integrating can be used individually or in combination. Using more than one approach may be used to build a fail-safe vector through redundant mechanisms. Thus, PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

As described herein, lentiviral vector constructs may also contain a promoter for expression in mammalian cells. Promoters, which are discussed in greater detail herein, include, for example, the human ubiquitin C promoter (UbiC), the cytomegalovirus immediate early promoter (CMV), and the Rous sarcoma virus (RSV) promoter.

E. Virus-Like Particles

In various embodiments, virus-like particles (VLP) are provided that comprise a at least one HSV2 immunogen that induces an immune response to the immunogen and to its respective designated antigen.

An HSV-1 or HSV-2 virus-like particle can be prepared by allowing VP5, VP19, VP23, VP22a, and the maturational protease (UL26 gene product) to self-assemble in vitro. See, for example, Newcomb et al., *J. Virol*, September 1994, 6059-6063.; Newcomb et al., *J. Mol. Biol.*, 263; 432-446 (1996); Thomsen et al., *J Virol*, April 1994, 2442-2457; all incorporated by reference in their entirety. The virus-like particles described herein may comprise one or more HSV-2 immunogens (i.e., at least one, at least two, at least three immunogens, etc.), which immunogens are described in greater detail herein. In particular embodiments, at least one, two, or three, or more immunogens from HSV-2 may be enclosed in or associated with a virus-like particle. By way of example, an immunogen may be an HSV-2 protein, such as UL19 (e.g., UL19 Upper Domain Fragment or an immunogenic fragment or variant thereof) and/or gD, (or an immunogenic fragment or variant thereof) and/or UL47 (or an immunogenic fragment or variant thereof), or may be another immunogenic fragment or region of the HSV-2 protein.

Regulatory Expression Sequences

As described herein, the recombinant expression vector comprises at least one regulatory expression sequence. In certain embodiments, when the recombinant expression vector comprises a viral vector genome, expression of the at least one immunogen is desired in particular target cells. Typically, for example, in a lentiviral vector the polynucleotide sequence encoding the immunogen is located between the 5' LTR and 3' LTR sequences. Further, the encoding nucleotide sequence(s) is preferably operatively linked in a functional relationship with other genetic or regulatory sequences or features, for example transcription regulatory sequences including promoters or enhancers, that regulate expression of the immunogen in a particular manner. In certain instances, the useful transcriptional regulatory sequences are those that are highly regulated with respect to activity, both temporally and spatially. Expression control elements that may be used for regulating the expression of the encoded polypeptides are known in the art and include, but are not limited to, inducible promoters, constitutive promoters, secretion signals, enhancers, and other regulatory sequences.

The polynucleotide encoding the immunogen and any other expressible sequence is typically in a functional relationship with internal promoter/enhancer regulatory sequences. With respect to lentiviral vector constructs, an "internal" promoter/enhancer is one that is located between the 5' LTR and the 3' LTR sequences in the viral vector and is operatively linked to the encoding polynucleotide sequence of interest. The internal promoter/enhancer may be any promoter, enhancer or promoter/enhancer combination known to increase expression of a gene with which it is in a functional relationship. A "functional relationship" and "operatively linked" mean, without limitation, that the sequence is in the correct location and orientation with respect to the promoter and/or enhancer such that the sequence of interest will be expressed when the promoter and/or enhancer is contacted with the appropriate molecules.

The choice of an internal promoter/enhancer is based on the desired expression pattern of the immunogen and the specific properties of known promoters/enhancers. Thus, the internal promoter may be constitutively active. Non-limiting examples of constitutive promoters that may be used include the promoter for ubiquitin (see, e.g., U.S. Pat. No. 5,510,474; WO 98/32869); CMV (see, e.g., Thomsen et al., Proc. Natl. Acad. Sci. USA 81:659, 1984; U.S. Pat. No. 5,168,062); beta-actin (Gunning et al. 1989 Proc. Natl. Acad. Sci. USA 84:4831-4835); and pgk (see, for example, Adra et al. 1987 Gene 60:65-74; Singer-Sam et al. 1984 Gene 32:409-417; and Dobson et al. 1982 Nucleic Acids Res. 10:2635-2637).

Alternatively, the promoter may be a tissue specific promoter. In some embodiments, the promoter is a target cell-specific promoter. Targeting dendritic cells may enhance the immune response, particularly the cellular cytotoxic response that is useful for immunity for HSV-2. For example, the promoter can be from any product expressed by dendritic cells, including CD11c, CD103, TLRs, DC-SIGN, BDCA-3, DEC-205, DCIR2, mannose receptor, Dectin-1, Clec9A, MHC class II. In addition, promoters may be selected to allow for inducible expression of the immunogen. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of each of the immunogen-encoding polynucleotide sequences. The artisan of ordinary skill will be able to select a promoter based on the desired expression pattern of the polynucleotide sequence in the organism or the target cell of interest.

A recombinant expression vector, including a viral vector genome, may comprise at least one RNA Polymerase II or III responsive promoter. This promoter can be operatively linked to the polynucleotide sequence of interest and can also be linked to a termination sequence. In addition, more than one RNA Polymerase II or III promoter may be incorporated. RNA polymerase II and III promoters are well known to persons of skill in the art. A suitable range of RNA polymerase III promoters can be found, for example, in Paule and White, Nucleic Acids Res., Vol. 28, pp 1283-1298 (2000). RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods described herein. Particularly suited Pol II or III promoters include the tetracycline responsive promoters provided in Ohkawa and Taira, Human Gene Therapy, 11:577-585 (2000) and in Meissner et al., Nucleic Acids Res., 29:1672-1682 (2001).

An internal enhancer may also be present in the recombinant expression vector, including a viral vector genome, to increase expression of the polynucleotide sequence of interest. For example, the CMV enhancer (see, e.g., Boshart et al., Cell 41:521, 1985) may be used. Many enhancers in viral genomes, such as HIV, CMV, and in mammalian genomes have been identified and characterized (see, e.g., publically available databases such as GenBank). An enhancer can be used in combination with a heterologous promoter. One of ordinary skill in the art will be able to select the appropriate enhancer based on the desired expression pattern.

When targeting delivery of a recombinant expression vector, including a viral vector genome, to a particular target cell, the vector genome will usually contain a promoter that is recognized by the target cell and that is operatively linked to the sequence of interest, viral components (when the vector is a viral vector), and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operatively linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in patents and published patent applications that can be identified by searching the U.S. Patent and Trademark Office databases.

One of skill in the art will be able to select an appropriate promoter based on the specific circumstances. Many different promoters are well known in the art, as are methods for operatively linking the promoter to the polynucleotide sequence to be expressed. Both native promoter sequences and many heterologous promoters may be used to direct expression in the packaging cell and target cell. Heterologous promoters are typically used because they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus, and Simian Virus 40 (SV40). The promoter may also be, for example, a heterologous mammalian promoter, for example, the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 base pairs in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (base pair 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

A recombinant expression construction, including a viral vector genome, may also contain additional genetic elements. The types of elements that may be included in the construct are not limited in any way and may be chosen to achieve a particular result. For example, a signal that facilitates nuclear entry of the recombinant expression vector or viral genome in the target cell may be included. An example of such a signal is the HIV-1 flap signal. Additional regulatory sequences may be included that facilitate the characterization of the provirus integration site in the target cell. For example, a tRNA amber suppressor sequence may be included in the construct. An insulator sequence, for example from chicken β-globin, may also be included in the viral genome construct. This element reduces the chance of silencing an integrated provirus in the target cell due to methylation and heterochromatinization effects. In addition, the insulator may shield the internal enhancer, promoter and exogenous polynucleotide sequences from positive or negative positional effects from surrounding DNA at the integration site on the chromosome. In addition, the recombinant construct, including the vector genome, may contain one or more genetic elements designed to enhance expression of the gene of interest. For example, a woodchuck hepatitis virus responsive element (WRE) may be placed into the construct (see, e.g., Zufferey et al. 1999. J. Virol. 74:3668-81; Deglon et al., 2000. Hum. Gene Ther. 11:179-90).

When the recombinant expression vector is a viral vector genome, the viral vector genome is typically constructed in a plasmid form that may be transfected into a packaging or producer cell line for production of the viral vector genome construct. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

In certain configurations, recombinant expression vectors contain polynucleotide sequences that encode dendritic cell (DC) maturation/stimulatory factors. Exemplary stimulatory molecules include GM-CSF, IL-2, IL-4, IL-6, IL-7, IL-15, IL-21, IL-23, TNFα, B7.1, B7.2, 4-1BB, CD40 ligand (CD40L), drug-inducible CD40 (iCD40), and the like. These polynucleotides are typically under the control of one or more regulatory elements that direct the expression of the coding sequences in dendritic cells. In certain other particular embodiments, a recombinant expression vector is excluded that directs expression of and includes a nucleotide sequence that encodes both an immunogen and GM-CSF. Maturation of dendritic cells contributes to successful vaccination (see, e.g., Banchereau et al., Nat. Rev. Immunol. 5:296-306 (2005); Schuler et al., Curr. Opin. Immunol. 15:138-147 (2003); Figdor et al., Nat. Med. 10:475-480 (2004)). Maturation can transform DCs from cells actively involved in antigen capture into cells specialized for T cell priming. For example, engagement of CD40 by CD40L on CD4-helper T cells is a critical signal for DC maturation, resulting in potent activation of CD8+ T cells. Such stimulatory molecules are also referred to as maturation factors or maturation stimulatory factors. Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics. A significant tolerance mechanism in chronic infections and cancer is the functional exhaustion of antigen-specific T cells that express high levels of PD-1. As the potency of therapeutic immunization has been shown to be significantly enhanced by combination with immune checkpoint control, as a non-limiting example, it can be appreciated by those of ordinary skill in the art that an alternative approach to inhibiting immune checkpoint is to inhibit the expression of programmed death (PD) ligands one and two (PD-L1/L2). One way to accomplish inhibition is by the expression of RNA molecules such as those described herein, which repress the expression of PD-L1/L2 in the DCs transduced with a viral vector genome, such as the lentivirus vector genome, encoding one or more of the relevant molecules. Maturation of DCs or expression of particular elements such as immune checkpoints, for example PD-1 ligands, can be characterized by flow cytometry analysis of up-regulation of surface marker such as MHC II, and by profiling expressed chemokines and cytokines, for example, by performing techniques and methods described herein.

A sequence encoding a detectable product, usually a protein, can be included to allow for identification of cells that are expressing the desired immunogen. For example, a fluorescent marker protein, such as green fluorescent protein (GFP), is incorporated into the recombinant expression construct along with a polynucleotide sequence of interest (i.e., encoding at least one immunogen). In other instances, the protein may be detectable by an antibody, or the protein may be an enzyme that acts on a substrate to yield a detectable product, or may be a protein product that allows selection of a transfected or transduced target cell, for example confers drug resistance, such as hygromycin resistance. Typical selection genes encode proteins that confer resistance to antibiotics or other toxins suitable for use in eukaryotic cells, for example, neomycin, methotrexate, blasticidin, among others known in the art, or complement auxotrophic deficiencies, or supply critical nutrients withheld from the media. The selectable marker can optionally be present on a separate plasmid and introduced by co-transfection.

With respect to vector particles described herein, one or more multicistronic expression units may be used that include two or more of a polynucleotide sequence encoding an immunogen, and a sequence encoding an envelope molecule as described herein or one or more DC maturation factors necessary for production of the desired vector particle in packaging cells. The use of multicistronic vectors reduces the total number of nucleic acid molecules required and thus may avoid the possible difficulties associated with coordinating expression from multiple vector genomes. In a multicistronic vector the various elements to be expressed are operatively linked to one or more promoters (and other expression control elements as necessary). In some configurations, a multicistronic vector comprises a sequence encoding an at least one immunogen (i.e., one or more) of interest, a sequence encoding a reporter product, and a sequence encoding one or more vector particle components. In certain embodiments in which the recombinant construct comprises a polynucleotide that encodes an immunogen, the construct optionally encodes a DC maturation factor. In certain other embodiments, a multicistronic vector comprises a polynucleotide sequences that encode each of an immunogen, a DC maturation factor, and optionally viral components when the expression vector is a viral expression vector. In still other embodiments, multicistronic vectors direct expression and encode at least two or more immunogens.

Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (see, e.g., U.S. Pat. No. 4,937,190; de Felipe et al. 2004. Traffic 5: 616-626). In one embodiment, oligonucleotides such as furin cleavage site sequences (RAKR) (see, e.g., Fang et al. 2005 Nat. Biotech. 23: 584-590) linked with 2A-like sequences from foot-and-mouth diseases virus (FMDV); equine rhinitis A virus (ERAV); and thosea asigna virus (TaV) (see, e.g., Szymczak et al. 2004 Nat. Biotechnol. 22: 589-594) are used to separate genetic elements in a multicistronic vector. The efficacy of a particular multicistronic vector can readily be tested by detecting expression of each of the genes using standard protocols.

In a specific exemplification, a viral vector genome comprises: a cytomegalovirus (CMV) enhancer/promoter sequence; the R and U5 sequences from the HIV 5' LTR; a packaging sequence (Φ); the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR (see, e.g., Iwakuma et al. Virology 15:120, 1999).

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989 and 2001 editions; Molecular Cloning: A Laboratory Manual, Cold Spring Harbor Laboratory Press, NY); Coffin et al. (Retroviruses. Cold Spring Harbor Laboratory Press, N.Y. (1997)); and "RNA Viruses: A Practical Approach" (Alan J. Cann, Ed., Oxford University Press, (2000), each of the foregoing which is incorporated herein by reference in its entirety.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the immunogen-specific polynucleotide in the expression vector. See Sambrook et al., supra, pp. 16.17-16.22, 1989. Other vectors and methods suitable for adaptation to the expression of polypeptides are well known in the art and are readily adapted to the specific circumstances.

By using the teachings provided herein and the knowledge in the art, a person skilled in the art will recognize that the efficacy of a particular expression system can be tested by transfecting packaging cells with a vector comprising a polynucleotide sequence encoding a reporter protein and measuring the expression using a suitable technique, for example, measuring fluorescence from a green fluorescent protein conjugate. Other suitable reporter genes are well known in the art.

Exemplary Embodiments

In addition to any of the foregoing embodiments described in the detailed description, embodiments are contemplated including any of the following or any combinations thereof:

1. An immunogenic, pharmaceutical composition comprising,
   (i) an envelope glycoprotein of HSV-2, or an immunological fragment thereof;
   (ii) a structural protein of HSV-2 other than an envelope glycoprotein of HSV-2, or an immunological fragment thereof;
   (iii) optionally, an agent that activates innate immunity; and
   (iv) a pharmaceutically acceptable carrier.
2. The composition of embodiment 1 wherein the envelope glycoprotein of HSV-2 is gD2.
3. The composition of embodiment 1 comprising an immunological fragment of the envelope glycoprotein gD2.
4. The composition of any of embodiments 1-3, wherein the structural protein of HSV-2 is selected from the group consisting of UL47, ICP0, UL19, UL25, UL46, UL39, UL7 and UL26.
5. The composition of embodiment 1 wherein the structural protein of HSV-2 is UL19.
6. The composition of embodiment 2 wherein the structural protein of HSV-2 is UL19.
7. The composition of embodiment 1 which comprises an immunological fragment of UL19.
8. The composition of embodiment 2 which comprises an immunological fragment of UL19, for example, SEQ ID NO 12.
9. The composition of embodiment 1 wherein the structural protein of HSV-2 is UL25.
10. The composition of embodiment 2 wherein the structural protein of HSV-2 is UL25.
11. The composition of embodiment 1 which comprises an immunological fragment of UL25.
12. The composition of embodiment 2 which comprises an immunological fragment of UL25.
13. The composition of embodiment 1 wherein the structural protein of HSV-2 is UL47.
14. The composition of embodiment 2 wherein the structural protein of HSV-2 is UL47.
15. The composition of embodiment 1 which comprises an immunological fragment of UL47.
16. The composition of embodiment 2 which comprises an immunological fragment of UL47.
17. The composition of any one of embodiments 1-16 further comprising a second structural protein of HSV-2, or an immunological fragment thereof.
18. The composition of embodiment 17 wherein the second structural protein of HSV-2 is selected from the group consisting of UL47, ICP0, UL19, UL25, UL46, UL39, UL7 and UL26, where the second structural protein is non-identical to the first structural protein.
19. The composition of embodiment 18 wherein the second structural protein is a full length protein.
20. The composition of embodiment 18 wherein the second structural protein is an immunological fragment of the second structural protein.
21. The composition of any of embodiments 5-8 further comprising UL25.
22. The composition of any of embodiments 5-8 further comprising an immunological fragment of UL25.
23. The composition of any of embodiments 5-8 further comprising UL47.
24. The composition of any of embodiments 5-8 further comprising an immunological fragment of UL47.
25. The composition of any of embodiments 9-12 further comprising UL19.
26. The composition of any of embodiments 9-12 further comprising an immunological fragment of UL19, for example, SEQ ID NO. 12.
27. The composition of any of embodiments 9-12 further comprising UL47.
28. The composition of any of embodiments 9-12 further comprising an immunological fragment of UL47.
29. The composition of any of embodiments 13-16 further comprising UL19.
30. The composition of any of embodiments 13-16 further comprising an immunological fragment of UL19, for example, SEQ ID NO. 12.
31. The composition of any of embodiments 13-16 further comprising UL25.
32. The composition of any of embodiments 13-16 further comprising an immunological fragment of UL25.
33. The composition of any of embodiments 1-32, wherein the agent is an adjuvant.
34. The composition of embodiment 33, wherein the adjuvant is GLA.
35. The composition of embodiment 1 comprising gD2; UL25; UL19; GLA adjuvant; and a pharmaceutically acceptable carrier.
36. The composition of embodiment 1 comprising gD2, UL25 and an immunological fragment of UL19, for example, SEQ ID NO. 12.
37. The composition of embodiment 1 comprising gD2, UL19, and an immunological fragment of UL25.
38. The composition of any of embodiments 35-37 further comprising UL47.
39. The composition of any of embodiments 35-37 further comprising an immunological fragment of UL47.
40. The composition of embodiment 1 comprising ICP0 or an immunological fragment thereof, and one or more of UL47 or an immunological fragment thereof, UL19 or an immunological fragment thereof, UL25 or an immunological fragment thereof, UL46 or an immunological fragment thereof, UL39 or an immunological fragment thereof, UL7 or an immunological fragment thereof, and UL26 or an immunological fragment thereof.

41. The composition of embodiment 2 comprising ICP0 or an immunological fragment thereof, and one or more of UL47 or an immunological fragment thereof, UL19 or an immunological fragment thereof, UL25 or an immunological fragment thereof, UL46 or an immunological fragment thereof, UL39 or an immunological fragment thereof, UL7 or an immunological fragment thereof, and UL26 or an immunological fragment thereof.

42. The composition of embodiments 40 or 41, comprising ICP0 or an immunological fragment thereof, and two additional structural proteins or an immunological fragment thereof.

43. The composition of embodiment 1 comprising UL46 or an immunological fragment thereof and one or more of UL47 or an immunological fragment thereof, UL19 or an immunological fragment thereof, UL25 or an immunological fragment thereof, ICP0 or an immunological fragment thereof, UL39 or an immunological fragment thereof, UL7 or an immunological fragment thereof, and UL26 or an immunological fragment thereof.

44. The composition of embodiment 2 comprising UL46 or an immunological fragment thereof and one or more of UL47 or an immunological fragment thereof, UL19 or an immunological fragment thereof, UL25 or an immunological fragment thereof, ICP0 or an immunological fragment thereof, UL39 or an immunological fragment thereof, UL7 or an immunological fragment thereof, and UL26 or an immunological fragment thereof.

45. The composition of embodiments 43 or 44, comprising UL46 or an immunological fragment thereof, and two additional structural proteins or an immunological fragment thereof.

46. A method for treating an HSV-2 infection in a subject, comprising administering the composition of any one of embodiments 1-45 to the subject.

47. A method for generating an immune response to HSV-2 in a subject, comprising administering the composition of any one of embodiments 1-45 to the subject.

48. The method of embodiment 47, wherein the subject is seropositive for HSV-2 and seropositive for HSV-1.

49. The method of embodiment 47, wherein the subject is seropositive for HSV-2 and seronegative for HSV-1.

50. A pharmaceutical composition comprising,
an antigenic portion of an envelope glycoprotein of HSV-2 and a pharmaceutically acceptable carrier, where the antigenic portion comprises a leader sequence of an envelope glycoprotein of HSV-2.

51. The composition of embodiment 50, wherein the antigenic portion binds to neutralizing antibodies.

52. The composition of embodiment 50 wherein the envelope glycoprotein of HSV-2 is gD2 or gB2.

53. The composition of embodiments 50-52 wherein the antigenic portion comprises two or more linear epitopes from the envelope glycoprotein.

54. The composition of embodiments 50-52 wherein the antigenic portion comprises two or more discontinuous epitopes from the envelope glycoprotein.

55. The composition of any of embodiments 50-54 further comprising an agent that activates innate immunity.

56. The composition of embodiment 55, wherein the agent is an adjuvant.

57. The composition of embodiment 56, wherein the adjuvant is GLA.

58. A method for treating an HSV-2 or HSV-1 infection in a subject, comprising administering the composition of any one of embodiments 50-57 to the subject.

59. A method for generating an immune response to HSV-2 or HSV-1 in a subject, comprising administering the composition of any one of embodiments 50-57 to the subject.

60. The method of embodiments 58-59, wherein the subject is seropositive for HSV-2 and seropositive for HSV-1.

61. The method of embodiments 58-59, wherein the subject is seropositive for HSV-2 and seronegative for HSV-1.

62. A kit comprising a vial comprising the composition of embodiment 50.

63. An isolated fragment of UL19 lacking at least amino acids 1-336 and 1295-1374 of SEQ ID NO: 4.

64. An isolated polypeptide comprising a fragment of UL19 consisting of SEQ ID NO: 12 or a fragment thereof.

65. The polypeptide of embodiment 64 further comprising a non-UL19 peptide fused to the fragment of UL19.

66. An isolated polypeptide comprising a peptide that consists of an amino acid sequence at least 80% identical over 50 contiguous amino acids of SEQ ID NO: 12, optionally fused to a non-UL19 peptide.

67. An immunogenic, pharmaceutical composition comprising,
(i) a polypeptide comprising the amino acid sequence of SEQ ID NO: 12 or an immunological variant or fragment thereof, or the fragment or polypeptide of any of embodiments 63-67;
(ii) an adjuvant; and
(iii) a pharmaceutically acceptable carrier.

68. The composition of embodiment 67, wherein the adjuvant is a TLR4 agonist.

Figure 1B:
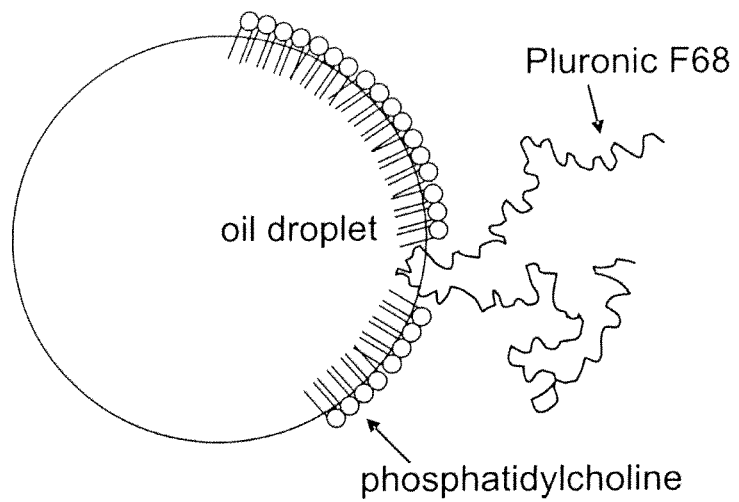

69. The composition of embodiment 68, wherein the adjuvant is GLA (FIG. 1).

70. The composition of embodiment 67 further comprising any one or more of (a) an envelope protein of HSV-2, (b) a structural protein of HSV-2 other than an envelope glycoprotein of HSV-2, or (c) an immunological fragment of (a) or (b).

71. The composition of embodiment 67, further comprising a structural protein of HSV-2.

72. The composition of embodiment 71, wherein the structural protein is selected from the group consisting of UL47, ICP0, UL25, UL46, UL39, UL7 and UL26.

73. The composition of embodiment 67 further comprising gD2, or an immunological fragment thereof, UL25, or an immunological fragment thereof, and optionally UL47, or an immunological fragment thereof.

74. An immunogenic, pharmaceutical composition comprising,
(i) an envelope glycoprotein of HSV-2, or an immunological fragment thereof;
(ii) GLA (FIG. 1); and
(iii) a pharmaceutically acceptable carrier.

75. The composition of embodiment 74, wherein the envelope glycoprotein of HSV-2 or immunological fragment thereof is gD2 or immunological fragment thereof.

76. An immunogenic, pharmaceutical composition comprising,
(i) a structural protein of HSV-2 other than an envelope glycoprotein of HSV-2, or an immunological fragment thereof;
(ii) GLA; and
(iii) a pharmaceutically acceptable carrier.

77. The composition of embodiment 76, wherein the structural protein of HSV-2 or immunological fragment thereof is selected from the group consisting of UL47, ICP0, UL19, UL25, UL46, UL39, UL7 and UL26 or an immunological fragment of any of these.

78. The composition of any one of embodiments 33, 34, 56, 57, 66, 67, and 71-77, further comprising a second adjuvant.

79. The composition of embodiment 78, wherein the second adjuvant is selected from the group consisting of a TLR agonist, e.g. a TLR7 agonist or a TLR9 agonist; alum; an emulsion; a saponin; a cytokine; an unmethylated CpG dinucleotide; and a modified saponin.

80. The composition of embodiment 78, wherein the second adjuvant is selected from the group consisting of Freund's incomplete adjuvant, MF59™, Montanide™, AS02™, AS04™, QS-21™, and ISCOM™.

81. An immunogenic, pharmaceutical composition comprising,
   (i) ICP4, or an immunological fragment thereof;
   (ii) gD2, or an immunological fragment thereof;
   (iii) GLA (FIG. 1); and
   (iii) a pharmaceutically acceptable carrier.

82. An immunogenic, pharmaceutical composition comprising,
   (i) an α group gene product of HSV-2, or an immunological fragment thereof; and/or
   (ii) a β1 gene product of HSV-2, or an immunological fragment thereof; and/or
   (iii) a β2 gene product of HSV-2, or an immunological fragment thereof; and/or
   (iv) a γ1 gene product of HSV-2, or an immunological fragment thereof; and/or
   (v) a γ2 gene product of HSV-2, or an immunological fragment thereof; and/or
   (vi) an adjuvant, preferably GLA (FIG. 1); and
   (vii) a pharmaceutically acceptable carrier.

83. The composition of any one of embodiments 1-45, 50-57, and 65-82, further comprising a surfactant.

84. A method for treating an HSV-2 infection or an HSV-1 infection in a subject, comprising administering the composition of any one of embodiments 65-83 to the subject.

85. A method for generating an immune response to HSV-2 or an HSV-1 infection in a subject, comprising administering the composition of any one of embodiments 65-83 to the subject.

86. The method of any one of embodiments 84-85, wherein the subject is seropositive for HSV-2 and seropositive for HSV-1.

87. The method of any one of embodiments 85-85, wherein the subject is seropositive for HSV-2 and seronegative for HSV-1.

88. The method of any one of embodiments 83-87 wherein the administration route is intradermal, mucosal, intramuscular, subcutaneous, sublingual, rectal, or vaginal.

89. A method for reducing transmission of HSV-2 from a subject, comprising administering the composition of any one of embodiments 1-45, 50-57, and 65-83 to the subject.

90. A method for reducing shedding of HSV-2 in a subject, comprising administering the composition of any one of embodiments 1-45, 50-57, and 65-83 to the subject.

91. A method for reducing the frequency of lesions in a subject with an HSV-2 infection, comprising administering the composition of any one of embodiments 1-45, 50-57, and 65-83 to the subject.

92. A method for reducing the risk of contracting HIV in a subject with an HSV-2 infection, comprising administering the composition of any one of embodiments 1-45, 50-57, and 65-83 to the subject.

93. A method for inducing sterilizing immunity to HSV-2 in a subject, comprising administering the composition of any one of embodiments 1-45, 50-57, and 65-83 to the subject.

94. A kit comprising the composition of any one of embodiments 1-45, 50-57, and 65-83.

95. The kit of embodiment 94, further comprising an attenuated HSV1 or HSV2 virus.

96. The kit of embodiment 94, further comprising an inactivated HSV1 or HSV2 virus.

97. The kit of embodiment 94, further comprising a viral vector comprising a polynucleotide encoding an HSV1 or HSV2 antigen.

98. The kit of embodiment 94, further comprising a virus-like particle comprising a polynucleotide encoding an HSV1 or HSV2 antigen.

99. The kit of embodiment 94, further comprising a polynucleotide encoding an HSV1 or HSV2 antigen.

100. The composition of any one of embodiments 1-45, wherein the envelope glycoprotein and/or structural protein is fused to a heterologous peptide.

101. The method of any one of embodiments 58-61 and 84-93, further comprising administering a polynucleotide encoding an HSV1 and/or HSV2 antigen.

102. The method of embodiment 101, wherein the polynucleotide is a part of the genome of a viral vector.

103. The method of any one of embodiments 58-61 and 84-93, further comprising administering an inactivated or attenuated HSV1 or HSV2 virus.

104. The method of any one of embodiments 58-61 and 84-93, further comprising administering a virus-like particle comprising a polynucleotide encoding an HSV1 or HSV2 antigen.

105. An immunogenic, pharmaceutical composition comprising,
   (i) a first polynucleotide encoding an envelope glycoprotein of HSV-2, or an immunological fragment thereof;
   (ii) a second polynucleotide encoding a structural protein of HSV-2 other than an envelope glycoprotein of HSV-2, or an immunological fragment thereof;
   (iii) optionally an agent that activates innate immunity, such as an adjuvant; and
   (iv) a pharmaceutically acceptable carrier.

106. The composition of embodiment 105 wherein the envelope glycoprotein of HSV-2 is gD2.

107. The composition of embodiment 105 comprising an immunological fragment of the envelope glycoprotein gD2.

108. The composition of any of embodiments 105-107, wherein the structural protein of HSV-2 is selected from the group consisting of UL47, ICP0, UL19, UL25, UL46, UL39, UL7 and UL26.

109. The composition of any of embodiments 105-107 wherein the structural protein of HSV-2 or immunological fragment thereof is UL19 or an immunological fragment thereof.

110. The composition of any of embodiments 105-107 wherein the second polynucleotide encodes UL19.

111. The composition of any of embodiments 105-107 wherein the second polynucleotide encodes an immunological fragment of UL19, optionally the fragment or polypeptide of any one of embodiments 63-66.

112. The composition of any of embodiments 105-107 wherein the second polynucleotide encodes SEQ ID NO 12.

113. The composition of any of embodiments 105-107 wherein the structural protein of HSV-2 or immunological fragment thereof is UL25 or an immunological fragment thereof.

114. The composition of any of embodiments 105-107 wherein the second polynucleotide encodes UL25.

115. The composition of any of embodiments 105-107 wherein the second polynucleotide encodes an immunological fragment of UL25.

116. The composition of any of embodiments 105-107 wherein the structural protein of HSV-2 or immunological fragment thereof is UL47 or an immunological fragment thereof.

117. The composition of any one of embodiments 105-116 further comprising a third polynucleotide encoding a second structural protein of HSV-2, or an immunological fragment thereof.

118. The composition of embodiment 117 wherein the second structural protein of HSV-2 is selected from the group consisting of UL47, ICP0, UL19, UL25, UL46, UL39, UL7 and UL26, and wherein the second structural protein is non-identical to the first structural protein.

119. The composition of embodiment 118 wherein the second structural protein is a full length protein or an immunological fragment thereof.

120. The composition of any of embodiments 100-112 further comprising a polynucleotide encoding UL25 or an immunological fragment thereof.

121. The composition of any of embodiments 106-109 further comprising a polynucleotide encoding UL47 or an immunological fragment thereof.

122. The composition of any of embodiments 113-115 further comprising a polynucleotide encoding UL19.

123. The composition of any of embodiments 113-115 further comprising a polynucleotide encoding SEQ ID NO. 12.

124. The composition of any of embodiments 113-115 further comprising a polynucleotide encoding UL47 or an immunological fragment thereof.

125. The composition of embodiment 116 further comprising a polynucleotide encoding UL19.

126. The composition of any of embodiments 116 further comprising a polynucleotide encoding SEQ ID NO. 12.

127. The composition of any of embodiments 116 further comprising a polynucleotide encoding UL25 or an immunological fragment thereof.

128. The composition of any of embodiments 105-127, wherein the agent is an adjuvant, optionally a TLR4 agonist.

129. The composition of embodiment 128, wherein the adjuvant is GLA.

130. The composition of embodiment 105, wherein the first polynucleotide encodes gD2; the second polynucleotide encodes UL25; and wherein the composition further comprises a third polynucleotide encoding UL19; GLA adjuvant; and a pharmaceutically acceptable carrier.

131. The composition of embodiment 105 wherein the first polynucleotide encodes gD2, the second polynucleotide encodes UL25, and wherein the composition further comprises a polynucleotide encoding SEQ ID NO. 12.

132. The composition of embodiment 105 wherein the first polynucleotide encodes gD2, the second polynucleotide encodes UL19, wherein the composition further comprises a polynucleotide encoding an immunological fragment of UL25.

133. The composition of any of embodiments 130-132 further comprising a polynucleotide encoding UL47 or an immunological fragment thereof.

134. The composition of embodiment 105 or 106 comprising a polynucleotide encoding ICP0 or an immunological fragment thereof, and one or more of a polynucleotide encoding UL47 or an immunological fragment thereof, UL19 or an immunological fragment thereof, UL25 or an immunological fragment thereof, UL46 or an immunological fragment thereof, UL39 or an immunological fragment thereof, UL7 or an immunological fragment thereof, and UL26 or an immunological fragment thereof.

135. The composition of embodiment 134, comprising a polynucleotide encoding ICP0 or an immunological fragment thereof, and two additional structural proteins or an immunological fragment thereof.

136. The composition of embodiment 105 or 106 comprising a polynucleotide encoding UL46 or an immunological fragment thereof and one or more of a polynucleotide encoding UL47 or an immunological fragment thereof, UL19 or an immunological fragment thereof, UL25 or an immunological fragment thereof, ICP0 or an immunological fragment thereof, UL39 or an immunological fragment thereof, UL7 or an immunological fragment thereof, and UL26 or an immunological fragment thereof.

138. The composition of embodiments 136, comprising a polynucleotide encoding UL46 or an immunological fragment thereof, and polynucleotides encoding two additional structural proteins or an immunological fragment thereof.

139. An immunogenic, pharmaceutical composition comprising,
(i) a first polynucleotide encoding a polypeptide comprising the amino acid sequence of SEQ ID NO: 12 or an immunological variant or fragment thereof;
(ii) optionally an agent that activates innate immunity, such as an adjuvant; and
(iii) a pharmaceutically acceptable carrier.

140. The composition of embodiment 139, wherein the agent is an adjuvant.

141. The composition of embodiment 140, wherein the adjuvant is GLA.

142. The composition of embodiment 139 further comprising a second polynucleotide encoding a structural protein of HSV-2 other than an envelope glycoprotein of HSV-2, or an immunological fragment thereof.

143. The composition of embodiment 139, further comprising a third polynucleotide encoding a structural protein of HSV-2 in addition to UL19(ud).

144. The composition of embodiment 143, wherein the structural protein is selected from the group consisting of UL47, ICP0, UL25, UL46, UL39, UL7 and UL26.

145. An immunogenic, pharmaceutical composition comprising,
(i) a first polynucleotide encoding an envelope glycoprotein of HSV-2, or an immunological fragment thereof;
(ii) GLA; and
(iii) a pharmaceutically acceptable carrier.

146. The composition of embodiment 145, wherein the envelope glycoprotein of HSV-2 is gD2.

147. An immunogenic, pharmaceutical composition comprising,
(i) a first polynucleotide encoding a structural protein of HSV-2 other than an envelope glycoprotein of HSV-2, or an immunological fragment thereof;
(ii) GLA; and
(iii) a pharmaceutically acceptable carrier.

148. The composition of embodiment 147, wherein the structural protein of HSV-2 is selected from the group consisting of UL47, ICP0, UL19, UL25, UL46, UL39, UL7 and UL26.

149. The composition of any one of embodiments 105149, further comprising a second adjuvant.

150. The composition of embodiment 149, wherein the second adjuvant is selected from the group consisting of a TLR agonist, alum, an emulsion, a saponin, a cytokine, an unmethylated CpG dinucleotide, and a modified saponin.

151. The composition of embodiment 149, wherein the second adjuvant is selected from the group consisting of Freund's incomplete adjuvant, MF-59™, Montanide™, AS02™, AS04™, QS-21™, and ISCOM™.

152. An immunogenic, pharmaceutical composition comprising,
(i) a first polynucleotide encoding ICP4, or an immunological fragment thereof;
(ii) a second polynucleotide encoding gD2, or an immunological fragment thereof;
(iii) GLA; and
(iii) a pharmaceutically acceptable carrier.

153. An immunogenic, pharmaceutical composition comprising,
(i) a first polynucleotide encoding an immediate early gene product of HSV-2, or an immunological fragment thereof;
(ii) a second polynucleotide encoding an early gene product of HSV-2, or an immunological fragment thereof;
(iii) a third polynucleotide encoding a late gene product of HSV-2, or an immunological fragment thereof; and
(iv) a pharmaceutically acceptable carrier.

154. The composition of any one of embodiments 105-153, further comprising a surfactant.

155. The composition of any one of embodiments 105-154, wherein the polynucleotides are present in one or more recombinant expression vectors.

156. The composition of embodiment 155, wherein the recombinant expression vector is a viral vector or a virus-like particle.

157. A method for treating an HSV-2 or HSV-1 infection in a subject, comprising administering the composition of any one of embodiments 105-156 to the subject and co-administering a second composition comprising an adjuvant.

158. The method of embodiment 157, wherein the adjuvant is a TLR4 agonist.

159. The method of embodiment 158, wherein the TLR4 agonist is GLA.

160. A method for generating an immune response to HSV-2 or HSV-1 in a subject, comprising administering the composition of any one of embodiments 105-156 to the subject and co-administering a second composition comprising an adjuvant.

161. The method of embodiment 160, wherein the adjuvant is a TLR4 agonist.

162. The method of embodiment 161, wherein the TLR4 agonist is GLA.

163. The composition of any one of embodiments 1-45, 50-57, and 66-83, further comprising a virus-like particle, wherein the virus-like particle comprises the envelope glycoprotein of HSV-2 or immunological fragment thereof and the structural protein of HSV-2 other than an envelope glycoprotein of HSV-2 or immunological fragment thereof of any one of embodiments 1-45; the antigenic portion of an envelope glycoprotein of HSV-2 of any one of embodiments 50-57; the fragment of UL19 of any one of embodiments 63-65; the polypeptide of any one of embodiments 66-73; the envelope glycoprotein of HSV-2 or immunological fragment thereof of any one of embodiments 74-75; the structural protein of HSV-2 of any one of embodiments 76-77; or the ICP4 or immunological fragment thereof and the gD2 or immunological fragment thereof of embodiment 81.

164. A method for treating an HSV-2 infection or an HSV-1 infection in a subject, comprising a priming step comprising administering an attenuated live HSV virus to the subject and a boosting step comprising administering the composition of any one of embodiments 1-45, 50-57, 66-83 and 105-156 to the subject.

165. A method for generating an immune response to HSV-2 or an HSV-1 infection in a subject, comprising a priming step comprising administering an attenuated live HSV virus to the subject and a boosting step comprising administering the composition of any one of embodiments 1-45, 50-57, 66-83 and 105-156 to the subject.

166. A method for treating an HSV-2 infection or an HSV-1 infection in a subject, comprising a priming step comprising administering the composition of any one of embodiments 1-45, 50-57, 66-83 and 105-156 to the subject and a boosting step comprising administering an attenuated live HSV virus to the subject.

167. A method for generating an immune response to HSV-2 or an HSV-1 infection in a subject, comprising a priming step comprising administering the composition of any one of embodiments 1-45, 50-57, 66-83 and 105-156 to the subject and a boosting step comprising administering an attenuated live HSV virus to the subject.

The following examples are offered by way of illustration, and not by way of limitation.

EXAMPLES

Example 1

Enhancement of CD4 T Cell-Based Immunogenicity Against HSV-2 GD2 Protein when Formulated with the Adjuvant GLA-SE Following Multiple Vaccinations in Mice In this example, the ability of GLA-SE to augment CD4 T cell responses following immunization of mice with a recombinant protein vaccine was assessed.

Figure 2:
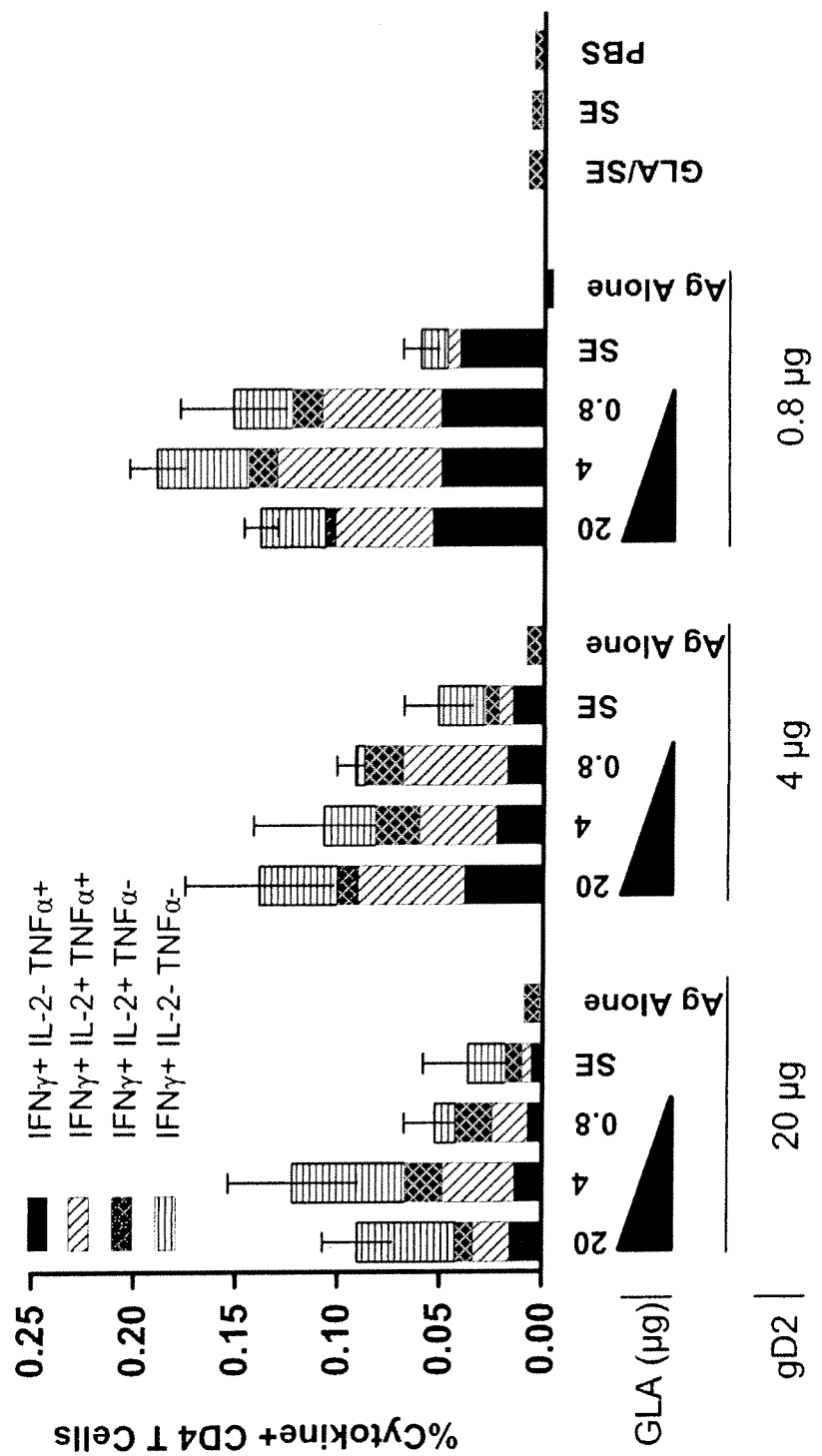
FIG. 2 shows gD2-specific CD4 T cell responses. Data were obtained after Balb/c mice (4/group) were immunized twice i.m. at a 28 day interval with a bivalent vaccine comprised of varying levels of recombinant protein and GLA, as indicated. The graphs are results of flow cytometry analyses for intracellular production of IL-2, TNF-$\alpha$, and IFN-$\gamma$.

Groups of five Balb/c mice were immunized via a prime/boost immunization regimen (d0 prime/d21 boost) with either 0.8, 4, or 20 µg of recombinant gD protein in combination with either 0.8, 4, or 20 µg of GLA-SE (SE percentage is 2% in this and all following studies), SE alone, or PBS, delivered intramuscularly in 100 µl (50 µl each leg). Mice immunized with GLA-SE, SE alone, or PBS in the absence of recombinant protein served as negative controls. Antigen-specific splenic CD4 T cell responses were measured on day 4 post-boost by Intracellular Cytokine Staining (ICS) for IFN-γ, TNF-α, and IL-2 after ex-vivo re-stimulation of splenocyte cultures for 5 hours with $gD_{272-285}$ peptide, which had previously been identified as a CD4 T cell epitope in gD2 that is presented in mice with the H-2d haplotype. As depicted in FIG. 2, a CD4 T cell response to immunization with each dose of gD2 recombinant protein was observed only when either GLA-SE or SE was included as an adjuvant. At each dose of recombinant gD2 antigen and at each dose of GLA-SE, the magnitude of the gD2-specific CD4 T cell response was increased over the response observed to the same amount of recombinant gD2 antigen formulated with SE alone. In addition, the quality of the responding antigen-specific CD4 T cell population, as measured by the frequency of IFN-γ+, TNF-α+, and IL-2+ CD4 T cells (triple positive) within the responding CD4 T cell population was increased at each dose of recombinant gD2 protein and at each dose of GLA over that observed when gD2 was formulated with SE alone. The data from this study indicate that the formulation of the adjuvant GLA-SE with recombinant HSV-2 protein antigen substantially increases the performance of the vaccine over that which is achieved by immunizing with recombinant protein alone or recombinant protein formulated with SE alone as measured by both the magnitude and quality of the cellular immune response.

Example 2

GLA Augments CD8 T Cell Responses 1N Mice

In this example, the ability of GLA-SE to augment CD8 T cell responses was assessed following immunization of mice with a recombinant protein vaccine.

Ovalbumin was used as a model protein. Female C57Bl/6 mice were injected s.c. with lentivirus-encoding ovalbumin ("LV-OVA" in FIGS. 3 and 4) and boosted by i.m. injection on day 21 with recombinant ovalbumin adjuvanted with various doses of GLA-SE ("OVA+GLA/SE" in FIGS. 3 and 4). Four days later, splenic T cell responses were measured by intracellular cytokine staining (ICS) to the following in vitro stimulants: OVA MHC Class I peptides 55-62 and 257-264 and MHC Class II peptide 323-339, or antibodies to CD3 and to CD28. CD8 T cells are identified as those secreting any of the cytokines, IFN-γ, IL-2, and TNF-α

Figure 3:
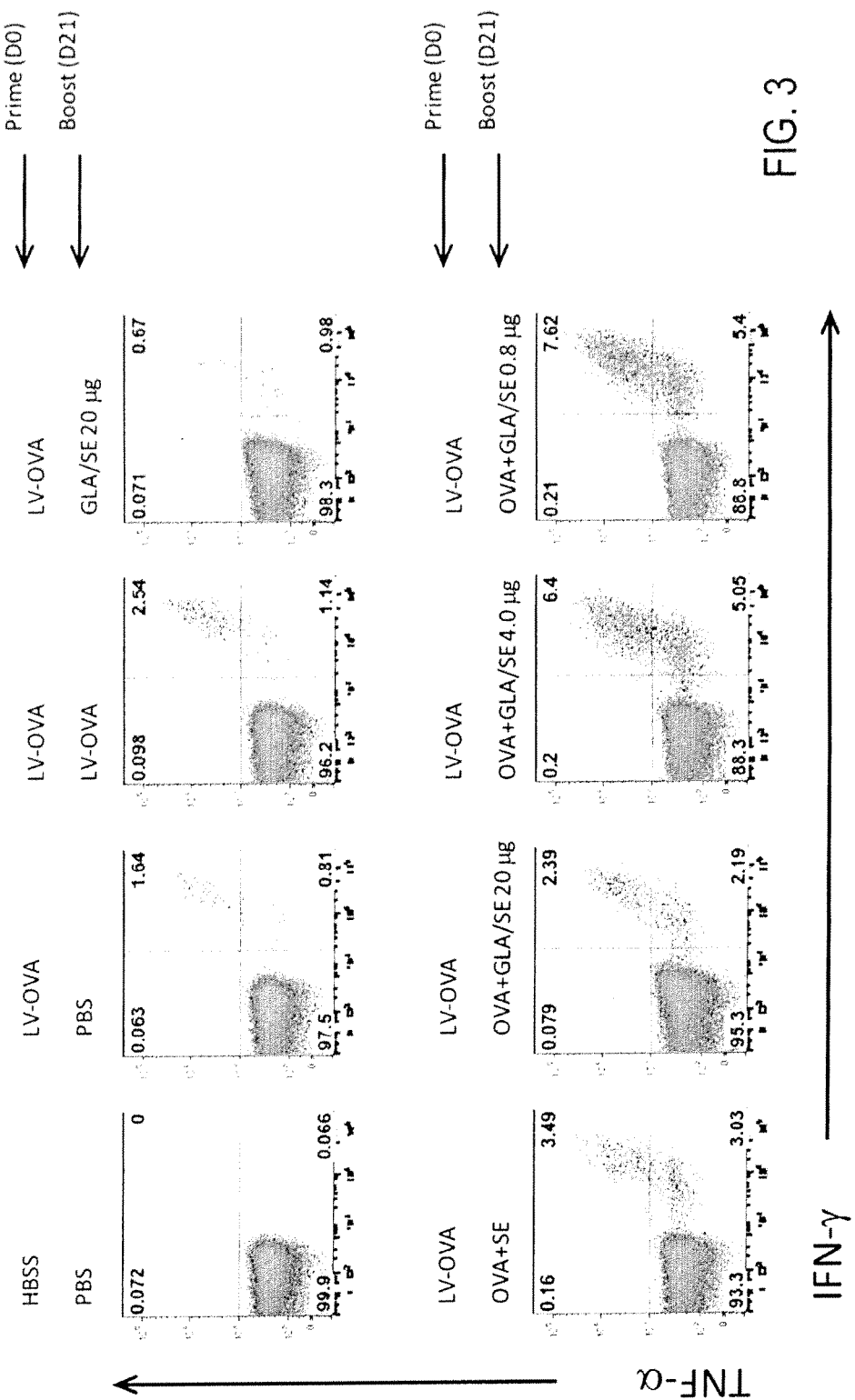
FIG. 3 shows splenic CD8 T cell responses to OVA257 peptide analyzed on D25 post-prime (D4 post-Boost); recombinant OVA=5 µg; SE=2%; lentivirus delivered s.c.; recombinant OVA delivered i.m.
Figure 4:
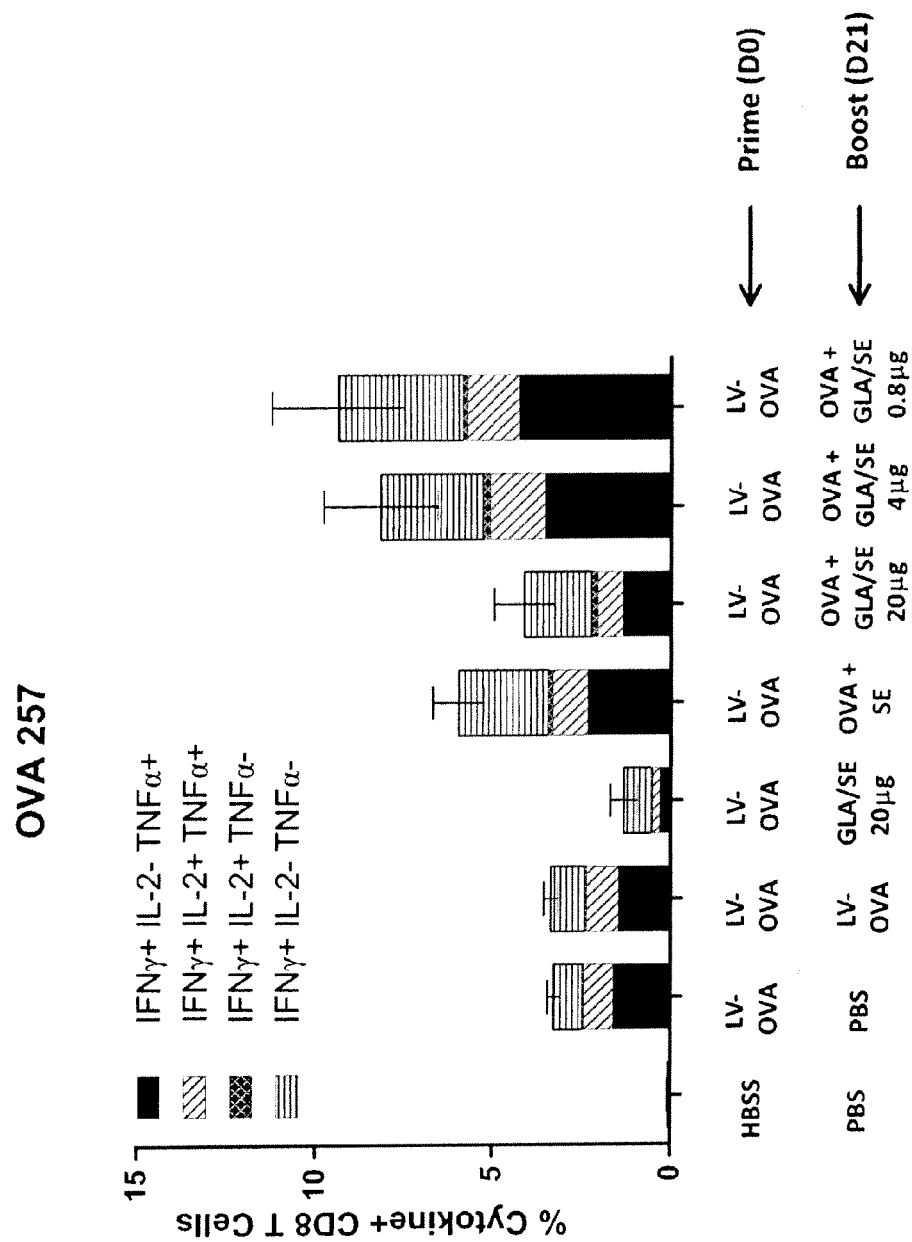
FIG. 4 is a graph showing percent cytokine positive CD8 T cells measured 4 days after a boost. Priming took place on day 0 and boosting on day 21. Column HAL d0 HBSS, d21, PBS; HA2, d0, LV-OVA, d21, PBS; HA3, d0 LV-OVA, d21 LV-OVA; HA4, d0 LV-OVA, d21 20 µg GLA-SE; HA5, d0 LV-OVA, d21 OVA+SE; HA6, d0 LV-OVA, d21 OVA+20 µg GLA-SE; HA7, d0 LV-OVA, d21, 4 µg OVA+GLA-SE; HA8, d0 LV-OVA, d21 OVA+0.8 µg GLA-SE.

As shown in FIG. 3, there was a higher percentage of CD8 T cells in mice that received a boost of antigen, with the highest percentages in mice that received GLA-SE with the antigen in the boost. FIG. 4 provides experimental detail of the ratios of four subsets of CD8 T cells. Therefore, an i.m. vaccine 'boost' with recombinant OVA protein+GLA-SE boosted pre-existing CD8 T cells that had been generated via previous LV vaccination. The mid (4 µg) and low (0.8 µg) doses of GLA provided the highest increase of CD8 T cells under these experimental settings. Therefore, these data show that GLA adjuvanted protein can be used to boost a pre-existing CD8 memory T cell response specific for the protein. Activation of CD8 memory cells is considered to be a desirable property of a therapeutic vaccine against HSV-2 for treatment of infected individuals, underscoring the superior properties GLA adjuvanted protein may confer to an HSV-2 vaccine.

Example 3

Figure 5A:
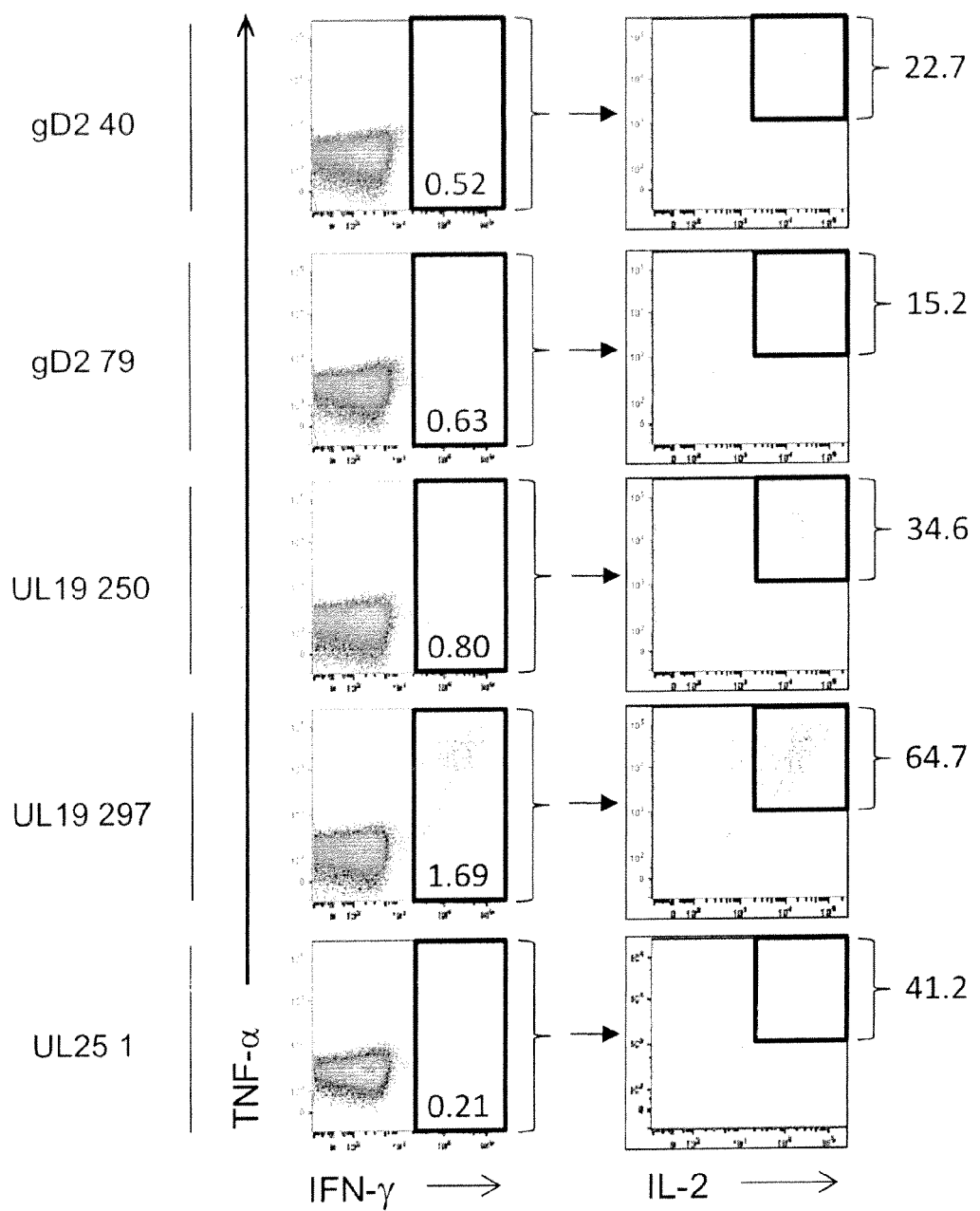
FIGS. 5A-B show data obtained after groups of C57BL/6 mice (5/group) were immunized via a prime/boost immunization regimen (d0 prime/d21 boost) with either 5 µg of recombinant gD, UL19, or UL25 protein in combination with 5 µg of GLA-SE. Splenic CD4 T cell responses were measured on day 4 post-boost by intracellular staining for IFN-$\gamma$, TNF-$\alpha$, and IL-2 after ex vivo re-stimulation with 15-mer peptides previously identified as containing CD4 T cell epitopes for the corresponding recombinant protein immunogen. A) Representative ICS dot plot of the CD4 T cell response to each 15-mer peptide indicated in mice immunized with the corresponding recombinant protein immunogen. B) Percent cytokine positive CD4 T cells are depicted for each group.
Figure 5B:
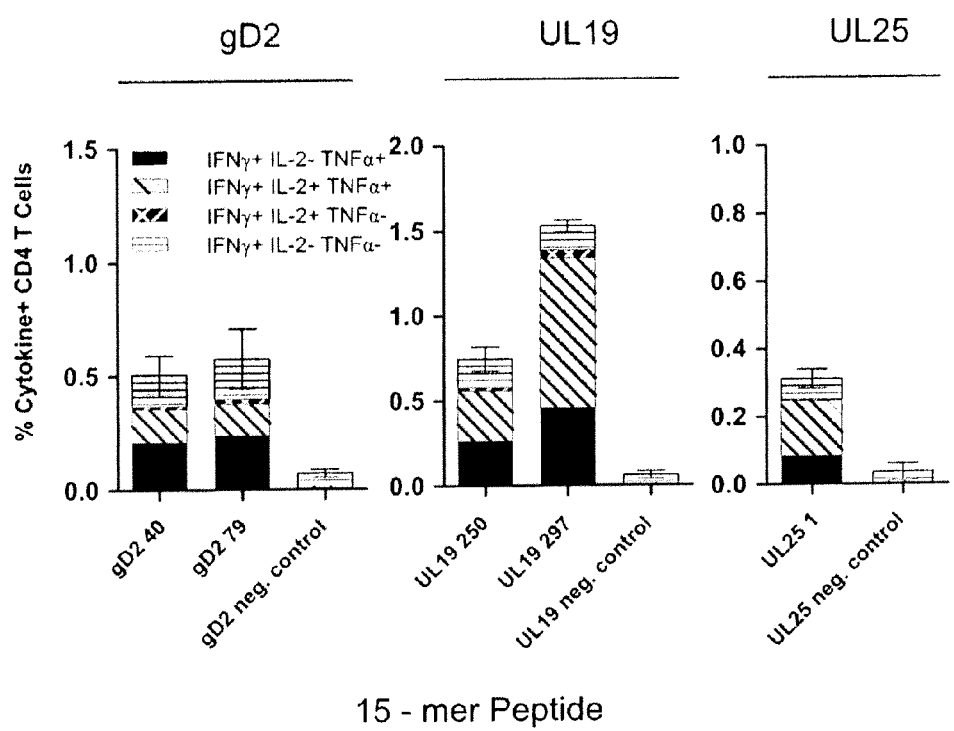

CD4 T Cell-Based Immunogenicity Against Individual HSV-2 GD2, UL19, and UL25 Proteins Following Multiple Vaccinations in Mice The goal of this set of studies was to identify a single mouse strain in which the CD4 T cell-based immunogenicity against each protein subunit in the vaccine could be evaluated. To this end, a series of experiments were conducted in mice to identify individual CD4 T cell epitopes within each HSV-2 antigen (i.e. gD2, UL19, and UL25) within the context of different MHC haplotypes (i.e. BALB/c (H-2$^d$), C57BL/6 (H-2$^b$), and CB6F1 (H-2$^d$+2$^b$)). The experimental strategy consisted of the immunization of naïve mice with 5 µg of each recombinant protein antigen as a monovalent immunogen formulated with 5 µg GLA-SE intramuscularly in 100 µl (50 µl each leg) within the context of a prime/boost immunization regimen (d0 prime/d21 boost). Antigen-specific CD4 T cell responses were analyzed on day 4 post-boost using 15-mer peptide libraries (11 aa overlap between peptides) whose sequence was derived from the corresponding amino acid sequence of the monovalent immunogen. In the primary screens, splenic CD4 cells were analyzed for the production of IFN-γ, TNF-α, and IL-2 in response to the ex vivo simulation of splenocytic cultures with pools of individual 15-mer peptides from the peptide library that corresponded to the individual HSV-2 encoded antigen. Observed CD4 T cell responses in the peptide pools were considered to be positive hits, and secondary (and in some cases tertiary) screens were subsequently conducted with an identical immunization and analysis strategies using either individual peptides within the positive pools from the previous screen as ex vivo stimulates or peptides within the positive pools from the previous screen re-pooled in different combinations. As shown in FIGS. 5A-B, these studies identified individual 15-mer peptides against which an antigen-specific CD4 T cell response could be observed for each of the individual recombinant HSV-2 proteins within the vaccine (i.e. gD2, UL19, and UL25) within the context of the MHC haplotype H-2b (C57BL/6 mice).

Example 4

Figure 6A:
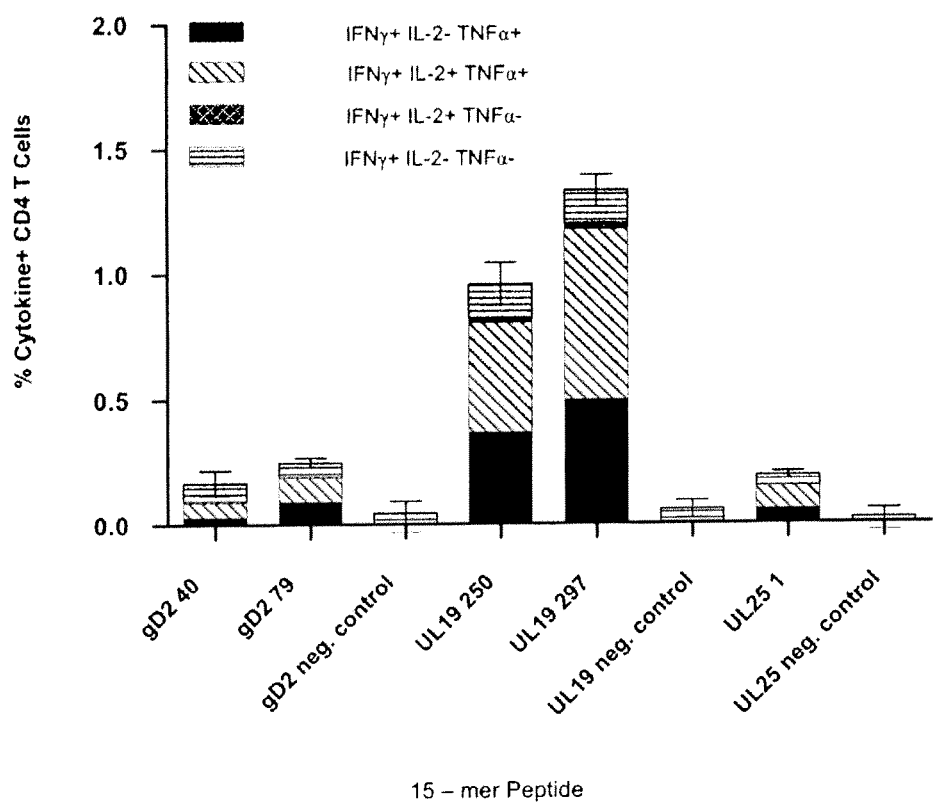
FIGS. 6 A-B show data obtained after a group of five C57BL/6 mice were immunized via a prime/boost regimen (d0 prime/d21 boost) with recombinant gD, UL19, and UL25 proteins delivered in combination and formulated on an equimolar basis (0.8, 3.3, and 1.4 µg of protein, respectively) in combination with 5.5 µg of GLA-SE. Splenic CD4 T cell responses were measured on day 4 post-boost by intracellular staining for IFN-$\gamma$, TNF-$\alpha$, and IL-12 after ex vivo restimulation with 15-mer peptides previously identified as containing CD4 T cell epitopes for each recombinant protein immunogen. An individual peptide which lacks a CD4 T cell epitope from each peptide library was included as a negative control. A) percent cytokine positive CD4 T cells are depicted for each group. B) Serum endpoint titers (defined as the reciprocal of the highest serum dilution that is >2 times background) for antigen-specific antibodies of the IgG1 subclass for each recombinant protein immunogen within the trivalent vaccine.
Figure 6B:
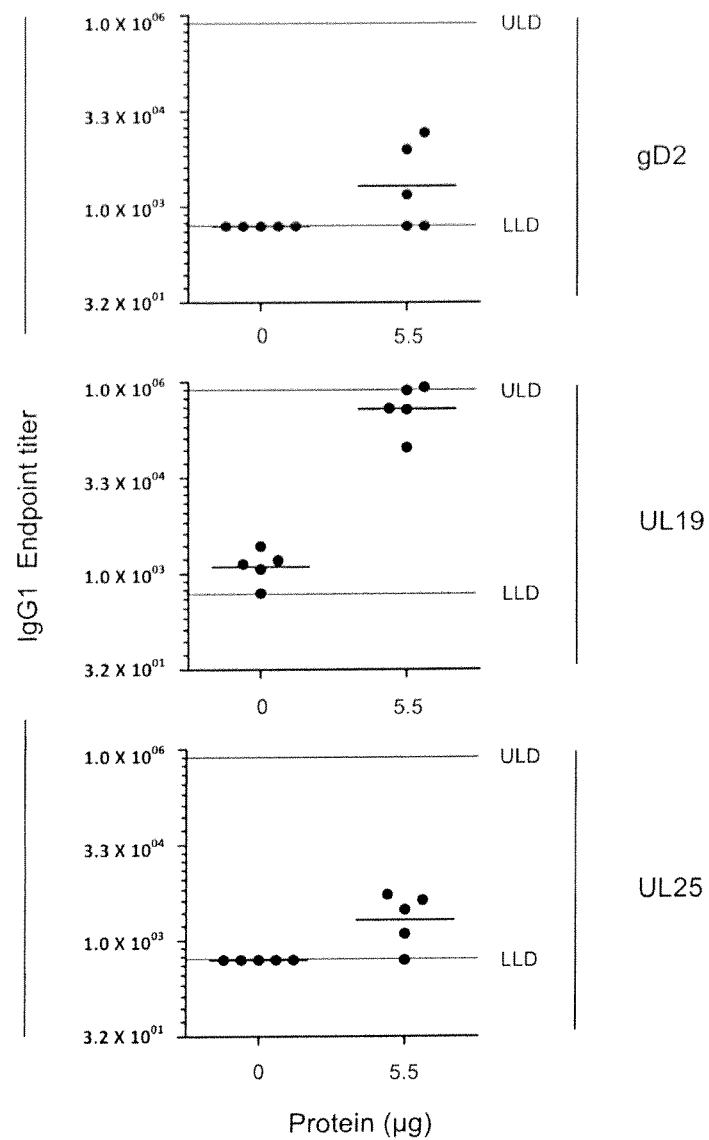

CD4 T and B Cell-Based Immunogenicity Against Each Individual HSV-2 Subunit Protein Following Multiple Vaccinations of a Trivalent Formulation in Mice This example demonstrates the CD4 T cell and B cell-based immunogenicity against each of the individual recombinant protein subunits within the vaccine when they are delivered together as a trivalent formulation with GLA-SE in C57BL/6 mice. The experimental strategy consisted of using two groups of five C57BL/6 mice. One group was immunized via a prime/boost immunization regimen (d0 prime/d21 boost) with recombinant HSV-2 gD2, UL19, and UL25 proteins delivered in combination and formulated on an equi-molar basis (0.8, 3.3, and 1.4 µg of protein, respectively) in combination with 5.5 µg of GLA-SE delivered intramuscularly in 100 µl (50 µl each leg). The second group was mock immunized with vehicle (PBS). The animals were sacrificed on day 4 post-boost for the harvesting of the spleens and peripheral blood (via cardiac puncture). Antigen-specific splenic CD4 T cell responses were measured by ICS for IFNγ, TNFα, and IL-2 after the ex vivo re-stimulation of splenocyte cultures with the 15-mer peptides previously identified as containing CD4 T cell epitopes for each recombinant protein immunogen within the trivalent vaccine (see Example 3). The serum of each vaccinated and mock vaccinated mouse was analyzed for the presence of antigen-specific antibodies of the IgG1 subclass against each of the recombinant protein immunogens within the trivalent vaccine by direct ELISA. As shown in FIGS. 6A-B, antigen-specific CD4 T cell and antibody responses were observed to each of the HSV-2 recombinant protein antigens when delivered together as a trivalent formulation with GLA-SE. These data support the significant immunogenicity of the trivalent vaccine and its ability to elicit a comprehensive immune response (both humoral and cellular) against HSV-2 proteins. Unexpectedly, the magnitude of the immune responses generated were greatest for the UL19 antigen. UL19 has never been included as a component of any of the prior recombinant subunit-based vaccines administered for the treatment or prevention of HSV-2 infection in humans. These data provide evidence that the claimed vaccines display superior properties over the prior art vaccines.

Example 5

Figure 7A:
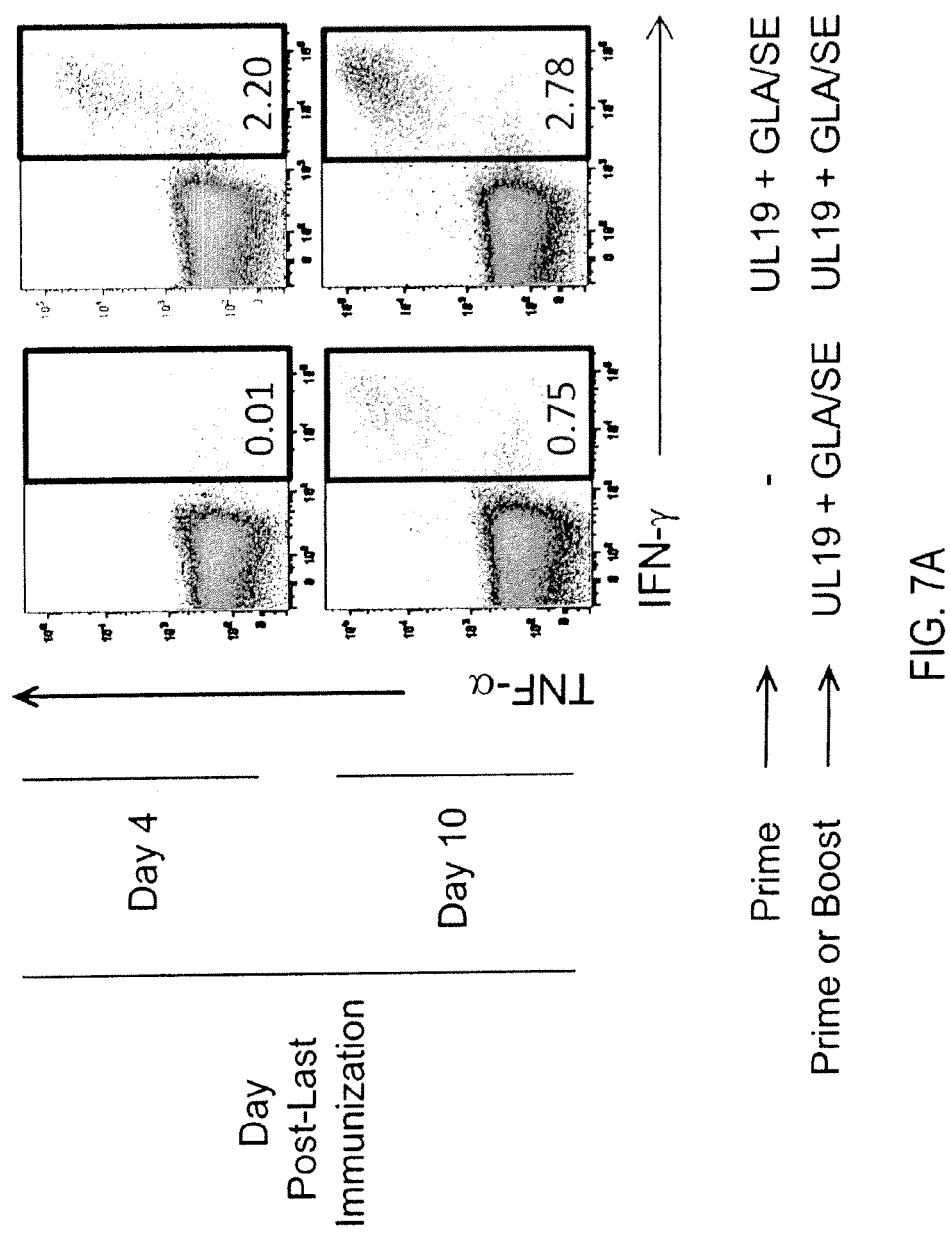
FIGS. 7 A-B show data obtained when groups of C57BL/6 mice (5/group) were immunized via a prime (d0) or prime boost (d0 prime/d21 boost) immunization regimen with 5 µg recombinant UL19 protein delivered in combination with 5 µg of GLA-SE. Splenic CD4 T cell responses were measured on day 4 or day 10 post-last immunization by ICS for IFN-$\gamma$, TNF-$\alpha$, and IL-12 after ex vivo re-stimulation with 15-mer peptides previously identified as containing CD4 T cell epitopes for UL19. A) Representative ICS dot plots of the CD4 T cell response to UL19 15-mer peptide 297 indicated in mice immunized with the corresponding recombinant protein immunogen. Percent cytokine positive DC4 T cells are depicted for each group. B) Percent cytokine positive CD4 T cells responding to UL19 15-mer 250 or 297 are depicted for each group.
Figure 7B:
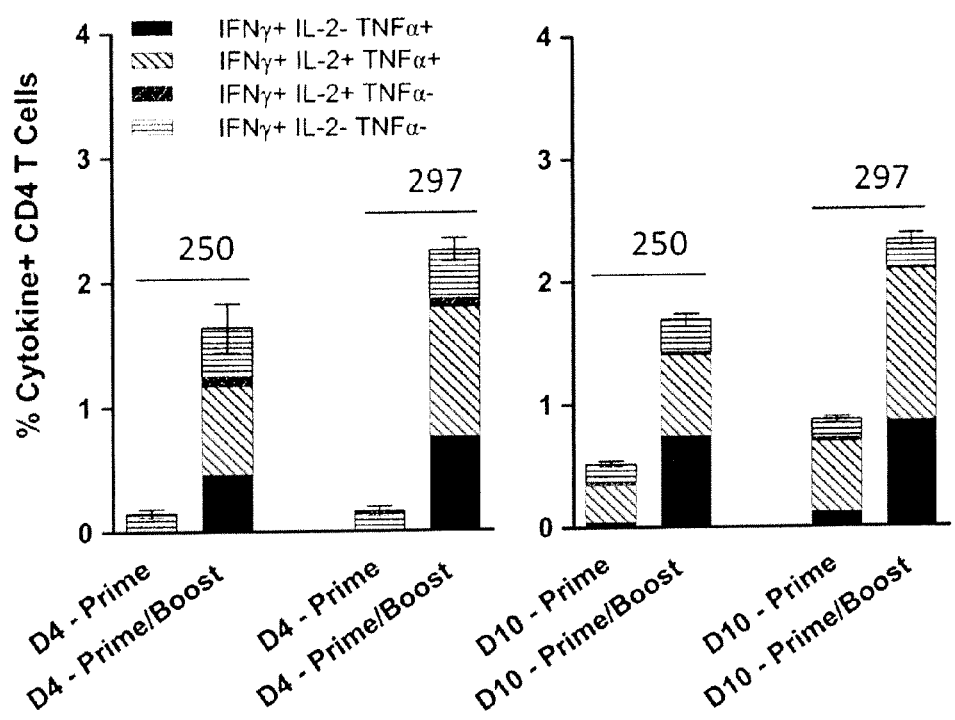
Figure 8A:
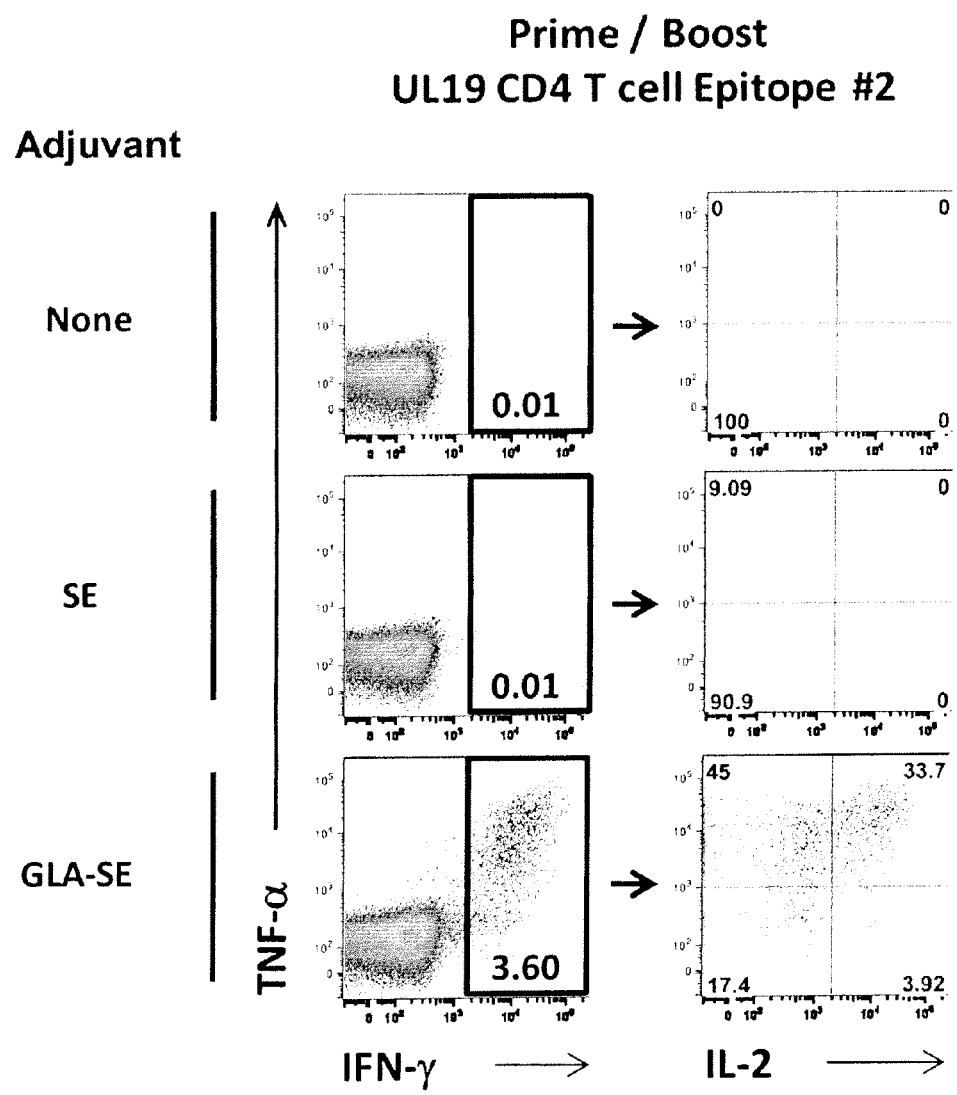
FIGS. 8A-B show data obtained when groups of C57BL/6 mice (5/group) were immunized via a prime (d0) or prime boost (d0 prime/d21 boost) immunization regimen with 5 µg recombinant UL19 protein delivered alone or in combination with 5 µg of SE or GLA-SE. Splenic CD4 T cell responses were measured on day 5 or day 10 post-last immunization by ICS for IFN-$\gamma$, TNF-$\alpha$, and IL-12 after ex vivo re-stimulation with 15-mer peptides previously identified as containing CD4 T cell epitopes for UL19. A) Representative ICS dot plots of the CD4 T cell response to UL19 15-mer peptide 297 indicated in mice immunized with the corresponding recombinant protein immunogen. Percent cytokine positive CD4 T cells are depicted for each group. B) Percent cytokine positive CD4 T cells responding to UL19 15-mer 250 or 297 are depicted for each group.
Figure 8B:
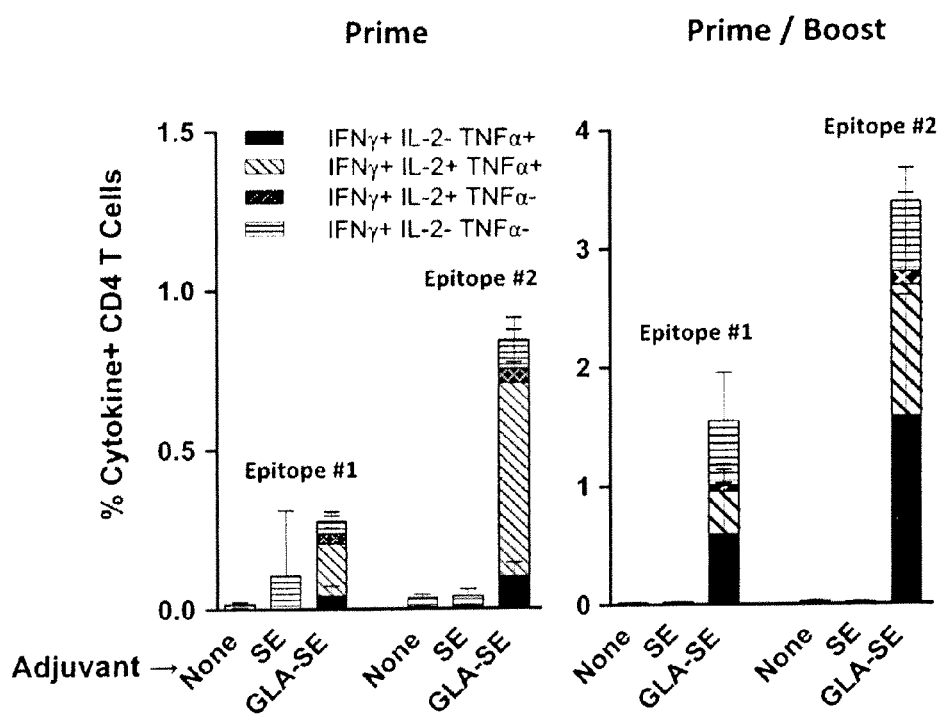

Antigen-Specific Cd4 T Cell Responses Following Single and Multiple Immunizations of HSV-2 UL19 with GLA-SE in Mice This Example shows the CD4 T cell-based immunogenicity generated by single and repeat immunizations of HSV-2 UL19 formulated with GLA-SE in mice. For this study, two groups of five C57BL/6 mice received one immunization and two groups of five c57BL/6 mice received two immunizations (separated by 21 days) with 5 µg of recombinant UL19 protein antigen as a monovalent immunogen with 5 µg GLA-SE. The groups of mice were sacrificed at either day 4 or 10 after the final immunization for the analysis of antigen-specific CD4 T cell responses. The immunizations that the respective analysis groups received were staggered in time such that all four groups of mice were sacrificed on the same day for the analysis of the antigen-specific CD4 T cell response. The antigen-specific CD4 T cell response to the immunogen was measured by the production of IFN-γ, TNF-α, and IL-2 in response to the ex vivo stimulation of splenocytes with the individual UL19 15-mer peptides numbers 250 and 297 that had been previously identified as containing CD4 T cell epitopes specific for UL19 (see Example 3). As depicted in FIGS. 7A-B, at day four post-last immunization UL19-specific CD4 T cell responses were only detected in animals that received two immunizations, whereas UL19-specific CD4 T cell responses were detected at day 10 post-last immunization within both the prime and the prime/boost arms of the experiment. At day 10 post-last immunization, the magnitude of the response was markedly increased (~2.5 fold) in the animals that received two immunizations as compared to those that received only a single immunization. These findings show that repeat administration of a vaccine containing a recombinant HSV-2 protein+GLA-SE is a superior protocol for increasing the response and the magnitude of the ensuing antigen-specific CD4 T cell response To test the dependence of the increase in the CD4 T cell response following repeat administration of the vaccine on GLA-SE, a similar experiment was performed in which groups of mice were immunized with UL19 protein alone or protein formulated with SE alone, or GLA-SE. The groups of mice were sacrificed at either day 5 or 10 post final immunization for the analysis of antigen-specific CD4 T cell responses. The antigen-specific CD4 T cell response to the immunogen was measured by the production of IFN-γ, TNF-α, and IL-2 in response to the ex vivo stimulation of splenocytes with the individual UL19 15-mer peptides numbers 250 and 297 that had been previously identified as containing CD4 T cell epitopes specific for UL19 (see Example 3). As depicted in FIGS. 8A-B, animals that received two immunizations as compared to those that received only a single immunization displayed a significant increase in the antigen-specific CD4 T cell response, confirming the results of the previous experiment. Importantly, this increase was found to be dependent upon the GLA-SE adjuvant as mice receiving two immunizations displayed no significant CD4 T cell responses when the immunogen was administered alone or with SE in the absence of GLA.

Example 6

Figures 9A, 9B, 9C:
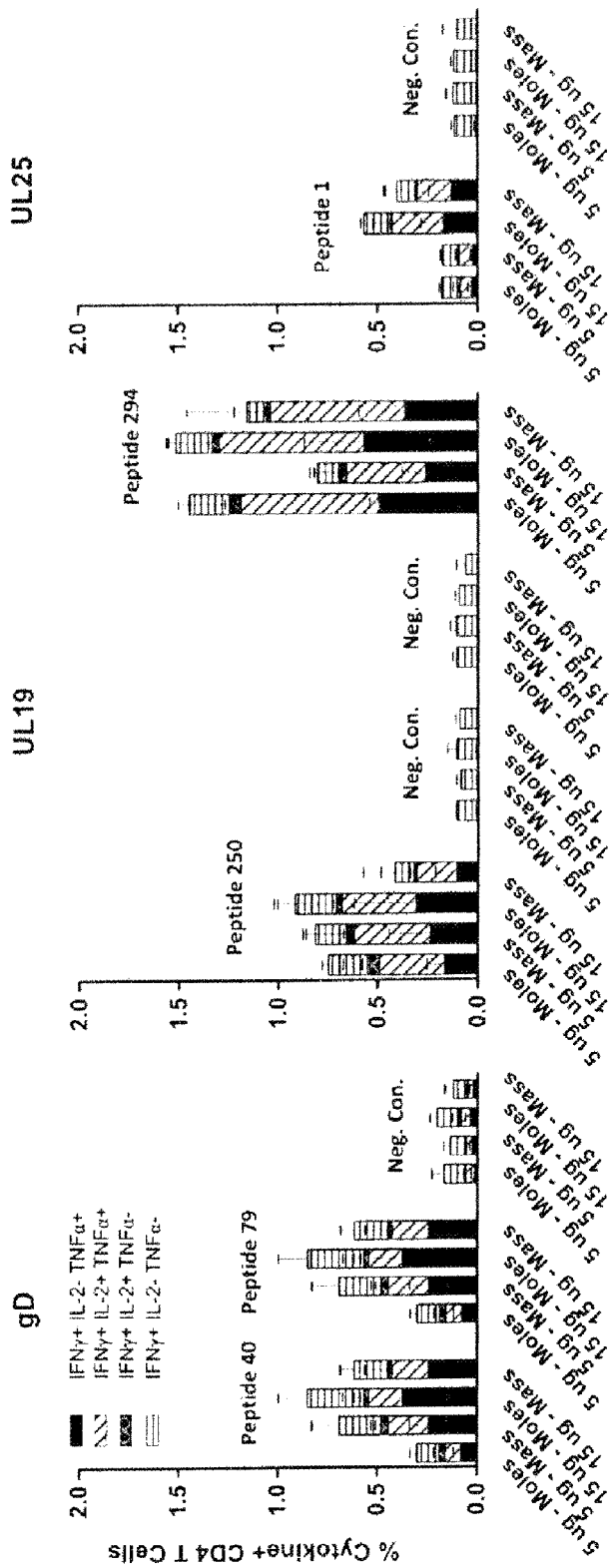
FIGS. 9A-C show data obtained when groups of C57BL/6 mice (5/group) were immunized via a prime boost (d0 prime/d21 boost) immunization regimen with recombinant proteins formulated on either an equimolar or an equimass basis. Total protein delivered was either 5 µg or 15 µg. Splenic CD4 T cell responses were measured on day 5 post-last immunization by intracellular staining for IFN-$\gamma$, TNF-$\alpha$, and IL-12 after ex vivo re-stimulation with 15-mer peptides previously identified as containing CD4 T cell epitopes. A) Percent cytokine positive CD4 T cells responding to gD peptides are depicted. B) Percent cytokine positive CD4 T cells responding to UL19 peptides are depicted. C) Percent cytokine positive CD4 T cells responding to UL25 peptides are depicted.

Antigen-Specific Cd4 T Cell Responses Following Immunization with Trivalent HSV Vaccine Formulated with GLA-SE in Mice This Example shows that CD4 T cell responses can be generated against each subunit of a trivalent subunit vaccine comprising the gD2, UL19, and UL25 antigens formulated in GLA-SE when the recombinant proteins are formulated on an equi-molar as well as an equi-mass basis. Groups of female C57BL/6 mice (5 mice/group) were immunized with a trivalent vaccine wherein the total protein was either 5 µg or 15 µg on either an equi-molar or an equi-mass basis. Mice received a second immunization with a homologous formulation at day 21 and T cell responses were measured after ex vivo restimulation with an appropriate peptide by ICS five days following the last immunization. As shown in FIG. 9, epitope-specific CD4 T cell responses are generated against each individual component of the trivalent HSV-2 subunit vaccine. Positive responses were observed despite whether the recombinant protein components are formulated on an equi-molar or an equi-mass basis, indicating that the responses are not significantly impacted or altered based on relative protein composition of the vaccine.

Example 7

Enhancement of Antibody-Based Immunogenicity Against HSV-2 GD2 Protein when Formulated with the Adjuvant GLA-SE Following Multiple Vaccinations in Mice In this example, the ability of GLA-SE to augment CD4 T cell responses following immunization of mice with a recombinant protein vaccine was assessed.

Figure 10:
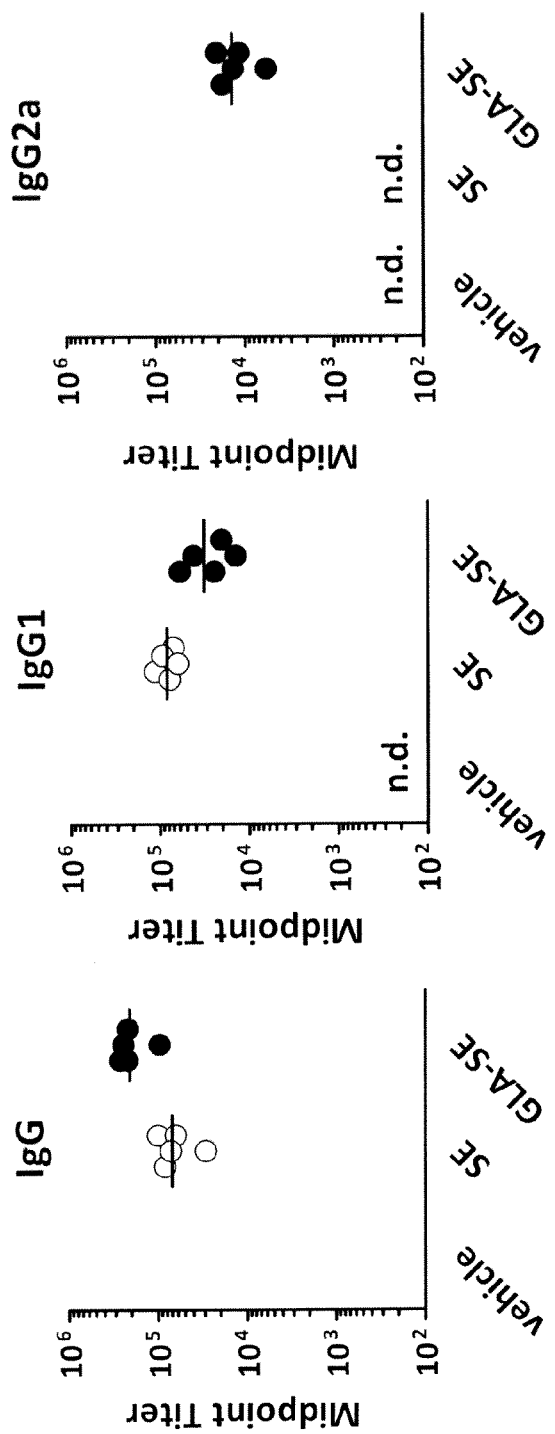
FIG. 10 shows data obtained when groups of BALB/c mice (5/group) were immunized via a prime/boost immunization regimen (d0 prime/d21 boost) with 4 µg of recombinant gD protein in combination with either 4 µg of GLA-SE, SE alone, or PBS vehicle, delivered intramuscularly in 100 µl (50 µl per leg). HSV-2 gD2-specific antibodies of the IgG, IgG1, and IgG2a isotypes were measured by ELISA.

Groups of five Balb/c mice were immunized via a prime/boost immunization regimen (d0 prime/d21 boost) with 4 µg of recombinant gD protein in combination with either 4 µg of GLA-SE, SE alone, or PBS vehicle, delivered intramuscularly in 100 µl (50 µl per leg). HSV-2 gD2-specific antibodies of the IgG, IgG1, and IgG2a isotypes were measured by ELISA. As depicted in FIG. 10, GLA-SE adjuvant enhanced the total IgG response against HSV-2 gD2, reduced the production of antigen-specific IgG1, and increased the production of antigen-specific IgG2a.

Example 8

Enhancement of CD8 T Cell-Based Immunogenicity Against HSV-2 UL19UD Protein when Formulated with the Adjuvant GLA-SE In this example, the ability of GLA-SE to induce functional HSV-2 UL19-specific CD8 T cell responses following immunization of mice with a trivalent vaccine containing recombinant HSV-2 gD2, UL19 upper domain (UL19ud; SEQ ID NO:12), and UL25 was assessed.

Figure 11:
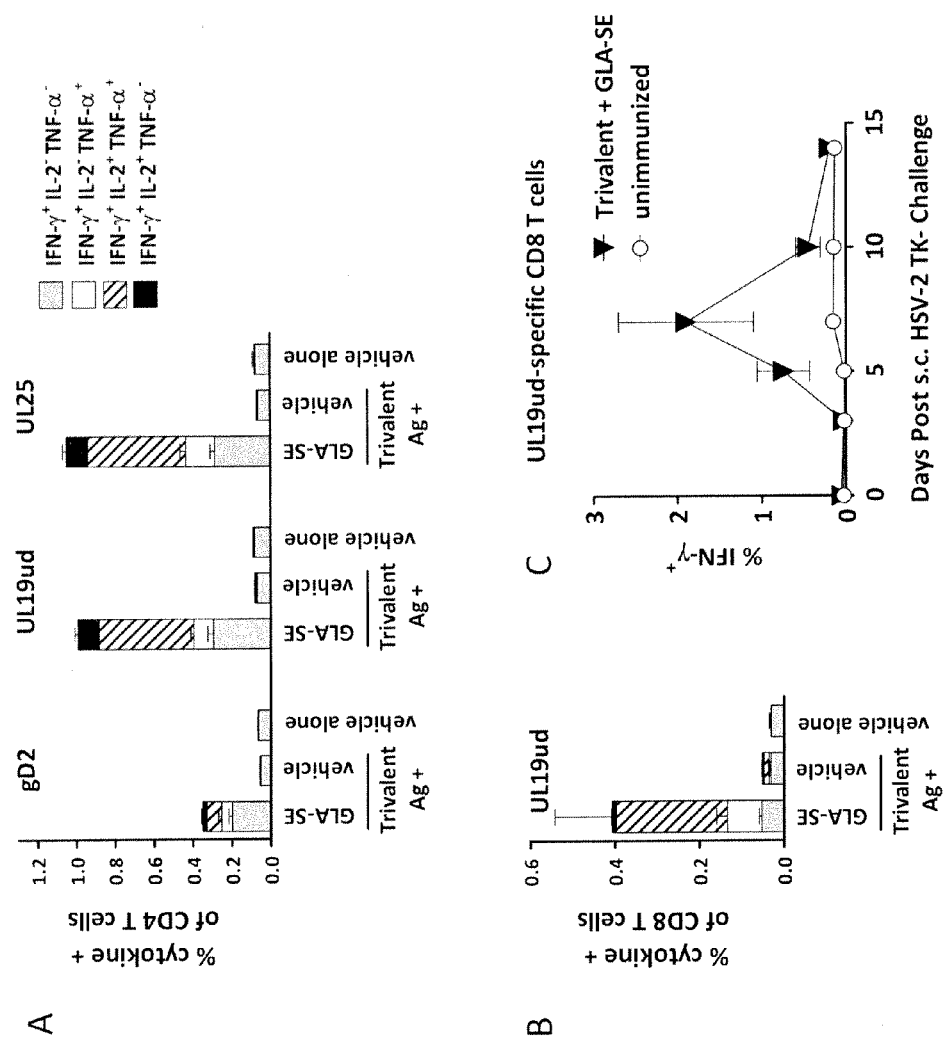
FIG. 11 shows data obtained when groups of five C57BL/6 mice were given a single intramuscular immunization of trivalent vaccine consisting of 5 µg each of recombinant gD2, UL19ud, and UL25 in combination with 5 µg GLA-SE or control vaccine articles. Antigen-specific splenic CD4 and CD8 T cell responses were measured on day 6 post-immunization by Intracellular Cytokine Staining (ICS) for IFN-$\gamma$, TNF-$\alpha$, and IL-2 after ex-vivo re-stimulation of splenocyte cultures for 5 hours with gD2, UL19, or UL25 peptides. A) Frequency and cytokine phenotype of CD4 T cells responding to peptides from gD2, UL19ud, or UL25. B) Frequency and cytokine phenotype of CD8 T cells responding to UL19 peptides. C) Frequency of CD8 T cells responding to UL19 peptides in mice that were immunized 4 weeks earlier with trivalent vaccine with GLA-SE and challenged subcutaneously with attenuated HSV-2 thymidine kinase-deficient (TK-) virus.

Groups of five C57BL/6 mice were given a single intramuscular immunization of trivalent vaccine consisting of 514 each of recombinant gD2, UL19ud, and UL25 in combination with either 5 µg GLA-SE or 5% dextrose vehicle. Mice immunized with vehicle alone served as negative controls. Antigen-specific splenic CD4 and CD8 T cell responses were measured on day 6 post-immunization by Intracellular Cytokine Staining (ICS) for IFN-γ, TNF-α, and IL-2 after ex-vivo re-stimulation of splenocyte cultures for 5 hours with gD2, UL19, or UL25 peptides. As depicted in FIG. 11, panel A, a CD4 T cell response to each component of the trivalent vaccine (gD2, UL19ud, and UL25) was observed when GLA-SE was included as an adjuvant. Notably, as depicted in FIG. 11, panel B, a CD8 T cell response was observed against the UL19ud antigen when given with GLA-SE. Confirming that these CD8 T cells are functional, mice that were unimmunized or immunized 4 weeks earlier with trivalent vaccine with GLA-SE were challenged subcutaneously with attenuated HSV-2 thymidine kinase-deficient (TK-) virus and UL19-specific CD8 T cell responses were measured by ICS. As depicted in FIG. 11, panel C, the magnitude of the CD8 T cell response upon viral challenge was greater in mice previously immunized with vaccine.

Example 9

Enhancement of Prophylactic Antiviral Efficacy of Recombinant HSV-2 Protein Vaccine when Formulated with the Adjuvant GLA-SE In this example, the ability of GLA-SE to enhance the ability of a bivalent recombinant HSV-2 protein vaccine to protect against lethal HSV-2 challenge was assessed.

Figure 12:
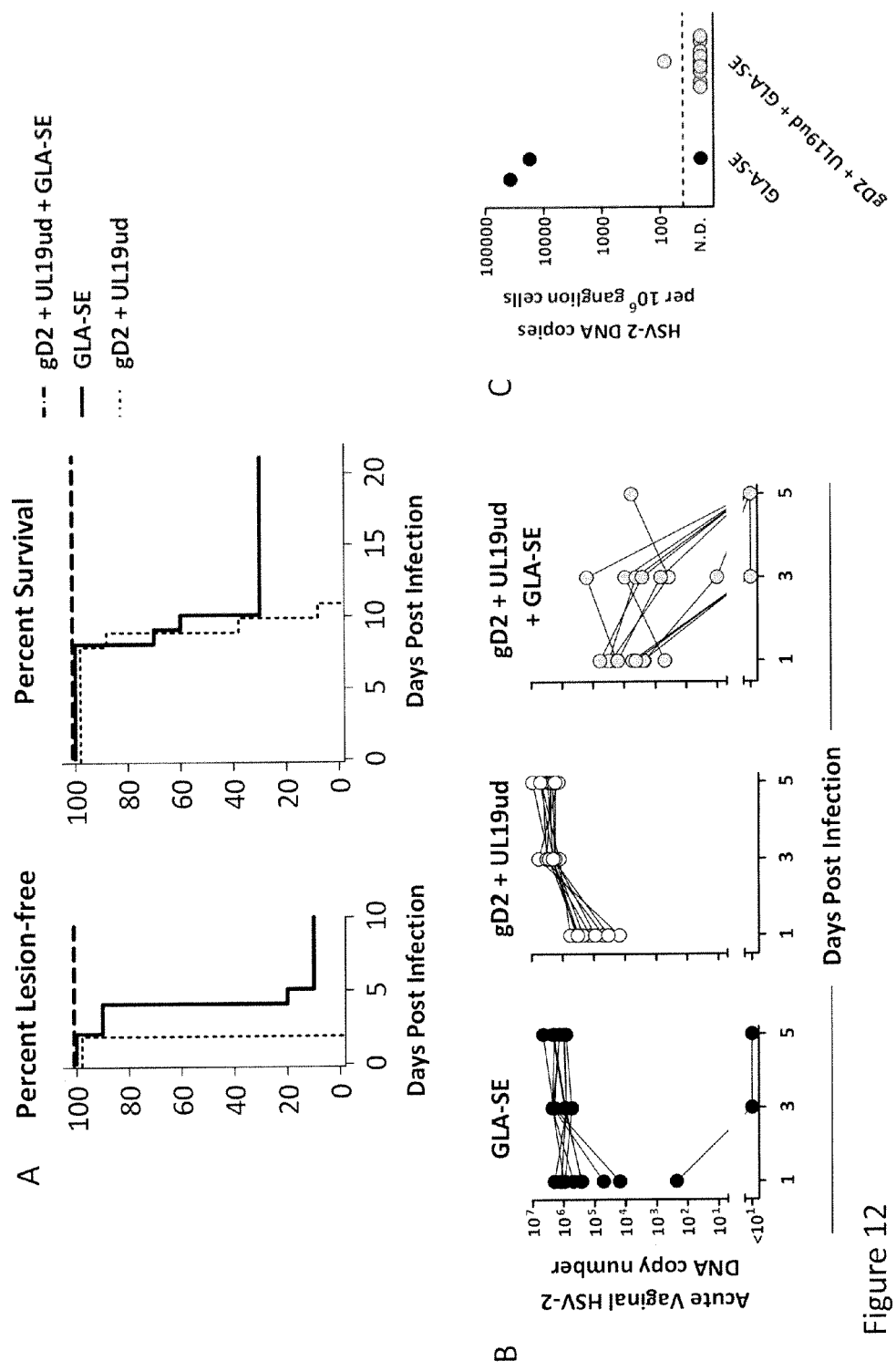
FIG. 12 shows data obtained when groups of ten C57BL/6 mice were given two intramuscular immunizations, separated by 28 days, of bivalent vaccine consisting of 5 µg each of recombinant gD2 and UL19ud in combination with either 5 µg GLA-SE or 5% dextrose vehicle. Mice immunized with 5 µg GLA-SE alone served as negative controls. 22 days after the second immunization, mice were treated with depot medroxyprogesterone acetate and then challenged six days later with a 50×LD$_{50}$ dose of wild-type HSV-2 intravaginally. Mice monitored daily for formation of genital lesions and survival. On days 1, 3, and 5 post infection, vaginal swabs were collected for quantitation of HSV-2 DNA by PCR. Approximately 2 months post infection, the dorsal root ganglia were harvested from surviving mice and latent HSV-2 DNA was quantified by PCR. As depicted in FIG. 12, panel A, mice immunized with gD2 and UL19ud with GLA-SE has dramatically reduced lesion formation and increased survival compared to mice immunized with either gD2 and UL19ud alone or GLA-SE alone. Likewise, as depicted in FIG. 12, panel B, 9 out of 10 mice immunized with gD2 and UL19ud with GLA-SE had no detectable HSV-2 DNA by day 5, whereas mice in either control group showed sustained levels of HSV-2 in the vagina through day 5. As depicted in FIG. 12, panel C, though there were three survivors in the GLA-SE only group, 2 out of 3 of these mice showed significant levels of latent HSV-2 in the dorsal root ganglia, mice immunized with gD2 and UL19ud with GLA-SE showed little to no detectable HSV-2 in the ganglia.

Groups of ten C57BL/6 mice were given two intramuscular immunizations, separated by 28 days, of bivalent vaccine consisting of 5 μg each of recombinant gD2 and UL19ud in combination with either 5 μg GLA-SE or 5% dextrose vehicle. Mice immunized with 5 μg GLA-SE alone served as negative controls. 22 days after the second immunization, mice were treated with depot medroxyprogesterone acetate and then challenged six days later with a 50×LD$_{50}$ dose of wild-type HSV-2 intravaginally. Mice monitored daily for formation of genital lesions and survival. On days 1, 3, and 5 post infection, vaginal swabs were collected for quantitation of HSV-2 DNA by PCR. Approximately 2 months post infection, the dorsal root ganglia were harvested from surviving mice and latent HSV-2 DNA was quantified by PCR. As depicted in FIG. 12, panel A, mice immunized with gD2 and UL19ud with GLA-SE has dramatically reduced lesion formation and increased survival compared to mice immunized with either gD2 and UL19ud alone or GLA-SE alone. Likewise, as depicted in FIG. 12, panel B, 9 out of 10 mice immunized with gD2 and UL19ud with GLA-SE had no detectable HSV-2 DNA by day 5, whereas mice in either control group showed sustained levels of HSV-2 in the vagina through day 5. As depicted in FIG. 12, panel C, though there were three survivors in the GLA-SE only group, 2 out of 3 of these mice showed significant levels of latent HSV-2 in the dorsal root ganglia, mice immunized with gD2 and UL19ud with GLA-SE showed little to no detectable HSV-2 in the ganglia.

Example 10

Enhancement of Expansion of Pre-Existing Memory Cd8 T Cells by Recombinant HSV-2 Protein Vaccine when Formulated with the Adjuvant GLA-SE In this example, the ability of GLA-SE to enhance the ability of a trivalent recombinant HSV-2 protein vaccine to expand memory CD8 T cells previously induced by HSV-2 infection was assessed.

Figure 13:
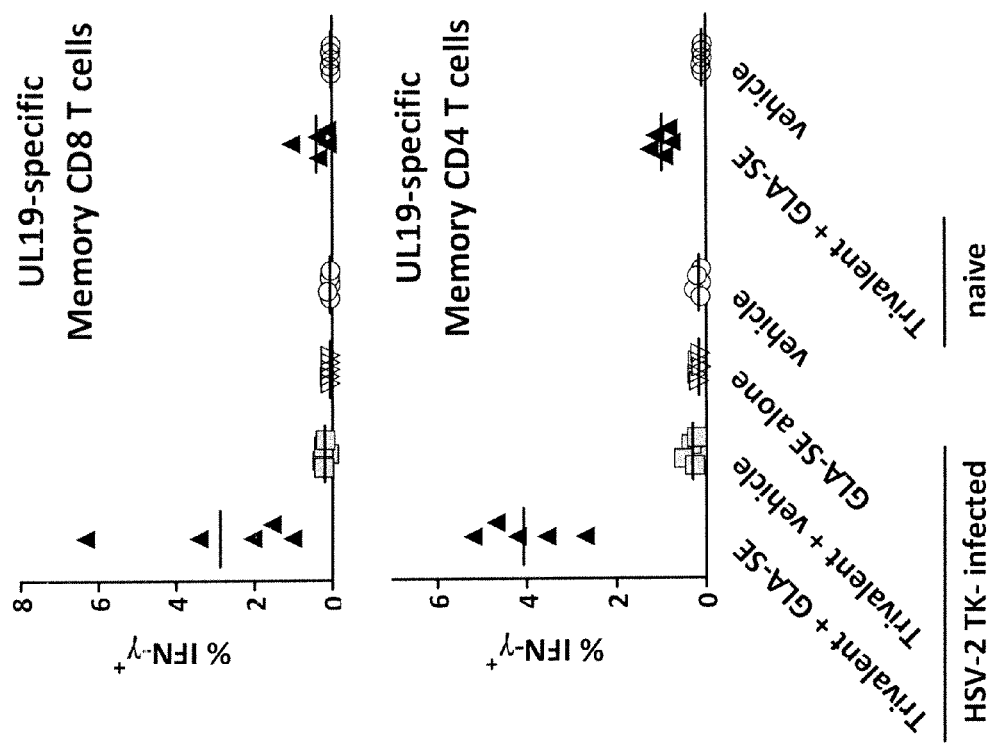
FIG. 13 shows data obtained when C57BL/6 mice (5/group) were infected subcutaneously with a sublethal dose of attenuated HSV-2 thymidine kinase-deficient (TK-) virus, then immunized 28 days later with a trivalent vaccine consisting of 5 µg each of recombinant gD2, UL19ud, and UL25 in combination with 5 µg GLA-SE or 5% dextrose vehicle. Control groups included infected mice treated with GLA-SE alone or vehicle alone, as well as naïve mice treated with vehicle alone. Six days post immunization, UL19-specific CD8 (upper panel) and CD4 (lower panel) T cell responses were measured by ICS after stimulation with UL19 peptides.

Groups of five C57BL/6 mice were infected subcutaneously with a sublethal dose of attenuated HSV-2 thymidine kinase-deficient (TK-) virus. 28 days later, infected or uninfected mice were immunized with a trivalent vaccine consisting of 5 μg each of recombinant gD2, UL19ud (SEQ ID NO:12), and UL25 in combination with 5 μg GLA-SE or 5% dextrose vehicle. Control groups included infected mice treated with GLA-SE alone or vehicle alone, as well as naïve mice treated with vehicle alone. Six days post immunization, UL19-specific CD4 and CD8 T cell responses were measured by ICS. As depicted in FIG. 13, the frequency of UL19-specific CD4 and CD8 T cells was greater after immunization of previously infected mice, indicating that there was recall of infection-induced memory T cells. Importantly, maximum expansion of these memory T cells by recombinant protein vaccine required the presence of GLA-SE adjuvant.

Example 11

Ability of a Recombinant HSV-2 Protein Vaccine to Treat Recurrent HSV-2 in Guinea Pigs In this example, the ability of a trivalent recombinant HSV-2 protein vaccine to reduce the frequency of recurrent HSV-2 lesions was assessed.

Figure 14:
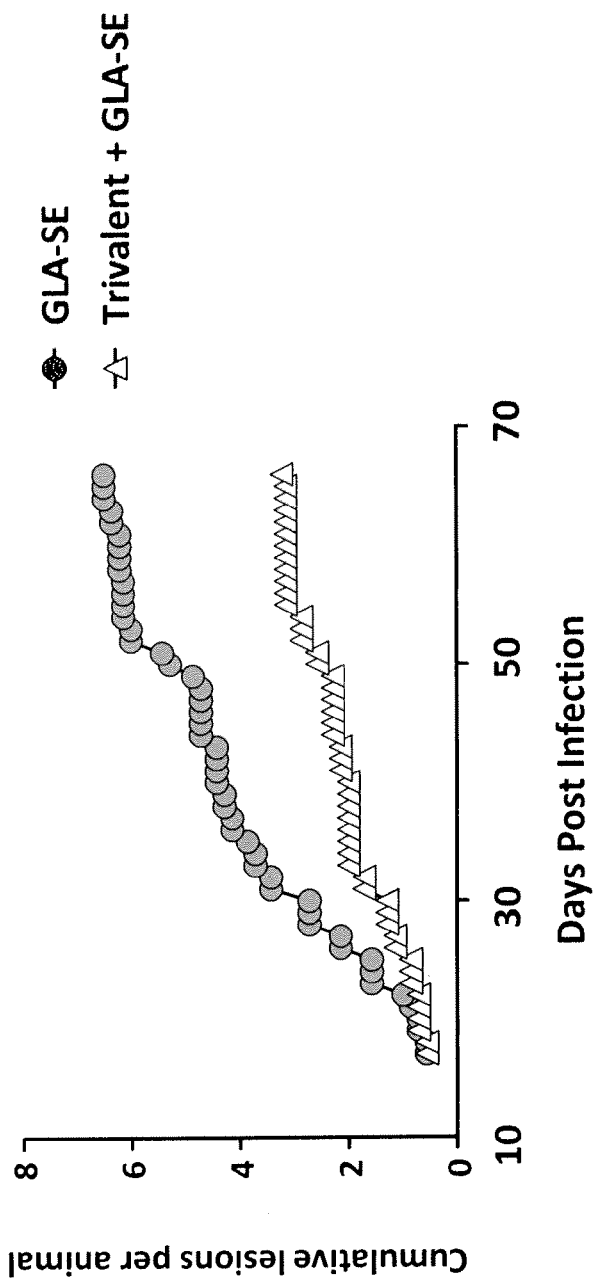
FIG. 14 shows data obtained when guinea pigs (7/group) were infected intravaginally with a sublethal dose of HSV-2 strain 333 virus and then treated on days 13 and 27 post infection with trivalent vaccine consisting of 5 µg each of recombinant gD2, UL19ud, and UL25 in combination with 5 µg GLA-SE. Infected guinea pigs treated with GLA-SE alone served as negative controls. Animals were monitored daily for vaginal lesions and scores of 0-4 were assigned for each lesion day. Daily lesions scores in each group were averaged and plotted versus time.

Groups of seven guinea pigs infected intravaginally with a sublethal dose of HSV-2 strain 333 virus. On days 13 and 27 post infection, guinea pigs were immunized with a trivalent vaccine consisting of 5 μg each of recombinant gD2, UL19ud (see SEQ ID NO:12), and UL25 in combination with 5 μg GLA-SE. Infected guinea pigs treated with GLA-SE alone served as negative controls. Animals were monitored daily for vaginal lesions and scores of 0-4 were assigned for each lesion day. Daily lesions scores in each group were averaged and plotted versus time. As depicted in FIG. 14, animals treated with trivalent vaccine plus GLA-SE had approximately a 50% reduction in recurrent lesions compared to animals treated with GLA-SE alone.

Example 12

Construction of Immunogenic Protein Derived from HSV-2 Envelope Glycoprotein and Containing a Leader Sequence In this example, an immunogenic protein is constructed from gD2 sequence and comprises the gD2 leader sequence.

The leader sequence of gD2 is 40 amino acids long (residues 1-40 in SEQ ID No.: 1). A nucleotide sequence encoding a 100 amino acid fragment (residues 1-100) is inserted into an expression vector. Site-directed mutagenesis is used to change residues 38-42 from CysAlaLysTyr (SEQ ID NO: 16) to GlyLeuAlaVal (SEQ ID NO: 17) or other sequence that isn't cleaved during protein synthesis. CHO cells are transformed with the vector containing the altered sequence and gD2 protein is isolated. Alternatively, the nucleotide sequence is inserted into a baculovirus expression vector and protein isolated from Sf9 cells. Verification that the leader sequence is present is obtained by HPLC analysis.

Example 13

Protective Efficacy of GLA/SE Plus Recombinant Trivalent Protein Vaccine Against Lethal Challenge with Virulent HSV-2

In this example, the ability of a trivalent recombinant HSV-2 protein vaccine plus GLA adjuvant to protect against lethal HSV-2 was assessed.

Groups of ten C57BL/6 mice were given two intramuscular immunizations, separated by 28 days, of trivalent vaccine consisting of 5 μg each of recombinant gD2, UL19ud (see SEQ ID NO:12) and UL25 in combination with either 5 μg GLA-SE or 5% dextrose vehicle. Mice immunized with 5 μg GLA-SE alone served as negative controls. An additional control group consisted of mice immunized with 5 μg GLA-SE and 1 milligram per ml of aciclovir (ACV) in the drinking water starting 24 hours after challenge. Twenty-two days after the second immunization, mice were treated with depot medroxyprogesterone acetate and then challenged six days later with a 50×LD$_{50}$ dose of wild-type HSV-2 intravaginally. Mice monitored daily for formation of genital lesions and survival. On days 1, 3, and 5 post infection, vaginal swabs were collected for quantitation of HSV-2 DNA by PCR.

Figure 15:
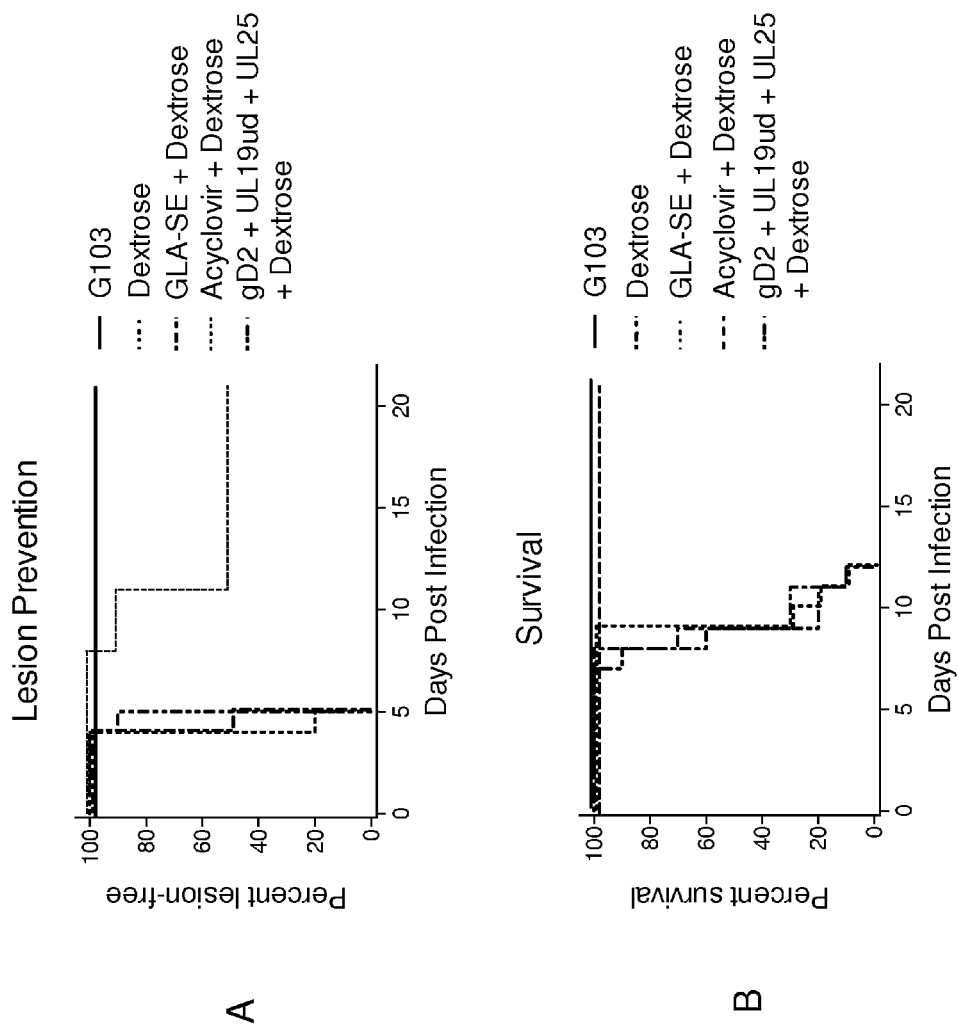
FIG. 15 shows data obtained when groups of ten C57BL/6 mice were given two intramuscular immunizations, separated by 28 days, of trivalent vaccine consisting of 5 µg each of recombinant gD2, UL19ud (see SEQ ID NO:12) and UL25 in combination with either 5 µg GLA-SE or 5% dextrose vehicle. Mice immunized with 5 µg GLA-SE alone served as negative controls. An additional control group consisted of mice immunized with 5 µg GLA-SE and 1 milligram per ml of aciclovir (ACV) in the drinking water starting 24 hours after challenge. Twenty-two days after the second immunization, mice were treated with depot medroxyprogesterone acetate and then challenged six days later with a 50×LD$_{50}$ dose of wild-type HSV-2 intravaginally. Mice were monitored daily for formation of genital lesions (panel A) and survival (panel B).
Figure 16:
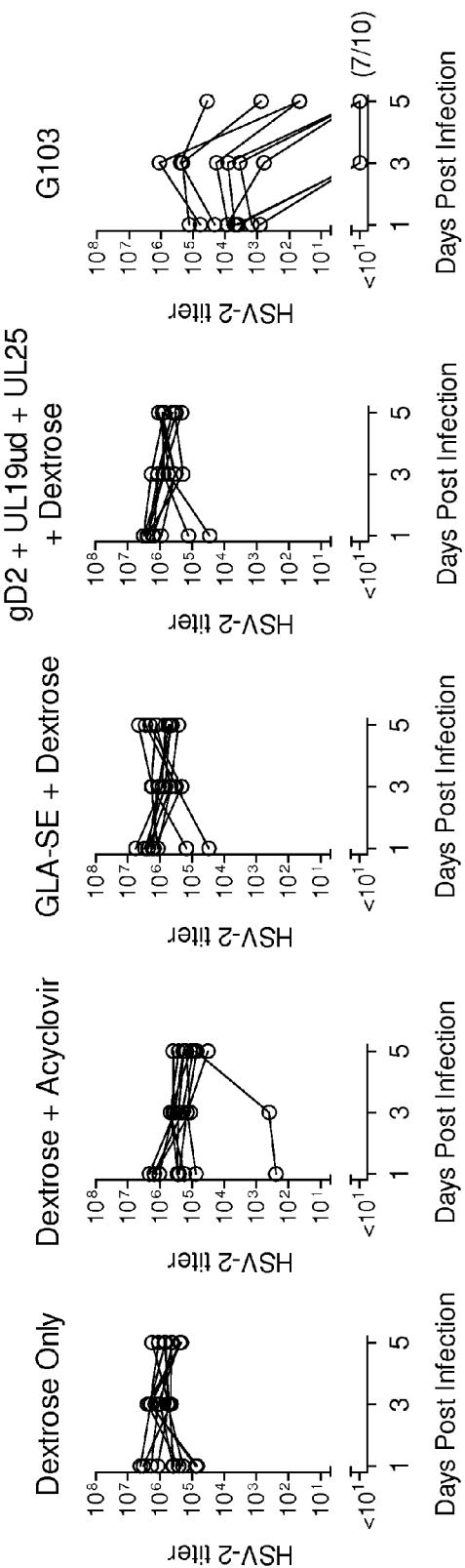
FIG. 16: shows vaginal HSV-2 DNA levels in mice immunized with trivalent gD2, UL19ud (SEQ ID NO:12) and UL25 vaccine (see FIG. 15 for description of groups of mice). Vaginal swabs were collected on days 1, 3, and 5 post infection, for quantitation of HSV-2 DNA by PCR.

As depicted in FIG. 15, mice immunized with trivalent recombinant gD2, UL19ud and UL25 with GLA-SE have dramatically reduced lesion formation (panel A) and have increased survival (panel B) compared to mice immunized with either trivalent protein vaccine alone or GLA-SE alone. Likewise, as depicted in FIG. 16, 7 out of 10 mice immunized with gD2/UL19ud/UL25 with GLA-SE had no detectable vaginal HSV-2 DNA by day 5, whereas mice in all three control groups showed sustained levels of HSV-2 in the vagina through day 5. The animals that received acyclovir also had the same high HSV-2 DNA viral loads on days 1, 3, and 5. The animals that received the active vaccine of GLA/SE plus gD2/UL19ud/UL25 had notably lower viral loads, with many animals sterilizing (i.e., no detectable viral loads) by day 5.

In summary, these experiments demonstrate in vivo protective efficacy of GLA/SE+ recombinant trivalent gD2/UL19ud/UL25 protein vaccine against lethal challenge with virulent HSV-2.

Example 14

Safety and Immunogenicity of Vaccine in Humans

The safety and immunogenicity of immunogens described above formulated with GLA-SE, or SE alone may be tested in a Phase 1A/1B study design using HSV-2 seronegative subjects (target for prophylactic vaccine) and HSV-2 seropositive subjects (target for immunotherapeutic vaccine). The study design may follow that established by the HIV Vaccine Trials Network (HVTN), and has been used in 40 human HIV-1 phase IA vaccine trials in the last 10 years.

The design of these Phase 1A trials consists of a standardized format of 12 subjects per group (10 vaccine—2 placebo) and is based upon the ability to define a serious adverse event at a 15% prevalence. Vaccines that are not immunogenic (<2 of 10 subjects develop immunity) are also defined. In the HSV-2 Phase 1A study, subjects receive 3 i.m. immunizations of 1 μg or 2.5 μg GLA-SE at 4 week intervals. A total of 48 HSV seronegative and HSV-2 seropositive subjects (HSV-1 seropositive or HSV-1 seronegative) are immunized in the Phase 1A trial.

HSV-2 seronegative subjects are defined by Western Blot at Day 0. In addition to safety assessments, subjects on study may be monitored for a possible vaccine-induced HSV-2 specific immune humoral and cellular immune response, and frequency of recurrence of genital ulcers (HSV-2 seropositive subjects only). For the HSV-2 infected population, two pre-vaccination time points may be used to establish antibody to gD2. Cellular immunity to HSV-2 recombinant proteins may be assessed by IFN-γ ELISPOT and ICS assays, and gD2-specific humoral immunity by ELISA and neutralizing antibody assays.

From the foregoing it will be appreciated that, although specific embodiments have been described herein for purposes of illustration, various modifications may be made without deviating from the spirit and scope of the invention. Accordingly, the invention is not limited except as by the appended claims.

What is claimed is:

1. A trivalent immunogenic composition comprising:
   (a) an immunogenic fragment of an Herpes Simplex virus type 2 (HSV-2) UL19 polypeptide wherein the immunogenic fragment of UL19 has the amino acid sequence set forth in SEQ ID NO: 12, and wherein the immunogenic fragment lacks at least 75% of amino acids 1-450 of SEQ ID NO: 4 and lacks at least 75% of amino acids of 1055-1374 of SEQ ID NO: 4; or an immunogenic variant thereof that retains at least 90% amino acid identity over the full length of the immunogenic fragment, glycoprotein D of HSV-2 (gD2), wherein the gD2 comprises the amino acid sequence set forth in SEQ ID NO: 2 or 3, or an immunogenic fragment thereof comprising at least 15 contiguous amino acids of SEQ ID NO: 2 or 3, and UL25, wherein the UL25 comprises the amino acid sequence set forth in SEQ ID NO: 5 or an immunogenic fragment thereof comprising at least 15 contiguous amino acids of SEQ ID NO: 5;
   (b) an amount of Glucopyranosyl Lipid Adjuvant (GLA) that increases the immune response; and
   (c) a pharmaceutically acceptable carrier.

2. The trivalent composition of claim 1, wherein the GLA is in the form of an oil-in-water emulsion or is in an aqueous form.

3. The trivalent composition of claim 2, wherein the oil-in-water emulsion comprises squalene.

4. A method of generating an immune response in a subject comprising administering the composition of any one of claims 1, 2 or 3 to the subject.

5. The method of claim 4 wherein the administration route is intradermal, mucosal, intramuscular, subcutaneous, sublingual, rectal, or vaginal.

6. The method of any one of claims 4 or 5 further comprising administering a second, third or fourth composition according to any one of claims 1, 2 or 3 to the subject.

7. The trivalent composition of claim 1, wherein the immunogenic fragment of UL19 has the amino acid sequence set forth in SEQ ID NO:12.

8. The trivalent composition of claim 1, wherein the immunogenic fragment of UL19 is fused to a heterologous peptide.

9. The trivalent composition of claim 8, wherein the heterologous peptide is a tag or a marker sequence.

10. The trivalent composition of claim 9, wherein the tag is a histidine tag which optionally comprises a cleavage sequence.

11. The trivalent composition of claim 1, wherein the UL25 comprises the amino acid sequence set forth in SEQ ID NO: 5, or a variant thereof that retains at least 90% amino acid identity over the full length of SEQ ID NO: 5 and is capable of inducing an immune response against the UL25 protein set forth in SEQ ID NO: 5, or an immunogenic fragment thereof comprising at least 15 contiguous amino acids of SEQ ID NO: 5.

12. The trivalent composition of claim 1, wherein the gD2 comprises the amino acid sequence set forth in SEQ ID NO:2 or 3, or a variant thereof that retains at least 90% amino acid identity over the full length of SEQ ID NO: 2 or 3 and is capable of inducing an immune response against the gD2 protein set forth in SEQ ID NO:2 or 3, or an immunogenic fragment thereof comprising at least 15 contiguous amino acids of SEQ ID NO: 2 or 3.

13. The trivalent composition of claim 1, wherein the UL25 comprises the amino acid sequence set forth in SEQ ID NO:5, or a variant thereof that retains at least 90% amino acid identity over the full length of SEQ ID NO: 5 and is capable of inducing an immune response against the UL25 protein set forth in SEQ ID NO:5, or an immunogenic fragment thereof comprising at least 15 contiguous amino acids of SEQ ID NO: 5; and wherein the gD2 comprises the amino acid sequence set forth in SEQ ID NO:2 or 3, or a variant thereof that retains at least 90% amino acid identity over the full length of SEQ ID NO: 2 or 3 and is capable of inducing an immune response against the gD2 protein set forth in SEQ ID NO: 2 or 3, or an immunogenic fragment thereof comprising at least 15 contiguous amino acids of SEQ ID NO: 2 or 3.

14. The trivalent composition of claim 1, wherein gD2 is fused to a heterologous peptide, or UL25 is fused to a heterologous peptide, or both.

* * * * *

UNITED STATES PATENT AND TRADEMARK OFFICE
CERTIFICATE OF CORRECTION

PATENT NO. : 9,555,099 B2  
APPLICATION NO. : 13/895888  
DATED : January 31, 2017  
INVENTOR(S) : Thomas W. Dubensky, Jr. et al.

Page 1 of 1

It is certified that error appears in the above-identified patent and that said Letters Patent is hereby corrected as shown below:

In the Claims

At Column 87, Line 8, "1-450" should be -- of 1-450 --.

At Column 87, Line 22, "trivalent" should be -- trivalent immunogenic --.

At Column 87, Line 25, "trivalent" should be -- trivalent immunogenic --.

At Column 87, Line 36, "trivalent" should be -- trivalent immunogenic --.

At Column 87, Line 39, "trivalent" should be -- trivalent immunogenic --.

At Column 88, Line 1, "trivalent" should be -- trivalent immunogenic --.

At Column 88, Line 3, "trivalent" should be -- trivalent immunogenic --.

At Column 88, Line 6, "trivalent" should be -- trivalent immunogenic --.

At Column 88, Line 15, "trivalent" should be -- trivalent immunogenic --.

At Column 88, Line 23, "trivalent" should be -- trivalent immunogenic --.

At Column 88, Line 38, "trivalent" should be -- trivalent immunogenic --.

Signed and Sealed this  
Twenty-ninth Day of August, 2017

Joseph Matal  
*Performing the Functions and Duties of the*  
*Under Secretary of Commerce for Intellectual Property and*  
*Director of the United States Patent and Trademark Office*